```
  1  ATGGCTATAGAAACTGGTTACACCCCAATCGATATTTCCT      40

United States Patent [19]
Fischhoff et al.
[11] Patent Number: 5,880,275
[45] Date of Patent: Mar. 9, 1999
[54] **SYNTHETIC PLANT GENES FROM *BT KURSTAKI* AND METHOD FOR PREPARATION**
[75

41  TGTCGCTAACGCAATTTCTTTTGAGTGAATTTGTTCCCGG      80

81  TGCTGGATTTGTGTTAGGACTAGTTGATATAATATGGGA      120
                             T   C

121  ATTTTTGGTCCCTCTCAATGGGACGCATTTCTTGTACAAA     160

161  TTGAACAGTTAATTAACCAAAGAATAGAAGAATTCGCTAG     200
          C C  C         G    C       G

201  GAACCAAGCCATTTCTAGATTAGAAGGACTAAGCAATCTT     240
          T

241  TATCAAATTTACGCAGAATCTTTTAGAGAGTGGGAAGCAG     280

281  ATCCTACTAATCCAGCATTAAGAGAAGAGATGCGTATTCA     320

321  ATTCAATGACATGAACAGTGCCCTTACAACCGCTATTCCT     360

361  CTTTTTGCAGTTCAAAATTATCAAGTTCCTCTTTTATCAG     400
                                  CC C   C

401  TATATGTTCAAGCTGCAAATTTACATTTATCAGTTTTGAG     440
       G  C         C  CC C  CC C

441  AGATGTTTCAGTGTTTGGACAAAGGTGGGGATTTGATGCC     480

481  GCGACTATCAATAGTCGTTATAATGATTTAACTAGGCTTA     520

521  TTGGCAACTATACAGATCATGCTGTACGCTGGTACAATAC     560

561  GGGATTAGAGCGTGTATGGGGACCGGATTCTAGAGATTGG     600

601  ATAAGATATAATCAATTTAGAAGAGAATTAACACTAACTG     640
            C  G  C  C   G C       GC T

641  TATTAGATATCGTTTCTCTATTTCCGAACTATGATAGTAG     680

681  AACGTATCCAATTCGAACAGTTTCCCAATTAACAAGAGAA     720
```

FIG. 2A

| | | |
|---|---|---|
| 721 | ATTTATACAAACCCAGTATTAGAAAATTTTGATGGTAGTT | 760 |
| 761 | TTCGAGGCTCGGCTCAGGGCATAGAAGGAAGTATTAGGAG | 800 |
| 801 | TCCACATTTGATGGATATACTTAATAGTATAACCATCTAT | 840 |
| 841 | ACGGATGCTCATAGAGGAGAATATTATTGGTCAGGCATC<br>                  C   C       C T   C | 880 |
| 881 | AAATAATGGCTTCTCCTGTAGGGTTTTCGGGGCCAGAATT<br>  G  C | 920 |
| 921 | CACTTTTCCGCTATATGGAACTATGGGAAATGCAGCTCCA | 960 |
| 961 | CAACAACGTATTGTTGCTCAACTAGGTCAGGGCGTGTATA | 1000 |
| 1001 | GAACATTATCGTCCACCTTATATAGAAGACCTTTTAATAT<br>                                   C | 1040 |
| 1041 | AGGGATAAATAATCAACAACTATCTGTTCTTGACGGGACA<br>C     C    C   C | 1080 |
| 1081 | GAATTTGCTTATGGAACCTCCTCAAATTTGCCATCCGCTG | 1120 |
| 1121 | TATACAGAAAAGCGGAACGGTAGATTCGCTGGATGAAAT | 1160 |
| 1161 | ACCGCCACAGAATAACAACGTGCCACCTAGGCAAGGATTT | 1200 |
| 1201 | AGTCATCGATTAAGCCATGTTTCAATGTTTCGTTCAGGCT | 1240 |
| 1241 | TTAGTAATAGTAGTGTAAGTATAATAAGAGCTCCTATGTT | 1280 |
| 1281 | CTCTTGGATACATCGTAGTGCTGAATTTAATAATATAATT<br>                   G  C    C    C    C    C | 1320 |
| 1321 | CCTTCATCACAAATTACACAAATACCTTTAACAAAATCTA<br>    C  C     C  AC C     G | 1360 |
| 1361 | CTAATCTTGGCTCTGGAACTTCTGTCGTTAAAGGACCAGG | 1400 |

FIG. 2B

1401 ATTTACAGGAGGAGATATTCTTCGAAGAACTTCACCTGGC 1440

1441 CAGATTTCAACCTTAAGAGTAAATATTACTGCACCATTAT 1480

1481 CACAAAGATATCGGGTAAGAATTCGCTACGCTTCTACCAC 1520

1521 AAATTTACAATTCCATACATCAATTGACGGAAGACCTATT 1560
       CC T  G     C

1561 AATCAGGGGAATTTTTCAGCAACTATGAGTAGTGGGAGTA 1600

1601 ATTTACAGTCCGGAAGCTTTAGGACTGTAGGTTTTACTAC 1640

1641 TCCGTTTAACTTTTCAAATGGATCAAGTGTATTTACGTTA 1680

1681 AGTGCTCATGTCTTCAATTCAGGCAATGAAGTTTATATAG 1720

1721 ATCGAATTGAATTTGTTCCGGCA 1743

FIG. 2C

```
  1  ATGGATAACAATCCGAACATCAATGAATGCATTCCTTATA   40
         C    C  A                 A  C

41  ATTGTTTAAGTAACCCTGAAGTAGAAGTATTAGGTGGAGA   80
        C  C G        A    T      C T

81  AAGAATAGAAACTGGTTACACCCCAATCGATATTTCCTTG  120
        C  C T      C       T  C    C C

121  TCGCTAACGCAATTTCTTTTGAGTGAATTTGTTCCCGGTG  160
       CT G  A   G       GC C   C  G C  G  A

161  CTGGATTTGTGTTAGGACTAGTTGATATAATATGGGGAAT  200
        G  C   TC C             C  C C    T

201  TTTTGGTCCCTCTCAATGGGACGCATTTCTTGTACAAATT  240
        C            A      T     C G G

241  GAACAGTTAATTAACCAAAGAATAGAAGAATTCGCTAGGA  280
        G    G  C    G    G  C    G    C

281  ACCAAGCCATTTCTAGATTAGAAGGACTAAGCAATCTTTA  320
        G   C    G  G         T G       C

321  TCAAATTTACGCAGAATCTTTTAGAGAGTGGGAAGCAGAT  360
        C    C T        GAGC C              C

361  CCTACTAATCCAGCATTAAGAGAAGAGATGCGTATTCAAT  400
            C    TC CC C  G  A

401  TCAATGACATGAACAGTGCCCTTACAACCGCTATTCCTCT  440
         C          C   T G  C      C   AT

441  TTTTGCAGTTCAAAATTATCAAGTTCCTCTTTTATCAGTA  480
        G  C    C G C C           C G C G

481  TATGTTCAAGCTGCAAATTTACATTTATCAGTTTTGAGAG  520
         C       A T   C T  CC CAGC  GC TC

521  ATGTTTCAGTGTTTGGACAAAGGTGGGGATTTGATGCCGC  560
         C  AGC         G              C   T

561  GACTATCAATAGTCGTTATAATGATTTAACTAGGCTTATT  600
       A C        C      C  C CC T        G

601  GGCAACTATACAGATcATGCTGTaCGCTGGTACAATACGG  640
        A    C  C CC C    T  T      C T

641  GATTAGAGCGTGTATGGGGACCGGATTCTAGAGATTGGAT  680
        C  G     C        T  T
```

FIG. 3A

```
681  AAGATATAATCAATTTAGAAGAGAATTAACACTAACTGTA   720
       T   C C G C G       G C C A T

721  TTAGATATCGTTTCTCTATTTCCGAACTATGATAGTAGAA   760
       G   C T G     C C           CTCC

761  CGTATCCAATTCGAACAGTTTCCCAATTAACAAGAGAAAT   800
       C C T C   T G         C T C

801  TTATACAAACCCAGTATTAGAAAATTTTGATGGTAGTTTT   840
       C   T        TC T G C C C      C C

841  CGAGGCTCGGCTCAGGGCATAGAAGGAAGTATTAGGAGTC   880
       T T T C A T C      CTCC C     C

881  CACATTTGATGGATATACTTAATAGTATAACCATCTATAC   920
       C        C CT G C C     T   C

921  GGATGCTCATAGAGGAGAATATTATTGGTCAGGGCATCAA   960
       C     C       G     C     T A C G

961  ATAATGGCTTCTCCTGTAGGGTTTTCGGGGCCAGAATTCA   1000
       C    C   A T A  CAGC      C G T

1001 CTTTTCCGCTATATGGAACTATGGGAAATGCAGCTCCACA   1040
       C    T C                 C C

1041 ACAACGTATTGTTGCTCAACTAGGTCAGGGCGTGTATAGA   1080
       C                         T C C

1081 ACATTATCGTCCACCTTATATAGAAGACCTTTTAATATAG   1120
       C G T        G C         C C   C

1121 GGATAAATAATCAACAACTATCTGTTCTTGACGGGACAGA   1160
       T C C C G   T C           A

1161 ATTTGCTTATGGAACCTCCTCAAATTTGCCATCCGCTGTA   1200
       G C C        T T C                  T

1201 TACAGAAAAAGCGGAACGGTAGATTCGCTGGATGAAATAC   1240
          G         C T   CT  C    C

1241 CGCCACAGAATAACAACGTGCCACCTAGGCAAGGATTTAG   1280
       A     C   T      C           CTC

1281 TCATCGATTAAGCCATGTTTCAATGTTTCGTTCAGGCTTT   1320
       C  CA G G    C G C     C    C A C

1321 AGTAATAGTAGTGTAAGTATAATAAGAGCTCCTATGTTCT   1360
       C  C  TCC G   C  C C

1361 CTTGGATACATCGTAGTGCTGAATTTAATAATATAATTCC   1400
       A    T          G  C C           C
```

FIG. 3B

```
1401   TTCATCACAAATTACACAAATACCTTTAACAAAATCTACT    1440
         C  T    C C      C  A  G  C  G

1441   AATCTTGGCTCTGGAACTTCTGTCGTTAAAGGACCAGGAT    1480
         C   A                G         C

1481   TTACAGGAGGAGATATTCTTCGAAGAACTTCACCTGGCCA    1520
         C      T        A        T

1521   GATTCAACCTTAAGAGTAAATATTACTGCACCATTATCA     1560
        AGC   C C     T  C C        C T  T

1561   CAAAGATATCGGGTAAGAATTCGCTACGCTTCTACCACAA    1600
              T  C G    T     A        A

1601   ATTTACAATTCCATACATCAATTGACGGAAGACCTATTAA    1640
         C  G      C  C C C         G   C

1641   TCAGGGAATTTTTCAGCAACTATGAGTAGTGGGAGTAAT     1680
          T   C  C C    C   TCA  C  C C C

1681   TTACAGTCCGGAAGCTTTAGGACTGTAGGTTTTACTACTC    1720
        G  A    C       C  A C C    C

1721   CGTTTAACTTTTCAAATGGATCAAGTGTATTTACGTTAAG    1760
         T  C   C  T C        C  T  C  CC T

1761   TGCTCATGTCTTCAATTCAGGCAATGAAGTTTATATAGAT    1800
         C         G     T        G C T  C

1801   CGAATTGAATTTGTTCCGGCAGAAGTAACCTTTGAGGCAG    1840
          T    G    G  T C     T    C    T

1841   AATAT    1845
         G  C
```

FIG. 3C

```
  1  ATGGATAACAATCCGAACATCAATGAATGCATTCCTTATA   40
         C      C  A         C           A  C

41  ATTGTTTAAGTAACCCTGAAGTAGAAGTATTAGGTGGAGA   80
       C  C   G        A  T        C T

81  AAGAATAGAAACTGGTTACACCCCAATCGATATTTCCTTG  120
       C C  T      C         T C      C  C

121  TCGCTAACGCAATTTCTTTTGAGTGAATTTGTTCCCGGTG  160
       CT G  A   G       GC C  C G  C G  A

161  CTGGATTTGTGTTAGGACTAGTTGATATAATATGGGGAAT  200
        G  C  TC C              C  C C    T

201  TTTTGGTCCCTCTCAATGGGACGCATTTCTTGTACAAATT  240
         C        A       T    C G G

241  GAACAGTTAATTAACCAAAGAATAGAAGAATTCGCTAGGA  280
        G   G  C     G  G  C   G    C

281  ACCAAGCCATTTCTAGATTAGAAGGACTAAGCAATCTTTA  320
        G    C    G G       T G       C

321  TCAAATTTACGCAGAATCTTTTAGAGAGTGGGAAGCAGAT  360
       C    C  T        GAGC  C            C

361  CCTACTAATCCAGCATTAAGAGAAGAGATGCGTATTCAAT  400
            C    TC CC  C  G  A

401  TCAATGACATGAACAGTGCCCTTACAACCGCTATTCCTCT  440
        C         C  T G  C      C  AT

441  TTTTGCAGTTCAAAATTATCAAGTTCCTCTTTTATCAGTA  480
     G  C      C G C  C           C  G  C  G

481  TATGTTCAAGCTGCAAATTTACATTTATCAGTTTTGAGAG  520
        C         A  T    C T  CC CAGC  GC TC

521  ATGTTTCAGTGTTTGGACAAAGGTGGGGATTTGATGCCGC  560
       C  AGC       G                  C    T

561  GACTATCAATAGTCGTTATAATGATTTAACTAGGCTTATT  600
       A  C       C        C  C CC T       G

601  GGCAACTATACAGATTATGCTGTACGCTGGTACAATACGG  640
        A    C  CC C    T T      C T

641  GATTAGAACGTGTATGGGGACCGGATTCTAGAGATTGGGT  680
        C  G G    C    T T                 A
```

FIG. 4A

```
681  AAGGTATAATCAATTTAGAAGAGAATTAACACTAACTGTA  720
     T  A  C C  G  CG         G  CC  A  T

721  TTAGATATCGTTGCTCTGTTCCCGAATTATGATAGTAGAA  760
       G  C  T  GT  C        C     CTCC

761  GATATCCAATTCGAACAGTTTCCCAATTAACAAGAGAAAT  800
     CC  C  T  C  T     G       C T  C

801  TTATACAAACCCAGTATTAGAAAATTTTGATGGTAGTTTT  840
       C    T        TC T G CCC       C C

841  CGAGGCTCGGCTCAGGGCATAGAAAGAAGTATTAGGAGTC  880
        T  T  T  C  A T  C  G CTCC  C     C

881  CACATTTGATGGATATACTTAACAGTATAACCATCTATAC  920
         C        C   CT G    C    T     C

921  GGATGCTCATAGGGGTTATTATTATTGGTCAGGGCATCAA  960
       C        C  A  AG G    C      T A C G

961  ATAATGGCTTCTCCTGTAGGGTTTTCGGGGCCAGAATTCA  1000
        C     C     A  T  A  CAGC     C G  T

1001 CTTTTCCGCTATATGGAACTATGGGAAATGCAGCTCCACA  1040
        C    T  C                  C  C

1041 ACAACGTATTGTTGCTCAACTAGGTCAGGGCGTGTATAGA  1080
             C                    T  C  C

1081 ACATTATCGTCCACTTTATATAGAAGACCTTTTAATATAG  1120
       C  G  T     C G  C        C C    C

1121 GGATAAATAATCAACAACTATCTGTTCTTGACGGGACAGA  1160
       T  C  C  G     T  C       A

1161 ATTTGCTTATGGAACCTCCTCAAATTTGCCATCCGCTGTA  1200
       G  C  C        T  T  C              T

1201 TACAGAAAAAGCGGAACGGTAGATTCGCTGGATGAAATAC  1240
             G         C  T    CT   C     C

1241 CGCCACAGAATAACAACGTGCCACCTAGGCAAGGATTTAG  1280
        A     C    T         C          CTC

1281 TCATCGATTAAGCCATGTTTCAATGTTTCGTTCAGGCTTT  1320
     C  CA G  G      C G C     C      C A  C

1321 AGTAATAGTAGTGTAAGTATAATAAGAGCTCCTATGTTCT  1360
        C  C    TCC  G  C   C  C

1361 CTTGGATACATCGTAGTGCTGAATTTAATAATATAATTGC  1400
           C              G  C  C  C  C
```

FIG. 4B

```
1401  ATCGGATAGTATTACTCAAATCCCTGCAGTGAAGGGAAAC   1440
                                             C

1441  TTTCTTTTTAATGGTTCTGTAATTTCAGGACCAGGATTTA   1480
          C  C C          C                  C

1481  CTGGTGGGGACTTAGTTAGATTAAATAGTAGTGGAAATAA   1520
           A   C C       C C  C C

1521  CATTCAGAATAGAGGGTATATTGAAGTTCCAATTCACTTC   1560

1561  CCATCGACATCTACCAGATATCGAGTTCGTGTACGGTATG   1600
         C                    A         GA

1601  CTTCTGTAACCCCGATTCACCTCAACGTTAATTGGGGTAA   1640
              G   T

1641  TTCATCCATTTTTTCCAATACAGTACCAGCTACAGCTACG   1680
              C C          T              C

1681  TCATTAGATAATCTACAATCAAGTGATTTGGTTATTTTG    1720
        C  G       C     C C      C    C

1721  AAAGTGCCAATGCTTTACATCTTCATTAGGTAATATAGT   1760
                    C C       C C

1761  AGGTGTTAGAAATTTTAGTGGGACTGCAGGAGTGATAATA   1800
        G        C                      T  C

1801  GACAGATTTGAATTTATTCCAGTTACTGCAACACTCGAGG   1840
            C   G  C

1841  CTGAATATAATCTGGAAAGAGCGCAGAAGGCGGTGAATGC   1880
                                        A TGCG

1881  GCTGTTTACGTCTACAAACCAACTAGGGCTAAAAACAAAT   1920
        CTGT  ACGTCTACA  C AGCT G ACTC  G CA  TG

```
  1 GAAAGAATAGAAACTGGTTACACCCCAATCGATATTTCCT   40
    ATGGCC   T          C         T  C    C C

41 TGTCGCTAACGCAATTTCTTTTGAGTGAATTTGTTCCCGG   80
    CT G    A  G          GC C    C G C G  A

81 TGCTGGATTTGTGTTAGGACTAGTTGATATAATATGGGGA  120
        G    C   TC C              C  C  C  T

121 ATTTTTGGTCCCTCTCAATGGGACGCATTTCTTGTACAAA  160
      C         A       T       C G G

161 TTGAACAGTTAATTAACCAAAGAATAGAAGAATTCGCTAG  200
         G    G C      G   G C     G      C

201 GAACCAAGCCATTTCTAGATTAGAAGGACTAAGCAATCTT  240
          G   C      G G     T G         C

241 TATCAAATTACGCAGAATCTTTTAGAGAGTGGGAAGCAG   280
       C     C  T        GAGC C           C

281 ATCCTACTAATCCAGCATTAAGAGAAGAGATGCGTATTCA  320
            C    TC CC C  G  A

321 ATTCAATGACATGAACAGTGCCCTTACAACCGCTATTCCT  360
           C         C  T G C  A     C  A

361 CTTTTTGCAGTTCAAAATTATCAAGTTCCTCTTTTATCAG  400
    T G  C     C G C  C              C G C

401 TATATGTTCAAGCTGCAAATTTACATTTATCAGTTTTGAG  440
      G  C      A  T   C T  CC CAGC  GC TC

441 AGATGTTTCAGTGTTTGGACAAAGGTGGGGATTTGATGCC  480
        C  AGC       G             C     T

481 GCGACTATCAATAGTCGTTATAATGATTTAACTAGGCTTA  520
      A C       C      C  C CC T         G

521 TTGGCAACTATACAGATTATGCTGTACGCTGGTACAATAC  560
        A    C C  CC C     T T         C

561 GGGATTAGAACGTGTATGGGGACCGGATTCTAGAGATTGG  600
    T   C  G       C      T T

601 GTAAGGTATAATCAATTTAGAAGAGAATTAACACTAACTG  640
    A T A  C  C G C       G        C C A

641 TATTAGATATCGTTGCTCTGTTCCCGAATTATGATAGTAG  680
      T  G  C T  GT  C          C     CTCC
```

FIG. 8A

```
681  AAGATATCCAATTCGAACAGTTTCCCAATTAACAAGAGAA  720
       CC  C  T  C  T     G     C T  C

721  ATTTATACAAACCCAGTATTAGAAAATTTTGATGGTAGTT  760
       C    T        TC T G C   C    C

761  TTCGAGGCTCGGCTCAGGGCATAGAAAGAAGTATTAGGAG  800
       C T  T  T  C  A T C   G CTCC   C

801  TCCACATTTGATGGATATACTTAACAGTATAACCATCTAT  840
       C    C          C CT G   C    T     C

841  ACGGATGCTCATAGGGGTTATTATTATTGGTCAGGGCATC  880
              C     C A  AG G       C    T A C

881  AAATAATGGCTTCTCCTGTAGGGTTTTCGGGGCCAGAATT  920
         G  C     C    A T A CAGC    C  G

921  CACTTTTCCGCTATATGGAACTATGGGAAATGCAGCTCCA  960
        T  C    T C                    C C

961  CAACAACGTATTGTTGCTCAACTAGGTCAGGGCGTGTATA  1000
              C                      T  C C

1001 GAACATTATCGTCCACTTTATATAGAAGACCTTTTAATAT  1040
         C   G  T    C G C          C  C

1041 AGGGATAAATAATCAACAACTATCTGTTCTTGACGGGACA  1080
         C   T  C  C G    T  C         A

1081 GAATTTGCTTATGGAACCTCCTCAAATTTGCCATCCGCTG  1120
        G  C  C          T  T  C

1121 TATACAGAAAAAGCGGAACGGTAGATTCGCTGGATGAAAT  1160
         T       G      C  T    CT    C

1161 ACCGCCACAGAATAACAACGTGCCACCTAGGCAAGGATTT  1200
       C  A       C    T      C         C

1201 AGTCATCGATTAAGCCATGTTTCAATGTTTCGTTCAGGCT  1240
     TCC  CA G  G    C G C      C     C  A

1241 TTAGTAATAGTAGTGTAAGTATAATAAGAGCTCCTATGTT  1280
        C   C  C    TCC G  C  C  C

1281 CTCTTGGATACATCGTAGTGCTGAATTTAATAATATAATT  1320
             C              G C  C C C  C

1321 GCATCGGATAGTATTACTCAAATCCCTGCAGTGAAGGGAA  1360
             C

1361 ACTTTCTTTTAATGGTTCTGTAATTTCAGGACCAGGATT  1400
         C  C C              C
```

FIG. 8B

```
1401  TACTGGTGGGGACTTAGTTAGATTAAATAGTAGTGGAAAT     1440
         C      A   C C      C C C  C

1441  AACATTCAGAATAGAGGGTATATTGAAGTTCCAATTCACT     1480

1481  TCCCATCGACATCTACCAGATATCGAGTTCGTGTACGGTA     1520
              C                 A        GA

1521  TGCTTCTGTAACCCCGATTCACCTCAACGTTAATTGGGGT     1560
                G    T

1561  AATTCATCCATTTTTTCCAATACAGTACCAGCTACAGCTA     1600
                C C            T

1601  CGTCATTAGATAATCTACAATCAAGTGATTTGGTTATTT      1640
         C C G       C    C C       C    C

1641  TGAAAGTGCCAATGCTTTTACATCTTCATTAGGTAATATA     1680
                                  C C    C C

1681  GTAGGTGTTAGAAATTTTAGTGGGACTGCAGGAGTGATAA     1720
         G           C                      T

1721  TAGACAGATTTGAATTTATTCCAGTTACTGCAACACTCGA     1760
          C         C G C

1761  GGCTGAA    1767
          G
```

FIG. 8C

```
  1   ATGGATAACAATCCGAACATCAATGAATGCATTCCTTATA    40
        C      C A       C              A C

41   ATTGTTTAAGTAACCCTGAAGTAGAAGTATTAGGTGGAGA    80
       C C  G     A   T      C T

81   AAGAATAGAAACTGGTTACACCCCAATCGATATTTCCTTG   120
       C C T    C      T C    C C

121   TCGCTAACGCAATTTCTTTTGAGTGAATTTGTTCCCGGTG   160
       CT G  A G        GC C  C G C A

161   CTGGATTTGTGTTAGGACTAGTTGATATAATATGGGGAAT   200
         G C TC C          C C C    T

201   TTTTGGTCCCTCTCAATGGACGCATTTCTTGTACAAATT    240
          C     A       T   C G G

241   GAACAGTTAATTAACCAAAGAATAGAAGAATTCGCTAGGA   280
         G    G C    G G C   G  C

281   ACCAAGCCATTTCTAGATTAGAAGGACTAAGCAATCTTTA   320
         G    C     G G    T G      C

321   TCAAATTTACGCAGAATCTTTTAGAGAGTGGGAAGCAGAT   360
       C    C T     GAGC  C              C

361   CCTACTAATCCAGCATTAAGAGAAGAGATGCGTATTCAAT   400
         C       TC CC C   G A

401   TCAATGACATGAACAGTGCCCTTACAACCGCTATTCCTCT   440
        C         C    T G C  A    C AT

441   TTTTGCAGTTCAAAATTATCAAGTTCCTCTTTTATCAGTA   480
       G C   C G C C          C G C G

481   TATGTTCAAGCTGCAAATTTACATTTATCAGTTTTGAGAG   520
         C     A  T   C T  CC CAGC  GC TC

521   ATGTTTCAGTGTTTGGACAAAGGTGGGGATTTGATGCCGC   560
         C  AGC       G              C   T

561   GACTATCAATAGTCGTTATAATGATTTAACTAGGCTTATT   600
       A C       C     C  CC T        G

601   GGCAACTATACAGATTATGCTGTACGCTGGTACAATACGG   640
        A   C  CC C   T  T      C T

641   GATTAGAACGTGTATGGGGACCGGATTCTAGAGATTGGGT   680
         C G G  C   T T                 A
```

FIG.9A

```
681   AAGGTATAATCAATTTAGAAGAGAATTAACACTAACTGTA   720
      T  A  C  C G C G        G  C  C  A T

721   TTAGATATCGTTGCTCTGTTCCCGAATTATGATAGTAGAA   760
       G  C  T GT    C        C      CTCC

761   GATATCCAATTCGAACAGTTTCCCAATTAACAAGAGAAAT   800
      CC  C  T  C  T      G       C T  C

801   TTATACAAACCCAGTATTAGAAAATTTTGATGGTAGTTTT   840
       C    T         TC T G  C C C     C C

841   CGAGGCTCGGCTCAGGGCATAGAAGAAGTATTAGGAGTC   880
          T  T  T  C  A T  C   G CTCC  C    C

881   CACATTTGATGGATATACTTAACAGTATAACCATCTATAC   920
          C         C  CT G    C    T    C

921   GGATGCTCATAGGGGTTATTATTATTGGTCAGGGCATCAA   960
          C      C  A AG G    C      T  A C G

961   ATAATGGCTTCTCCTGTAGGGTTTTCGGGGCCAGAATTCA   1000
        C    C     A  T  A  CAGC    C G  T

1001  CTTTTCCGCTATATGGAACTATGGGAAATGCAGCTCCACA   1040
       C      T  C                   C  C

1041  ACAACGTATTGTTGCTCAACTAGGTCAGGGCGTGTATAGA   1080
              C                    T  C  C

1081  ACATTATCGTCCACTTTATATAGAAGACCTTTTAATATAG   1120
        C G  T    C G C        C  C    C

1121  GGATAAATAATCAACAACTATCTGTTCTTGACGGGACAGA   1160
        T  C  C  C G    T  C          A

1161  ATTTGCTTATGGAACCTCCTCAAATTTGCCATCCGCTGTA   1200
       G  C C          T T  C              T

1201  TACAGAAAAAGCGGAACGGTAGATTCGCTGGATGAAATAC   1240
             G      C  T    CT   C     C

1241  CGCCACAGAATAACAACGTGCCACCTAGGCAAGGATTTAG   1280
       A     C   T      C               CTC

1281  TCATCGATTAAGCCATGTTTCAATGTTTCGTTCAGGCTTT   1320
       C  CA G  G      C G C      C    C A C

1321  AGTAATAGTAGTGTAAGTATAATAAGAGCTCCTATGTTCT   1360
         C  C   TCC G  C  C  C

1361  CTTGGATACATCGTAGTGCTGAATTTAATAATATAATTGC   1400
            C            G  C  C  C  C
```

FIG.9B

```
1401 ATCGGATAGTATTACTCAAATCCCTGCAGTGAAGGGAAAC            1440
                                             C
1441 TTTCTTTTTAATGGTTCTGTAATTTCAGGACCAGGATTTA            1480
        C  C C              C           C
1481 CTGGTGGGACTTAGTTAGATTAAATAGTAGTGGAAATAA             1520
        A   C C       C  C  C
1521 CATTCAGAATAGAGGGTATATTGAAGTTCCAATTCACTTC            1560

1561 CCATCGACATCTACCAGATATCGAGTTCGTGTACGGTATG            1600
        C                A            GA
1601 CTTCTGTAACCCCGATTCACCTCAACGTTAATTGGGGTAA            1640
           G    T
1641 TTCATCCATTTTTTCCAATACAGTACCAGCTACAGCTACG            1680
           C C              T             C
1681 TCATTAGATAATCTACAATCAAGTGATTTTGGTTATTTTG            1720
        C G      C    C C      C     C
1721 AAAGTGCCAATGCTTTTACATCTTCATTAGGTAATATAGT            1760
                      C C _   C C
1761 AGGTGTTAGAAATTTTAGTGGGACTGCAGGAGTGATAATA            1800
     G         C                        T C
1801 GACAGATTTGAATTTATTCCAGTTACTGCAACACTCGAGG            1840
        C   G C
1841 CTGAATATAATCTGGAAAGAGCGCAGAAGGCGGTGAATGC            1880

1881 GCTGTTTACGTCTACAAACCAACTAGGGCTAAAAACAAAT            1920

1921 GTAACGGATTATCATATTGATCAAGTGTCCAATTTAGTTA            1960

1961 CGTATTTATCGGATGAATTTTGTCTGGATGAAAAGCGAGA            2000

2001 ATTGTCCGAGAAAGTCAAACATGCGAAGCGACTCAGTGAT            2040

2041 GAACGCAATTTACTCCAAGATTCAAATTTCAAAGACATTA            2080

2081 ATAGGCAACCAGAACGTGGGTGGGCGGAAGTACAGGGAT             2120
```

FIG. 9C

```
2121  TACCATCCAAGGAGGGGATGACGTATTTAAAGAAAATTAC   2160

2161  GTCACACTATCAGGTACCTTTGATGAGTGCTATCCAACAT   2200

2201  ATTTGTATCAAAAAATCGATGAATCAAAATTAAAAGCCTT   2240

2241  TACCCGTTATCAATTAAGAGGGTATATCGAAGATAGTCAA   2280

2281  GACTTAGAAATCTATTTAATTCGCTACAATGCAAAACATG   2320

2321  AAACAGTAAATGTGCCAGGTACGGGTTCCTTATGGCCGCT   2360

2361  TTCAGCCCAAAGTCCAATCGGAAAGTGTGGAGAGCCGAAT   2400

2401  CGATGCGCGCCACACCTTGAATGGAATCCTGACTTAGATT   2440

2441  GTTCGTGTAGGGATGGAGAAAAGTGTGCCCATCATTCGCA   2480

2481  TCATTTCTCCTTAGACATTGATGTAGGATGTACAGACTTA   2520

2521  AATGAGGACCTAGGTGTATGGGTGATCTTTAAGATTAAGA   2560

2561  CGCAAGATGGGCACGCAAGACTAGGGAATCTAGAGTTTCT   2600

2601  CGAAGAGAAACCATTAGTAGGAGAAGCGCTAGCTCGTGTG   2640

2641  AAAAGAGCGGAGAAAAATGGAGAGACAAACGTGAAAAAT   2680

2681  TGGAATGGGAAACAAATATCGTTTATAAAGAGGCAAAGA   2720

2721  ATCTGTAGATGCTTTATTTGTAAACTCTCAATATGATCAA   2760

2761  TTACAAGCGGATACGAATATTGCCATGATTCATGCGGCAG   2800

2801  ATAAACGTGTTCATAGCATTCGAGAAGCTTATCTGCCTGA   2840
```

FIG. 9D

```
2841  GCTGTCTGTGATTCCGGGTGTCAATGCGGCTATTTTGAA      2880

2881  GAATTAGAAGGGCGTATTTTCACTGCATTCTCCTATATG      2920

2921  ATGCGAGAAATGTCATTAAAAATGGTGATTTTAATAATGG     2960

2961  CTTATCCTGCTGGAACGTGAAAGGGCATGTAGATGTAGAA     3000

3001  GAACAAAACAACCAACGTTCGGTCCTTGTTGTTCCGGAAT     3040

3041  GGGAAGCAGAAGTGTCACAAGAAGTTCGTGTCTGTCCGGG     3080

3081  TCGTGGCTATATCCTTCGTGTCACAGCGTACAAGGAGGGA     3120

3121  TATGGAGAAGGTTGCGTAACCATTCATGAGATCGAGAACA     3160

3161  ATACAGACGAACTGAAGTTTAGCAACTGCGTAGAAGAGGA     3200

3201  AATCTATCCAAATAACACGGTAACGTGTAATGATTATACT     3240

3241  GTAAATCAAGAAGAATACGGAGGTGCGTACACTTCTCGTA     3280

3281  ATCGAGGATATAACGAAGCTCCTTCCGTACCAGCTGATTA     3320

3321  TGCGTCAGTCTATGAAGAAAATCGTATACAGATGGACGA     3360

3361  AGAGAGAATCCTTGTGAATTTAACAGAGGGTATAGGGATT     3400

3401  ACACGCCACTACCAGTTGGTTATGTGACAAAAGAATTAGA     3440

3441  ATACTTCCCAGAAACCGATAAGGTATGGATTGAGATTGGA     3480

3481  GAAACGGAAGGAACATTTATCGTGGACAGCGTGGAATTAC     3520

3521  TCCTTATGGAGGAA  3534
```

FIG.9E

```
  1  ATGGATAACAATCCGAACATCAATGAATGCATTCCTTATA   40
        C      C  A        C              A C

41  ATTGTTTAAGTAACCCTGAAGTAGAAGTATTAGGTGGAGA   80
        C C   G    A     T    C T

81  AAGAATAGAAACTGGTTACACCCCAATCGATATTTCCTTG  120
        C C  T    C        T C     C  C

121  TCGCTAACGCAATTTCTTTTGAGTGAATTTGTTCCCGGTG  160
       CT G  A   G        GC C  C G C G  A

161  CTGGATTTGTGTTAGGACTAGTTGATATAATATGGGGAAT  200
         G  C  TC C              C  C  C    T

201  TTTTGGTCCCTCTCAATGGGACGCATTTCTTGTACAAATT  240
         C      A        T     C G G

241  GAACAGTTAATTAACCAAAGAATAGAAGAATTCGCTAGGA  280
        G    G  C   G  G C   G      C

281  ACCAAGCCATTTCTAGATTAGAAGGACTAAGCAATCTTTA  320
        G    C   G G         T G         C

321  TCAAATTTACGCAGAATCTTTTAGAGAGTGGGAAGCAGAT  360
        C     C T        GAGC  C              C

361  CCTACTAATCCAGCATTAAGAGAAGAGATGCGTATTCAAT  400
          C      TC CC C  G  A

401  TCAATGACATGAACAGTGCCCTTACAACCGCTATTCCTCT  440
         C            C  T G C    A    C AT

441  TTTTGCAGTTCAAAATTATCAAGTTCCTCTTTTATCAGTA  480
         G C    C G C C              C G C G

481  TATGTTCAAGCTGCAAATTTACATTTATCAGTTTTGAGAG  520
         C       A  T   C T  CC CAGC  GC TC

521  ATGTTTCAGTGTTTGGACAAAGGTGGGGATTTGATGCCGC  560
        C    AGC         G              C   T

561  GACTATCAATAGTCGTTATAATGATTTAACTAGGCTTATT  600
        A C      C    C   CC T         G

601  GGCAACTATACAGATTATGCTGTACGCTGGTACAATACGG  640
        A     C  C.CC C     T T        C T
```

FIG. 10A

```
641  GATTAGAACGTGTATGGGGACCGGATTCTAGAGATTGGGT   680
       C  G  G     C       T  T              A

681  AAGGTATAATCAATTTAGAAGAGAATTAACACTAACTGTA   720
       T  A  C  C  G  C  G          G  C  C  A  T

721  TTAGATATCGTTGCTCTGTTCCCGAATTATGATAGTAGAA   760
        G  C  T  GT    C        C       CTCC

761  GATATCCAATTCGAACAGTTTCCCAATTAACAAGAGAAAT   800
       CC  C  T  C     G        C  T  C

801  TTATACAAACCCAGTATTAGAAAATTTTGATGGTAGTTTT   840
       C     T        TC T  G  C  C  C     C  C

841  CGAGGCTCGGCTCAGGGCATAGAAAGAAGTATTAGGAGTC   880
        T  T  T  C  A  T  C    G CTCC  C     C

881  CACATTTGATGGATATACTTAACAGTATAACCATCTATAC   920
         C        C  CT G    C     T     C

921  GGATGCTCATAGGGGTTATTATTATTGGTCAGGGCATCAA   960
     C        C  A  AG G      C       T  A  C  G

961  ATAATGGCTTCTCCTGTAGGGTTTTCGGGGCCAGAATTCA   1000
          C     C     A  T  A  CAGC     C  G  T

1001 CTTTTCCGCTATATGGAACTATGGGAAATGCAGCTCCACA   1040
       C   T  C                    C  C

1041 ACAACGTATTGTTGCTCAACTAGGTCAGGGCGTGTATAGA   1080
              C                       T  C  C

1081 ACATTATCGTCCACTTTATATAGAAGACCTTTTAATATAG   1120
        C  G  T     C  G  C        C  C     C

1121 GGATAAATAATCAACAACTATCTGTTCTTGACGGGACAGA   1160
       T     C  C  C  G     T  C           A

1161 ATTTGCTTATGGAACCTCCTCAAATTTGCCATCCGCTGTA   1200
       G  C  C           T  T  C              T

1201 TACAGAAAAAGCGGAACGGTAGATTCGCTGGATGAAATAC   1240
              G        C  T     CT    C     C

1241 CGCCACAGAATAACAACGTGCCACCTAGGCAAGGATTTAG   1280
        A        C  T        C              CTC

1281 TCATCGATTAAGCCATGTTTCAATGTTTCGTTCAGGCTTT   1320
      C  CA G  G     C  G  C     C        C  A  C

1321 AGTAATAGTAGTGTAAGTATAATAAGAGCTCCTATGTTCT   1360
        C  C     TCC  G  C  C  C
```

FIG. 10B

```
1361  CTTGGATACATCGTAGTGCTGAATTTAATAATATAATTGC   1400
                C             G  C  C  C  C   C

1401  ATCGGATAGTATTACTCAAATCCCTGCAGTGAAGGGAAAC   1440
                 C

1441  TTTCTTTTTAATGGTTCTGTAATTTCAGGACCAGGATTTA   1480
           C  C  C        C                  C

1481  CTGGTGGGGACTTAGTTAGATTAAATAGTAGTGGAAATAA   1520
           A   C C       C  C  C

1521  CATTCAGAATAGAGGGTATATTGAAGTTCCAATTCACTTC   1560

1561  CCATCGACATCTACCAGATATCGAGTTCGTGTACGGTATG   1600
          C                A            GA

1601  CTTCTGTAACCCCGATTCACCTCAACGTTAATTGGGGTAA   1640
                G    T

1641  TTCATCCATTTTTTCCAATACAGTACCAGCTACAGCTACG   1680
             C  C             T                C

1681  TCATTAGATAATCTACAATCAAGTGATTTTGGTTATTTTG   1720
          C  G       C        C C      C    C

1721  AAAGTGCCAATGCTTTTACATCTTCATTAGGTAATATAGT   1760
                      C C        C    C  C

1761  AGGTGTTAGAAATTTTAGTGGGACTGCAGGAGTGATAATA   1800
      G        C                         T  C

1801  GACAGATTTGAATTTATTCCAGTTACTGCAACACTCGAGG   1840
                C  G  C

1841  CTGAATATAATCTGGAAAGAGCGCAGAAGGCGGTGAATGC   1880

1881  GCTGTTTACGTCTACAAACCAACTAGGGCTAAAAACAAAT   1920
               G     C    C  C     G  C

1921  GTAACGGATTATCATATTGATCAAGTGTCCAATTTAGTTA   1960
           G                           C  G G

1961  CGTATTTATCGGATGAATTTTGTCTGGATGAAAAGCGAGA   2000
         C  CC CAGC       G  C

2001  ATTGTCCGAGAAAGTCAAACATGCGAAGCGACTCAGTGAT   2040

2041  GAACGCAATTTACTCCAAGATTCAAATTTCAAAGACATTA   2080
```

FIG.10C

```
2081  ATAGGCAACCAGAACGTGGGTGGGGCGGAAGTACAGGGAT       2120

2121  TACCATCCAAGGAGGGGATGACGTATTTAAAGAAAATTAC       2160
           G    T  C       G C  G     G  C

2161  GTCACACTATCAGGTACCTTTGATGAGTGCTATCCAACAT       2200

2201  ATTTGTATCAAAAAATCGATGAATCAAAATTAAAAGCCTT       2240
          CC C   C     G  G      C G C  G

2241  TACCCGTTATCAATTAGAGGGTATATCGAAGATAGTCAA        2280

2281  GACTTAGAAATCTATTTAATTCGCTACAATGCAAAACATG       2320
         C  C  G     CC C  C

2321  AAACAGTAAATGTGCCAGGTACGGGTTCCTTATGGCCGCT       2360

2361  TTCAGCCCAAAGTCCAATCGGAAAGTGTGGAGAGCCGAAT       2400

2401  CGATGCGCGCCACACCTTGAATGGAATCCTGACTTAGATT       2440

2441  GTTCGTGTAGGGATGGAGAAAAGTGTGCCCATCATTCGCA       2480

2481  TCATTTCTCCTTAGACATTGATGTAGGATGTACAGACTTA       2520

2521  AATGAGGACCTAGGTGTATGGGTGATCTTTAAGATTAAGA       2560

2561  CGCAAGATGGGCACGCAAGACTAGGGAATCTAGAGTTTCT       2600

2601  CGAAGAGAAACCATTAGTAGGAGAAGCGCTAGCTCGTGTG       2640

2641  AAAAGAGCGGAGAAAAAATGGAGAGACAAACGTGAAAAAT       2680
                                        G   G

2681  TGGAATGGGAAACAAATATCGTTTATAAGAGGCAAAAGA        2720
           G   C  C       C  C

2721  ATCTGTAGATGCTTTATTTGTAAACTCTCAATATGATCAA       2760

2761  TTACAAGCGGATACGAATATTGCCATGATTCATGCGGCAG       2800
```

FIG. 10D

2801 ATAAACGTGTTCATAGCATTCGAGAAGCTTATCTGCCTGA 2840

2841 GCTGTCTGTGATTCCGGGTGTCAATGCGGCTATTTTTGAA 2880

2881 GAATTAGAAGGGCGTATTTTCACTGCATTCTCCCTATATG 2920
                                    c     c

2921 ATGCGAGAAATGTCATTAAAAATGGTGATTTTAATAATGG 2960
        c     c     c g c        c c c

2961 CTTATCCTGCTGGAACGTGAAAGGGCATGTAGATGTAGAA 3000

3001 GAACAAAACAACCAACGTTCGGTCCTTGTTGTTCCGGAAT 3040

3041 GGGAAGCAGAAGTGTCACAAGAAGTTCGTGTCTGTCCGGG 3080

3081 TCGTGGCTATATCCTTCGTGTCACAGCGTACAAGGAGGGA 3120

3121 TATGGAGAAGGTTGCGTAACCATTCATGAGATCGAGAACA 3160

3161 ATACAGACGAACTGAAGTTTAGCAACTGCGTAGAAGAGGA 3200

3201 AATCTATCCAAATAACACGGTAACGTGTAATGATTATACT 3240

3241 GTAAATCAAGAAGAATACGGAGGTGCGTACACTTCTCGTA 3280

3281 ATCGAGGATATAACGAAGCTCCTTCCGTACCAGCTGATTA 3320

3321 TGCGTCAGTCTATGAAGAAAATCGTATACAGATGGACGA 3360

3361 AGAGAGAATCCTTGTGAATTTAACAGAGGGTATAGGGATT 3400

3401 ACACGCCACTACCAGTTGGTTATGTGACAAAAGAATTAGA 3440

3441 ATACTTCCCAGAAACCGATAAGGTATGGATTGAGATTGGA 3480

3481 GAAACGGAAGGAACATTTATCGTGGACAGCGTGGAATTAC 3520

3521 TCCTTATGGAGGAA 3534

FIG. 10E

```
  1  ATGGATAACAATCCGAACATCAATGAATGCATTCCTTATA   40
         C      C  A      C          A C

41  ATTGTTTAAGTAACCCTGAAGTAGAAGTATTAGGTGGAGA   80
       C  C  G     A  T     C T

81  AAGAATAGAAACTGGTTACACCCCAATCGATATTTCCTTG  120
       C C  T    C       T C     C C

121  TCGCTAACGCAATTTCTTTTGAGTGAATTTGTTCCGGTG   160
        CT G  A  G       GC C  C  G C  G  A

161  CTGGATTTGTGTTAGGACTAGTTGATATAATATGGGGAAT  200
        G  C  TC C           C  C C     T

201  TTTTGGTCCCTCTCAATGGGACGCATTTCTTGTACAAATT  240
        C         A       T    C G G

241  GAACAGTTAATTAACCAAAGAATAGAAGAATTCGCTAGGA  280
        G  G C   G G C     G    C

281  ACCAAGCCATTTCTAGATTAGAAGGACTAAGCAATCTTTA  320
        G    C      G G     T G        C

321  TCAAATTTACGCAGAATCTTTTAGAGAGTGGGAAGCAGAT  360
        C   C T       GAGC  C             C

361  CCTACTAATCCAGCATTAAGAGAAGAGATGCGTATTCAAT  400
            C    TC CC C  G  A

401  TCAATGACATGAACAGTGCCCTTACAACCGCTATTCCTCT  440
        C          C   T G  C     C   AT

441  TTTTGCAGTTCAAAATTATCAAGTTCCTCTTTTATCAGTA  480
        G C    C G C C            C G C  G

481  TATGTTCAAGCTGCAAATTTACATTTATCAGTTTTGAGAG  520
        C       A T   C T  CC CAGC  GC TC

521  ATGTTTCAGTGTTTGGACAAAGGTGGGGATTTGATGCCGC  560
        C  AGC      G            C    T

561  GACTATCAATAGTCGTTATAATGATTTAACTAGGCTTATT  600
        A C    C        C C CC T          G

601  GGCAACTATACAGATTATGCTGTACGCTGGTACAATACGG  640
          A    C  C  CC C    T T     C T

641  GATTAGAACGTGTATGGGGACCGGATTCTAGAGATTGGGT  680
        C  G  G    C      T T               A
```

FIG. 11A

```
681  AAGGTATAATCAATTTAGAAGAGAATTAACACTAACTGTA  720
     T  A  C   C  G C G        G   C  C  A T

721  TTAGATATCGTTGCTCTGTTCCGAATTATGATAGTAGAA  760
       G  C  T  GT    C        C      CTCC

761  GATATCCAATTCGAACAGTTTCCCAATTAACAAGAGAAAT  800
       CC  C  T  C  T     G       C T C

801  TTATACAAACCCAGTATTAGAAAATTTTGATGGTAGTTTT  840
        C    T         TC T G  C C C      C C

841  CGAGGCTCGGCTCAGGGCATAGAAGAAGTATTAGGAGTC  880
        T  T  T  C  A T C    G CTCC  C     C

881  CACATTTGATGGATATACTTAACAGTATAACCATCTATAC  920
         C       C   CT G     C     T     C

921  GGATGCTCATAGGGGTTATTATTATTGGTCAGGGCATCAA  960
     C         C  A  AG G       C     T A C G

961  ATAATGGCTTCTCCTGTAGGGTTTTCGGGGCCAGAATTCA  1000
        C    C       A T A  CAGC     C  G  T

1001 CTTTTCCGCTATATGGAACTATGGGAAATGCAGCTCCACA  1040
         C  T  C                    C  C

1041 ACAACGTATTGTTGCTCAACTAGGTCAGGGCGTGTATAGA  1080
             C                      T C  C

1081 ACATTATCGTCCACTTTATATAGAAGACCTTTTAATATAG  1120
          C G T    C G C       C C     C

1121 GGATAAATAATCAACAACTATCTGTTCTTGACGGGACAGA  1160
         T  C  C  C G     T  C         A

1161 ATTTGCTTATGGAACCTCCTCAAATTTGCCATCCGCTGTA  1200
      G  C  C         T  T C              T

1201 TACAGAAAAAGCGGAACGGTAGATTCGCTGGATGAAATAC  1240
                G    C  T    CT    C     C

1241 CGCCACAGAATAACAACGTGCCACCTAGGCAAGGATTTAG  1280
        A       C     T        C         CTC

1281 TCATCGATTAAGCCATGTTTCAATGTTTCGTTCAGGCTTT  1320
       C  CA G  G     C G C     C      C A C

1321 AGTAATAGTAGTGTAAGTATAATAAGAGCTCCTATGTTCT  1360
        C   C   TCC  G  C  C  C

1361 CTTGGATACATCGTAGTGCTGAATTTAATAATATAATTGC  1400
          C              G  C    C  C  C  C
```

FIG. 11B

```
1401  ATCGGATAGTATTACTCAAATCCCTGCAGTGAAGGGAAAC  1440
            C

1441  TTTCTTTTAATGGTTCTGTAATTTCAGGACCAGGATTTA  1480
         C  C  C         C                    C

1481  CTGGTGGGGACTTAGTTAGATTAAATAGTAGTGGAAATAA  1520
            A  C C      C C  C C

1521  CATTCAGAATAGAGGGTATATTGAAGTTCCAATTCACTTC  1560

1561  CCATCGACATCTACCAGATATCGAGTTCGTGTACGGTATG  1600
          C              A           GA

1601  CTTCTGTAACCCCGATTCACCTCAACGTTAATTGGGGTAA  1640
            G    T

1641  TTCATCCATTTTTTCCAATACAGTACCAGCTACAGCTACG  1680
           C C           T                   C

1681  TCATTAGATAATCTACAATCAAGTGATTTGGTTATTTTG  1720
        C  G       C    C C    C    C

1721  AAAGTGCCAATGCTTTTACATCTTCATTAGGTAATATAGT  1760
                    C C        C C

1761  AGGTGTTAGAAATTTTAGTGGGACTGCAGGAGTGATAATA  1800
        G        C                       T C

1801  GACAGATTTGAATTTATTCCAGTTACTGCAACACTCGAGG  1840
           C  G  C

1841  CTGAATATAATCTGGAAAGAGCGCAGAAGGCGGTGAATGC  1880
         G   C C T G    C       T   C

1881  GCTGTTTACGTCTACAAACCAACTAGGGCTAAAAACAAAT  1920
      C C       C   C C TG T  CT G      T  C

1921  GTAACGGATTATCATATTGATCAAGTGTCCAATTTAGTTA  1960
         T  T C    C       C            C G C

1961  CGTATTTATCGGATGAATTTTGTCTGGATGAAAAGCGAGA  2000
         C  CC TAGC     G  C  C  C G      T

2001  ATTGTCCGAGAAAGTCAAACATGCGAAGCGACTCAGTGAT  2040
       C C           T   C C   T    C C

2041  GAACGCAATTTACTCCAAGATTCAAATTTCAAAGACATTA  2080
       GA G   C CT G    C   C C              C

2081  ATAGGCAACCAGAACGTGGGTGGGCGGAAGTACAGGGAT  2120
         C    G         T  T    C C
```

FIG. 11C

| | | |
|---|---|---|
| 2121 | TACCATCCAAGGAGGGGATGACGTATTTAAAGAAAATTAC<br>C                C C T     G C G G C | 2160 |
| 2161 | GTCACACTATCAGGTACCTTTGATGAGTGCTATCCAACAT<br>   C  C  C   A T C C           C T C | 2200 |
| 2201 | ATTTGTATCAAAAAATCGATGAATCAAAATTAAAAGCCTT<br> C       C    G G         G   C C C | 2240 |
| 2241 | TACCCGTTATCAATTAAGAGGGTATATCGAAGATAGTCAA<br>C  A G      C T     C C       C C | 2280 |
| 2281 | GACTTAGAAATCTATTTAATTCGCTACAATGCAAAACATG<br>C T         C CG  CA G      C G C | 2320 |
| 2321 | AAACAGTAAATGTGCCAGGTACGGGTTCCTTATGGCCGCT<br>G  C  G    C       T      C C     A | 2360 |
| 2361 | TTCAGCCCAAAGTCCAATCGGAAAGTGTGGAGAGCCGAAT<br> T     TC    C  T   G           T C | 2400 |
| 2401 | CGATGCGCGCCACACCTTGAATGGAATCCTGACTTAGATT<br>A  T         G                G C | 2440 |
| 2441 | GTTCGTGTAGGGATGGAGAAAAGTGTGCCCATCATTCGCA<br>C  C  C      C G       C     T | 2480 |
| 2481 | TCATTTCTCCTTAGACATTGATGTAGGATGTACAGACTTA<br> C      G  C    G      T  C G | 2520 |
| 2521 | AATGAGGACCTAGGTGTATGGGTGATCTTTAAGATTAAGA<br>   C A C     C     C     C | 2560 |
| 2561 | CGCAAGATGGGCACGCAAGACTAGGGAATCTAGAGTTTCT<br> C   C  A         T C C T | 2600 |
| 2601 | CGAAGAGAAACCATTAGTAGGAGAAGCGCTAGCTCGTGTG<br>          G  C T     T ·C | 2640 |
| 2641 | AAAAGAGCGGAGAAAAAATGGAGAGACAAACGTGAAAAAT<br>    G   A    G G     G        G  C | 2680 |
| 2681 | TGGAATGGGAAACAAATATCGTTTATAAGAGGCAAAAGA<br> C       T  C      C G   C | 2720 |
| 2721 | ATCTGTAGATGCTTTATTTGTAAACTCTCAATATGATCAA<br>G C G       G C G    C           G | 2760 |
| 2761 | TTACAAGCGGATACGAATATTGCCATGATTCATGCGGCAG<br>  G    C C C C C       C C C | 2800 |
| 2801 | ATAAACGTGTTCATAGCATTCGAGAAGCTTATCTGCCTGA<br>  C      G C    T  G   CT | 2840 |

FIG. 11D

```
2841  GCTGTCTGTGATTCCGGGTGTCAATGCGGCTATTTTGAA   2880
         T  C     C  T     G  C T  C  C  G

2881  GAATTAGAAGGGCGTATTTTCACTGCATTCTCCTATATG   2920
        C T  G  A     C T  C        T G  C

2921  ATGCGAGAAATGTCATTAAAAATGGTGATTTTAATAATGG  2960
         C        C    C G C      C C C

2961  CTTATCCTGCTGGAACGTGAAAGGGCATGTAGATGTAGAA  3000
       C CAG       T       T      G C G  G

3001  GAACAAAACAACCAACGTTCGGTCCTTGTTGTTCCGGAAT  3040
          G    T  G     C      G    G T  G

3041  GGGAAGCAGAAGTGTCACAAGAAGTTCGTGTCTGTCCGGG  3080
           T       C    G    A A        A

3081  TCGTGGCTATATCCTTCGTGTCACAGCGTACAAGGAGGGA  3120
       A A      C T C      G  C T

3121  TATGGAGAAGGTTGCGTAACCATTCATGAGATCGAGAACA  3160
         C  T  G       G      C C

3161  ATACAGACGAACTGAAGTTTAGCAACTGCGTAGAAGAGGA  3200
        C  C    G  T     CTC       C  G  A

3201  AATCTATCCAAATAACACGGTAACGTGTAATGATTATACT  3240
           C  C     C T T C C C  C

3241  GTAAATCAAGAAGAATACGGAGGTGCGTACACTTCTCGTA  3280
         G    G   G        C      AGC

3281  ATCGAGGATATAACGAAGCTCCTTCCGTACCAGCTGATTA  3320
       CA   T  C              T T       C

3321  TGCGTCAGTCTATGAAGAAAAATCGTATACAGATGGACGA  3360
         C  C G C  G G     C C           CA

3361  AGAGAGAATCCTTGTGAATTTAACAGAGGGTATAGGGATT  3400
       C T    C       C G C       T C     C

3401  ACACGCCACTACCAGTTGGTTATGTGACAAAAGAATTAGA  3440
          A    T    C       T  C G GC T

3441  ATACTTCCCAGAAACCGATAAGGTATGGATTGAGATTGGA  3480
         G   T  T G    C A  G       C  C T

3481  GAAACGGAAGGAACATTTATCGTGGACAGCGTGGAATTAC  3520
           C   G    C  C              GC T

3521  TCCTTATGGAGGAA  3534
         T G
```

FIG. 11E

```
  1  ATGACTGCAGATAATAATACGGAAGCACTAGATAGCTCTA   40
         C   C   C  C         C   C  C    T

41  CAACAAAAGATGTCATTCAAAAGGCATTTCCGTAGTAGG    80
       C  T G       T C  G GT C       T  G

81  TGATCTCCTAGGCGTAGTAGGTTTCCCGTTTGGTGGAGCG  120
       A   C    T G    G T A  T CC         C

121  CTTGTTTCGTTTTATACAAACTTTTAAATACTATTTGGC   160
       C  GAGC C                C   C  C  C

161  CAAGTGAAGACCCGTGGAAGGCTTTTATGGAACAAGTAGA  200
         C    G   T      A A C     G    T

201  AGCATTGATGGATCAGAAAATAGCTGATTATGCAAAAAAT  240
         TC T           G T A       C G C

241  AAAGCTCTTGCAGAGTTACAGGGCCTTCAAAATAATGTCG  280
        G   T  G      AC C        G  C    G

281  AAGATTATGTGAGTGCATTGAGTTCATGGCAAAAAAATCC  320
       G  C  C          TCCAGC     G  G  C

321  TGTGAGTTCACGAAATCCACATAGCCAGGGGCGGATAAGA  360
          T   C  CA       T    C     A TA  C

361  GAGCTGTTTTCTCAAGCAGAAAGTCATTTTCGTAATTCAA  400
          T    C       C   TCC C  CA A     C

401  TGCCTTCGTTTGCAATTTCTGGATACGAGGTTCTATTTCT  440
          AGC       T  C   T            T C

441  AACAACATATGCACAAGCTGCCAACACACATTTATTTTTA  480
       C   T  C    T            C C  G   CC

481  CTAAAAGACGCTCAAATTTATGGAGAAGAATGGGGATACG  520
        T   G       C                  G

521  AAAAAGAAGATATTGCTGAATTTTATAAAAGACAACTAAA  560
         G     G  C     G  C    C  GC T    T

561  ACTTACGCAAGAATATACTGACCATTGTGTCAAATGGTAT  600
       G  C  C    G  C           C  G

601  AATGTTGGATTAGATAAATTAAGAGGTTCATCTTATGAAT  640
         C    TC C     GC C     C  T  C  G

641  CTTGGGTAAACTTTAACCGTTATCGCAGAGAGATGACATT  680
         G    C   A A  CA G              C
```

FIG. 12A

```
681  AACAGTATTAGATTTAATTGCACTATTTCCATTGTATGAT       720
       G T  GC C    C T C        C      C    C

721  GTTCGGCTATACCCAAAAGAAGTTAAAACCGAATTAACAA       760
      GA A   C          G     G    T GC T  C

761  GAGACGTTTTAACAGATCCAATTGTCGGAGTCAACAACCT       800
          GC C    T    C  T

801  TAGGGGCTATGGAACAACCTTCTCTAATATAGAAAATTAT       840
         T     T       AGC      C       C C

841  ATTCGAAAACCACATCTATTTGACTATCTGCATAGAATTC       880
       A G             C C       T  C

881  AATTTCACACGCGGTTCCAACCAGGATATTATGGAAATGA       920
          C   AA   T          C      T C

921  CTCTTTCAATTATTGGTCCGGTAATTATGTTTCAACTAGA       960
          C   C          C         C C

961  CCAAGCATAGGATCAAATGATATAATCACATCTCCATTCT      1000
          T      T       C C              C

1001 ATGGAAATAAATCCAGTGAACCTGTACAAAATTTAGAATT      1040
       T  C G               G  GCC T G

1041 TAATGGAGAAAAAGTCTATAGAGCCGTAGCAAATACAAAT      1080
      C  C C   G              C      C C

1081 CTTGCGGTCTGGCCGTCCGCTGTATATTCAGGTGTTACAA      1120
          C T  G    A    A T C    C C

1121 AAGTGGAATTTAGCCAATATAATGATCAAACAGATGAAGC      1160
        G    G    T  G      C    G C     G

1161 AAGTACACAAACGTACGACTCAAAAAGAAATGTTGGCGCG      1200
      C  C  C G T       C   CT C            A

1201 GTCAGCTGGGATTCTATCGATCAATTGCCTCCAGAAACAA      1240
         TCT           C              C

1241 CAGATGAACCTCTAGAAAAGGGATATAGCCATCAACTCAA      1280
         C    AT G         C C     C    T

1281 TTATGTAATGTGCTTTTAATGCAGGGTAGTAGAGGAACA       1320
       C     G        C G   A  TCC     G C

1321 ATCCCAGTGTTAACTTGGACACATAAAAGTGTAGACTTTT      1360
         T     G  C       C   GTCC G      C

1361 TTAACATGATTGATTCGAAAAAAATTACACAACTTCCGTT      1400
        C       C   AGC G   G  C          C
```

FIG.12B

1401 AGTAAAGGCATATAAGTTACAATCTGGTGCTTCCGTTGTC 1440
     G  G  A  C  C     C G

1441 GCAGGTCCTAGGTTTACAGGAGGAGATATCATTCAATGCA 1480
         C  A  C  T     T  C     C  G

1481 CAGAAAATGGAAGTGCGGCAACTATTTACGTTACACCGGA 1520
        G  C  C  A  T     C     G     T

1521 TGTGTCGTACTCTCAAAAATATCGAGCTAGAATTCATTAT 1560
         T        G  G  CA G  AC T        C

1561 GCTTCTACATCTCAGATAACATTTACACTCAGTTTAGACG 1600
        A     CAGC     C  C  C        C G  T

1601 GGGCACCATTTAATCAATACTATTTCGATAAAACGATAAA 1640
        A     C  C  C  G  T  C  T  C  G  C  C

1641 TAAAGGAGACACATTAACGTATAATTCATTTAATTTAGCA 1680
     C    T     TC C  A  C    AGC  C  C  G

1681 AGTTTCAGCACACCATTCGAATTATCAGGGAATAACTTAC 1720
                T     C  C        C  C  TC T

1721 AAATAGGCGTCACAGGATTAAGTGCTGGAGATAAAGTTTA 1760
        G  C        C  TC C  C     C     C

1761 TATAGACAAAATTGAATTTATTCCAGTGAAT 1791
        C  C     G     G  C  C     C

FIG.12C

```
  1   ATG   AATAATGTATTGAATAGTGGAAGAACAACTATTT       40
        GAC   C   C    CTC    T         C  C

41   GTGATGCGTATAATGTAGTAGCCCATGATCCATTTAGTTT      80
         C  C  A  C  C  C  G  T  C       C  C

81   TGAACATAAATCATTAGATACCATCCAAAAAGAATGGATG     120
         C    C  GAGCC   C   C  T    T  G  G

121   GAGTGGAAAAGAACAGATCATAGTTTATATGTAGCTCCTG     160
          A      C  T  T  C  CTC  C   C  C  A

161   TAGTCGGAACTGTGTCTAGTTTTTTGCTAAAGAAAGTGGG     200
         G  T     A     C  C  CC T  C     G  C

201   GAGTCTTATTGGAAAAAGGATATTGAGTGAATTATGGGGG     240
        CTC    C  C       C  T  C   TCC  C C   T

241   ATAATATTTCCTAGTGGTAGTACAAATCTAATGCAAGATA     280
         C  C     ATC    GTCC  T     C       C

281   TTTTAAGGGAGACAGAACAATTCCTAAATCAAAGACTTAA     320
         C  G      C       G  T  C  C  GC T  C

321   TACAGATACCCTTGCTCGTGTAAATGCAGAATTGATAGGG     360
         C  T     TG   AA  C  C  T  G      C  T

361   CTCCAAGCGAATATAAGGGAGTTTAATCAACAAGTAGATA     400
              A  C   TC T     C  C  G      G  C

401   ATTTTTTAAACCCTACTCAAAACCCTGTTCCTTTATCAAT     440
         C   C  G  T  A      G  T     G  CT C

441   AACTTCTTCGGTTAATACAATGCAGCAATTATTTCTAAAT     480
         C       C  G  C  T         C  C  C  C

481   AGATTACCCCAGTTCCAGATACAAGGATACCAGTTGTTAT     520
              G  T    T    T    C           C CC

521   TATTACCTTTATTTGCACAGGCAGCCAATATGCATCTTTC     560
        TC T  AC C     T     T     C       CT G

561   TTTTATTAGAGATGTTATTCTTAATGCAGATGAATGGGGT     600
         C  C  AC T  C  G  CCC  T  C           A

601   ATTTCAGCAGCAACATTACGTACGTATCGAGATTACCTGA     640
         C  T     C  TC TA G  A  CA    C    T

641   GAAATTATACAAGAGATTATTCTAATTATTGTATAAATAC     680
         G  C  C   TC T    C   C  C    C  C  C
```

FIG.13A

```
681  GTATCAAACTGCGTTTAGAGGGTTAAACACCCGTTTACAC  720
        T  G    C   C T  AC C   T  TA GC T

721  GATATGTTAGAATTTAGAACATATATGTTTTTAAATGTAT  760
       C   C T G  C G  C C     CC T  C G

761  TTGAATATGTATCCATTTGGTCATTGTTTAAATATCAGAG  800
        G  C  CAG      AGTC  C  C  G C

801  TCTTATGGTATCTTCTGGCGCTAATTTATATGCTAGCGGT  840
     CT G    G  C    A    C   C C  CTCT  C

841  AGTGGACCACAGCAGACACAATCATTTACAGCACAAAACT  880
              A  T   GAGC  C       T  G

881  GGCCATTTTTATATTCTCTTTTCCAAGTTAATTCGAATTA  920
          C  G  AGCT G         C  C C

921  TATATTATCTGGTATTAGTGGTACTAGGCTTTCTATTACC  960
       C  TC CAG    CTC  G  A  C  C  A

961  TTCCCTAATATTGGTGGTTTACCGGGTAGTACTACAACTC  1000
         T  C  C      AC T  A  CTCC       C

1001 ATTCATTGAATAGTGCCAGGGTTAATTATAGCGGAGGAGT  1040
       AGCC T  CTC      A  G  C C T    T

1041 TTCATCTGGTCTCATAGGGGCGACTAATCTCAATCACAAC  1080
     CAGC     AT G  T  T A    CT G  C

1081 TTTAATTGCAGCACGGTCCTCCCTCCTTTATCAACACCAT  1120
        C     TC  C    T G  A  C GAGC    G

1121 TTGTTAGAAGTTGGCTGGATTCAGGTACAGATCGAGAGGG  1160
        G   GTCC     T   CAGC    T    C  A

1161 CGTTGCTACCTCTACGAATTGGCAGACAGAATCCTTTCAA  1200
      A          A  C    A C G        C

1201 ACAACTTTAAGTTTAAGGTGTGGTGCTTTTTCAGCCCGTG  1240
       C   C T  CC TC     A    C T  A

1241 GAAATTCAAACTATTTCCCAGATTATTTTATCCGTAATAT  1280
       G        C T    C   C  C  TA G  C

1281 TTCTGGGGTTCCTTTAGTTATTAGAAACGAAGATCTAACA  1320
       C    T      C  C C C  GT     C  C C

1321 AGACCGTTACACTATAACCAAATAAGAAATATAGAAAGTC  1360
       C T  AC T  T C    G TG  C  C  GTC

1361 CTTCGGGAACACCTGGTGGAGCACGGGCCTATTTGGTATC  1400
        A  C   T T  AA  T   AA T  CC C  G
```

FIG.13B

```
1401  TGTGCATAACAGAAAAAATAATATCTATGCCGCTAATGAA   1440
         C       G  G  C  C       C T  C  C G

1441  AATGGTACTATGATCCATTTGGCGCCAGAAGATTATACAG   1480
         C  C      T  CC T  A              C T

1481  GATTTACTATATCGCCAATACATGCCACTCAAGTGAATAA   1520
         C     C  C T     C      T C       C

1521  TCAAACTCGAACATTTATTTCTGAAAAATTTGGAAATCAA   1560
         G   A  C     C  C  C      G C

1561  GGTGATTCCTTAAGATTTGAACAAAGCAACACGACAGCTC   1600
            C       G   G  C  G   TC     T  C  A

1601  GTTATACGCTTAGAGGGAATGGAAATAGTTACAATCTTTA   1640
         G  C  TT G        C        C  C     C

1641  TTTAAGAGTATCTTCAATAGGAAATTCAACTATTCGAGTT   1680
         C  G       TAGC  C  T  T C  C   C  T

1681  ACTATAAACGGTAGAGTTTATACTGTTTCAAATGTTAATA   1720
         C  C     AC T     C  A  C  T     G  C

1721  CCACTACAAATAACGATGGAGTTAATGATAATGGAGCTCG   1760
         T  A  G  C  T     C        C  C    CA

1761  TTTTTCAGATATTAATATCGGTAATATAGTAGCAAGTGAT   1800
         A  CAGC  C  C  T  C  C  C G  CTC    C

1801  AATACTAATGTAACGCTAGATATAAATGTGACATTAAACT   1840
         C     C  T  TT G  C  C         CC C  T

1841  CCGGTACTCCATTTGATCTCATGAATATTATGTTTGTGCC   1880
         T  A                       C  C

1881  AACTAATCTTCCACCACTTTAT   1902
         C  C  T    T G  C
```

FIG. 13C

```
  1  ATGGAGGAAAATAATCAAAATCAATGCATACCTTACAATT   40
        G  CC    C          T  A     C

41  GTTTAAGTAATCCTGAAGAAGTACTTTTGGATGGAGAACG   80
      C G   C  A      G   T GC T

81  GATATCAACTGGTAATTCATCAATTGATATTTCTCTGTCA  120
     C T    C     C T C  C C  CT     C

121  CTTGTTCAGTTTCTGGTATCTAACTTTGTACCAGGGGGAG  160
     T G  C         CAGC    C G     T  T

161  GATTTTTAGTTGGATTAATAGATTTTGTATGGGGAATAGT  200
     G  CC T  C      C    T C C C       T C

201  TGGCCCTTCTCAATGGGATGCATTTCTAGTACAAATTGAA  240
        T  A                C G G        G

241  CAATTAATTAATGAAAGAATAGCTGAATTTGCTAGGAATG  280
      G  G  C  G G C      G  C  C    C

281  CTGCTATTGCTAATTTAGAAGGATTAGGAAACAATTTCAA  320
      C C    C G            G C T C

321  TATATATGTGGAAGCATTTAAAGAATGGGAAGAAGATCCT  360
     C  C      G  C  C     G         G  C

361  AATAATCCAGAAACCAGGACCAGAGTAATTGATCGCTTTC  400
            C  G   C T G  C   CA A  CA

401  GTATACTTGATGGGCTACTTGAAAGGGACATTCCTTCGTT  440
      A  CT G  C  C    CT G  G  A  T  C  A C

441  TCGAATTTCTGGATTTGAAGTACCCCTTTTATCCGTTTAT  480
     CA    C      C  C      T T C      G  C

481  GCTCAAGCGGCCAATCTGCATCTAGCTATATTAAGAGATT  520
           A T    T  C C      CC TC    CA

521  CTGTAATTTTTGGAGAAAGATGGGGATTGACAACGATAAA  560
     G   C  C    G       G         C T  C

561  TGTCAATGAAAACTATAATAGACTAATTAGGCATATTGAT  600
     C       G T  C  C    T C     C    C

601  GAATATGCTGATCACTGTGCAAATACGTATAATCGGGGAT  640
      G  C C  C        T C  C C T C

641  TAAATAATTTACCGAAATCTACGTATCAAGATTGGATAAC  680
       G  C   CC  T G    T              T

681  ATATAATCGATTACGGAGAGACTTAACATTGACTGTATTA  720
       C  C  CA G  GA      G  CC  A T G
```

FIG. 14A

```
 721  GATATCGCCGCTTTCTTTCCAAACTATGACAATAGGAGAT   760
        C  T  A         C  G            C

761  ATCCAATTCAGCCAGTTGGTCAACTAACAAGGGAAGTTTA   800
        C  T  C A     G       T  C  A      C

801  TACGGACCCATTAATTAATTTTAATCCACAGTTACAGTCT   840
         T      C T     C  C C  T     G AAG

841  GTAGCTCAATTACCTACTTTTAACGTTATGGAGAGCAGCC   880
        C  C   C T  A  C      C        TC

881  GAATTAGAAATCCTCATTTATTTGATATATTGAATAATCT   920
        T  C  G  C  A C  G      C C       C C

921  TACAATCTTTACGGATTGGTTTAGTGTTGGACGCAATTTT   960
          T    C C       C  C        G  T C  C

961  TATTGGGGAGGACATCGAGTAATATCTAGCCTTATAGGAG  1000
         T         CA G  C  C    CTCT    T

1001  GTGGTAACATAACATCTCCTATATATGGAAGAGAGGCGAA  1040
         G     T C        C       C T     A

1041  CCAGGAGCCTCCAAGATCCTTTACTTTTAATGGACCGGTA  1080
             A   C TAGT  C  C  C  T  A  C

1081  TTTAGGACTTTATCAAATCCTACTTTACGATTATTACAGC  1120
         C  A  C  G T  C    C GA    GC C

1121  AACCTTGGCCAGCGCCACCATTTAATTTACGTGGTGTTGA  1160
              T     T  C  CC TA A

1161  AGGAGTAGAATTTTCTACACCTACAAATAGCTTTACGTAT  1200
        G  C T  G C       T    C  CTC   C T C

1201  CGAGGAAGAGGTACGGTTGATTCTTTAACTGAATTACCGC  1240
        A     T  A  C         C G  C    CC  A

1241  CTGAGGATAATAGTGTGCCACCTCGCGAAGGATATAGTCA  1280
        A    C     C         CA G    C  CTCC

1281  TCGTTTATGTCATGCAACTTTTGTTCAAAGATCTGGAACA  1320
      CA G  G  C  C      C  C G GC T  C      T

1321  CCTTTTTTAACAACTGGTGTAGTATTTTCTTGGACCGATC  1360
          A  CC C  T  A  A T  G  C  A      T

1361  GTAGTGCAACTCTTACAAATACAATTGATCCAGAGAGAAT  1400
         T    C  T   C       C   C  G
```

FIG.14B

```
1401  TAATCAAATACCTTTAGTGAAAGGATTTAGAGTTTGGGGG  1440
         C        C   A  G  C  G  T  CC T  G       A

1441  GGCACCTCTGTCATTACAGGACCAGGATTTACAGGAGGGG  1480
        A T       C                 C  C       T

1481  ATATCCTTCGAAGAAATACCTTTGGTGATTTTGTATCTCT  1520
         T    A      C  T     C  C       GAGC

1521  ACAAGTCAATATTAATTCACCAATTACCCAAAGATACCGT  1560
        C    T   C  C T        T        T

1561  TTAAGATTTCGTTACGCTTCCAGTAGGGATGCACGAGTTA  1600
        C  C   G          A   TTCCC T  C  TA    C

1601  TAGTATTAACAGGAGCGGCATCCACAGGAGTGGGAGGCCA  1640
         C  GC C   C  C  A  T  T  C  T  C  T  A

1641  AGTTAGTGTAAATATGCCTCTTCAGAAAACTATGGAAATA  1680
         CTCC  G   C    A  C       G        G  C

1681  GGGGAGAACTTAACATCTAGAACATTTAGATATACCGATT  1720
          C        G    C G C C       C       C

1721  TTAGTAATCCTTTTTCATTTAGAGCTAATCCAGATATAAT  1760
        CTC   C      CAGT CC T  C  C T  C  C

1761  TGGGATAAGTGAACAACCTCTATTTGGTGCAGGTTCTATT  1800
          C  T   C         C       A  T   AGC C

1801  AGTAGCGGTGAACTTTATATAGATAAAATTGAAATTATTC  1840
        TCATCT  C   T G C  T C G      G C

1841  TAGCAGATGCAACATTTGAAGCAGAATCTGATTTAGAAAG  1880
         T  C   C  T   CC C  G  T  ACA CC T  G

1881  AGCACAAAAGGCGGTGAATGCCCTGTTTACTTCTTCCAAT  1920
         C     G    T     C      C     C CA

1921  CAAATCGGGTTAAAAACCGATGTGACGGATTATCATATTG  1960
         GC T  C  G       TA C  T  T  C      C

1961  ATCAAGTATCCAATTTAGTGGATTGTTTATCAGATGAATT  2000
         C     G    C  G  CACC  ACC  TAGC    G

2001  TTGTCTGGATGAAAAGCGAGAATTGTCCGAGAAAGTCAAA  2040
        C   C     C  C  G    T  CC          T

2041  CATGCGAAGCGACTCAGTGATGAGCGGAATTTACTTCAAG  2080
         C     C    T    C C   A      C CT G

2081  ATCCAAACTTCAGAGGGATCAATAGACAACCAGACCGTGG  2120
        CT C       A  AC      C  G  G     A
```

FIG. 14C

```
2121  CTGGAGAGGAAGTACAGATATTACCATCCAAGGAGGAGAT    2160
        T   G T    C  C GG  C                C  C

2161  GACGTATTCAAAGAGAATTACGTCACACTACCGGGTACCG    2200
         T  G     G     C     C CT C  A   TT

2201  TTGATGAGTGCTATCCAACGTATTTATATCAGAAAATAGA    2240
        C  C        C T  C G C          G C

2241  TGAGTCGAAATTAAAAGCTTATACCCGTTATGAATTAAGA    2280
         C  C C        C TC   A G    C C T

2281  GGGTATATCGAAGATAGTCAAGACTTAGAAATCTATTTGA    2320
         C  C      C C     C T        C  C

2321  TCCGTTACAATGCAAAACACGAAATAGTAAATGTGCCAGG    2360
         A  G       C G    G  GCC G       C

2361  CACGGGTTCCTTATGGCCGCTTTCAGCCCAAATGCCAATC    2400
        T T     C C   A    T       TCT C  T

2401  GGAAAGTGTGGAGAACCGAATCGATGCGCGCCACACCTTG    2440
         G          G  T  CA    T

2441  AATGGAATCCTGATCTAGATTGTTCCTGCAGAGACGGGGA    2480
         G          CT G  C  C        G  T  C

2481  AAAATGTGCACATCATTCCCATCATTTCACCTTGGATATT    2520
        G G      C C     T    C T          C C

2521  GATGTTGGATGTACAGACTTAAATGAGGACTTAGGTGTAT    2560
         G       T  C G        C C  A  C

2561  GGGTGATATTCAAGATTAAGACGCAAGATGGCCATGCAAG    2600
         C C       C        C     C    A  C

2601  ACTAGGGAATCTAGAGTTTCTCGAAGAGAAACCATTATTA    2640
         T  C  C T                       GG C

2641  GGGGAAGCACTAGCTCGTGTGAAAAGAGCGGAGAAGAAGT    2680
         T  T C            G    A

2681  GGAGAGACAAACGAGAGAAACTGCAGTTGGAAACAAATAT    2720
         G      T        CG A G       T  C

2721  TGTTTATAAAGAGGCAAAAGAATCTGTAGATGCTTTATTT    2760
        C   C G     C      G C G        G  C

2761  GTAAACTCTCAATATGATAGATTACAAGTGGATACGAACA    2800
         G    C        CAG  G   CC  C  C

2801  TCGCCATGATTCATGCGGCAGATAAACGCGTTCATAGAAT    2840
         C  C        C       T  G C  C
```

FIG. 14D

```
2841  CCGGGAAGCGTATCTGCCAGAGTTGTCTGTGATTCCAGGT                    2880
        T  T G T CT    T         C     C T
2881  GTCAATGCGGCCATTTTCGAAGAATTAGAGGGACGTATTT                    2920
        G  C T      C       G  C T             C
2921  TTACAGCGTATTCCTTATATGATGCGAGAAATGTCATTAA                    2960
         C  A TC     G  C      C         C
2961  AAATGGCGATTTCAATAATGGCTTATTATGCTGGAACGTG                    3000
      G  C T C      C       C CAGC           T
3001  AAAGGTCATGTAGATGTAGAAGAGCAAAACAACCACCGTT                    3040
              G  C  G  G  A  G     T  G
3041  CGGTCCTTGTTATCCCAGAATGGGAGGCAGAAGTGTCACA                    3080
         C     G    GG T G   A T              C
3081  AGAGGTTCGTGTCTGTCCAGGTCGTGGCTATATCCTTCGT                    3120
           A A              A A      C T C
3121  GTCACAGCATATAAAGAGGGATATGGAGAGGGCTGCGTAA                    3160
         G  C T C G       C T     T        G
3161  CGATCCATGAGATCGAAGACAATACAGACGAACTGAAATT                    3200
         C  C         GA   C C     G T G
3201  CAGCAACTGTGTAGAAGAGGAAGTATATCCAAACAACACA                    3240
        TC      C C G A  A C          C         C
3241  GTAACGTGTAATAATTATACTGGGACTCAAGAAGAATATG                    3280
         T T  C  CG C C    T  A G    G C
3281  AGGGTACGTACACTTCTCGTAATCAAGGATATGACGAAGC                    3320
      GA   G C      AGC    CAG   T  CA
3321  CTATGGTAATAACCCTTCCGTACCAGCTGATTACGCTTCA                    3360
      TCC TCXXXXXXXXXXXX   T  T    C T C  C
3361  GTCTATGAAGAAAATCGTATACAGATGGACGAAGAGAGA                     3400
       G  C G G     C C        CA  C T
3401  ATCCTTGTGAATCTAACAGAGGCTATGGGGATTACACACC                    3440
        C   C G TC       T CA    C
3441  ACTACCGGCTGGTTATGTAACAAAGGATTTAGAGTACTTC                    3480
         T  A T  C    T C     GC T              T
3481  CCAGAGACCGATAAGGTATGGATTGAGATCGGAGAAACAG                    3520
       T         C A G       C       T     C
3521  AAGGAACATTCATCGTGGATAGCGTGGAATTACTCCTTAT                    3560
         G   C         C          GC T   T G

3561  GGAGGAA  3567
```

FIG.14E

```
  1  AGATCTAGAGGTAATTGTTATGAGTACTGTCGTGGTTAAG   40
                   GATC

41  GGAAACGTCAACGGTGGTGTACAACAACCTAGAAGGAGGA   80
              G      T              A

81  GAAGGCAATCCCTTCGCAGGAGGGCTAACAGAGTACAGCC  120
              T      A            T

121  AGTGGTTATGGTCACTGCTCCTGGCGAACCCAGGAGGAGG  160
                            GC   A   A     A

161  AGACGCAGAAGAGGAGGCAATCGCAGGTCAAGAAGAACTG  200
       A G         T         A

201  GAGTTCCCAGGGGAAGGGGCTCAAGCGAGACATTCGTGTT  240
              A      A T

241  TACAAAGGACAACCTCGTGGGCAACTCCCAAGGAAGTTTC  280

281  ACCTTCGGACCAAGTGTATCAGACTGTCCAGCATTCAAGG  320
             T

321  ATGGAATACTCAAGGCCTACCATGAGTACAAGATCACAAG  360
              T

361  TATCCTTCTTCAGTTCGTCAGCGAGGCCTCTTCCACCTCA  400
        T G                                T

401  CCAGGATCCATCGCTTATGAGTTGGACCCACATTGCAAAG  440
           C              A T

441  TATCATCCCTCCAGTCCTACGTCAACAAGTTCCAAATCAC  480
        T

481  AAAGGGAGGAGCTAAGACCTATCAAGCTAGGATGATCAAC  520
          T T                      C T

521  GGAGTAGAATGGCACGATTCATCTGAGGATCAGTGCAGGA  560
         T            T              A

561  TACTTTGGAAAGGAAGTGGAAAATCTTCAGACCCAGCAGG  600
         C        A      G       T     T

601  ATCTTTCAGAGTCACCATCAGAGTGGCTCTTCAAAACCCC  640
         T                T              A

641  AAGTAATAGACTCCGGATCAGAGCCTGGTCCAAGCCCACA  680
           A T
```

FIG. 16A

```
681  ACCAACACCCACTCCAACTCCCCAAAAGCATGAGCGATTT   720

721  ATTGCTTACGTCGGCATACCTATGCTGACCATTCAAGAAT   760

SYNTHETIC PLANT GENES FROM BT KURSTAKI AND METHOD FOR PREPARATION

This is a Continuation, of application U.S. Ser. No. 08/433,111, filed on May 3, 1995, now abandoned, which is a divisional of U.S. Ser. No. 07/959,506, filed Oct. 9, 1992, now U.S Pat. No. 5,500,365, which is a continuation of U.S. Ser. No. 07/476,661, filed Feb. 12, 1990, now abandoned, which is a continuation-in-part of U.S. Ser. No. 07/315,355, filed Feb. 24, 1989, now abandoned.

BACKGROUND OF THE INVENTION

The present invention relates to genetic engineering and more particularly to plant transformation in which a plant is transformed to express a heterologous gene.

Although great progress has been made in recent years with respect to transgenic plants which express foreign proteins such as herbicide resistant enzymes and viral coat proteins, very little is known about the major factors affecting expression of foreign genes in plants. Several potential factors could be responsible in varying degrees for the level of protein expression from a particular coding sequence. The level of a particular mRNA in the cell is certainly a critical factor.

The potential causes of low steady state levels of mRNA due to the nature of the coding sequence are many. First, full length RNA synthesis micas not occur at a high frequency. This could, for example, be caused by the premature termination of RNA during transcription or due to unexpected mRNA processing during transcription. Second, full length RNA could be produced but then processed (splicing, polyA addition) in the nucleus in a fashion that creates a nonfunctional mRNA. If the RNA is properly synthesized, terminated and polyadenylated, it then can move to the cytoplasm for translation. In the cytoplasm, mRNAs have distinct half lives that are determined by their sequences and by the cell type in which they are expressed. Some RNAs are very short-lived and some are much more long-lived. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure. It is likely that structure per se or particular structural features also have a role in determining RNA stability.

Some particular sequences and signals have been identified in RNAs that have the potential for having a specific effect on RNA stability. This section summarizes what is known about these sequences and signals. These identified sequences often are A+T rich, and thus are more likely to occur in an A+T rich coding sequence such as a *B.t.* gene. The sequence motif ATTTA (or AUUUA as it appears in RNA) has been implicated as a destabilizing sequence in mammalian cell mRNA (Shaw and Kamen, 1986). No analysis of the function of this sequence in plants has been done. Many short lived mRNAs have A+T rich 3' untranslated regions, and these regions often have the ATTTA sequence, sometimes present in mutiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurences of ATTTA are destabilizing elements or whether any of these effects are likely to be seen in plants.

Some studies on mRNA degradation in animal cells also Indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA.

Another example is the differential stability of IgG mRNA in B lymphocytes during B cell maturation (Genovese and Milcarek, 1988). A final example is the instability of a mutant beta-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability (Lim et al., 1988). These examples all orovide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eucaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Experiments in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been retlaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occuring mRNAs that are normally polyadenylated, it has been observed that disruption of this process, either by altering the polyA signal or other sequences in the mRNA, profound effects can be obtained in the level of functional mRNA. This has been observed in several naturally occuring mRNAs, with results that are gene specific so far. There are no general rules that can be derived yet from the study of mutants of these natural genes, and no rules that can be applied to heterologous genes. Below are four examples:

1. In a globin gene, absence of a proper polyA site leads to improper termination of transcription. It is likely, but not proven, that the improperly terminated RNA is nonfunctional and unstable (Proudfoot et al., 1987).

2. In a globin gene, absence of a functional polyA signal can lead to a 100-fold decrease in the level of mRNA accumulation (Proudfoot et al., 1987).

3. A globin gene polyA site was placed into the 3' ends of two different histone genes. The histone genes contain a secondary structure (stem-loop) near their 3' ends. The amount of properly polyadenylated histone mRNA produced from these chimeras decreased as the distance between the stem-loop and the polyA site increased. Also, the two histone genes produced greatly different levels of properly polyadenylated mRNA. This suggests an interaction between the polyA site and other sequences on the mRNA that can modulate mRNA accumulation (Pandy and Marzluff, 1987).

4. The soybean leghemoglobin gene has been cloned into HeLa cells, and it has been determined that this plant gene contains a "cryptic" polyadenylation signal that is active in animal cells, but is not utilized in plant cells. This leads to the production of a new polyadenylated mRNA that is nonfunctional. This again shows that analysis of a gene in one cell type cannot predict its behavior in alternative cell types (Wiebauer et al., 1988).

From these examples, it is clear that in natural mRNAs proper polyadenylation is mportant in mRNA accumulation, and that disruption of this process can effect mRNA levels significantly. However, insufficient knowledge exists to predict the effect of changes in a normal gene. In a heterologous gene, where we do not know if the putative polyA sites (consensus sequences) are functional, it is even harder to predict the consequences. However, it is possible that the putative sites identified are disfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites below called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as B.t.

| PA | AATAAA | Major consensus site |
|---|---|---|
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

Another type of RNA processing that occurs in the nucleus is intron splicing. Nearly all of the work on intron Processing has been done in animal cells, but some data is emerging from plants. Intron processing depends on proper 5' and 3' splice junction sequences. Consensus sequences for these junctions have been derived for both animal and plant mRNAs, but only a few nucleotides are known to be invariant. Therefore, it is hard to predict with any certainty whether a putative splice junction is functional or partially functional based solely on sequence analysis. In particular, the only invariant nucleotides are GT at the 5' end of the intron and AG at the 3' end of the intron. In plants, at every nearby posit on, either within the intron or in the exon flanking the intron, all four nucleotides can be found, although some positions show some nucleotide preference (Brown, 1986; Hanley and Schuler, 1988).

A plant intron has been moved from a patatin gene into a GUS gene. To do this, site directed mutagenesis was performed to introduce new restriction sites, and this mutagenesis changed several nucleotides in the intron and exon sequences flanking the GT and AG. This intron still functioned properly, indicating the importance of the GT and AG and the flexibility at other nucleotide positons. There are of course many occurences of GT and AG in all genes that do not function as intron splice junctions, so there must be some other sequence or structrual features that identify splice junctions. In plants, one such feature appears to be base composition per se. Wiebauer et al. (1988) and Goodall et al. (1988) have analyzed plant introns and exons and found that exons have ~50% A+T while introns have ~70% A+T. Goodall et al. (1988) also created an artificial plant intron that has consensus 5' and 3' splice junctions and a random A+T rich internal sequence. This intron was spliced correctly in plants. When the internal segment was replaced by a G+C rich sequence, splicing efficiency was drastically reduced. These two examples demonsatrate that intron recognition in plants may depend on very general features—splice junctions that have a great deal of sequence diversity and A+T richness of the intron itself. This, of course, makes it difficult to predict from sequence alone whether any particular sequence is likely to function as an active or partially active intron for RNA processing.

B.t. genes being A+T rich contain numerous stretches of various lengths that have 70% or greater A+T. The number of such stretches identified by sequence analysis depends on the length of sequence scanned.

As for polyadenylation described above, there are complications in predicting what sequences might be utilized as splice sites in any given gene. First, many naturally occuring genes have alternative splicing pathways that create alternative combinations of exons in the final mRNA (Gallega and Nadal-Ginard, 1988; Helfman and Ricci, 1988; Tsurushita and Korn, 1989). That is, some splice junctions are apparently recognized under some circumstances or in certain cell types, but not in others. The rules governing this are not understood. In addition, there can be an interaction between processing paths such that utilization of a particular polyadenylation site can interfere with splicing at a nearby splice site and vice versa (Adami and Nevins, 1988; Brady and Wold, 1988; Marzluff and Pandey, 1988). Again no predictive rules are available. Also, sequence changes in a gene can drastically alter the utilization of particular splice junctions. For example, in a bovine growth hormone gene, small deletions in an exon a few hundred bases downstream of an intron cause the splicing efficiency of the intron to drop from greater than 95% to less than 2% (essentially nonfunctional). Other deletions however have essentially no effect (Hampson and Rottman, 1988). Finally, a variety of in vitro and in vivo experiments indicate that mutations that disrupt normal splicing lead to rapid degradation of the RNA in the nucleus. Splicing is a multistep process in the nucleus and mutations in normal splicing can lead to blockades in the process at a variety of steps. Any of these blockades can then lead to an abnormal and unstable RNA. Studies of mutants of normally processed (polyadenylation and splicing) genes are relevant to the study of heterologous genes such as B.t. B.t. genes might contain functional signals that lead to the production of aberrant nonfunctional mRNAs, and these mRNAs are likely to be unstable. But the B.t. genes are perhaps even more likely to contain signals that are analogous to mutant signals in a natural gene. As shown above these mutant signals are very likely to cause defects in the processing pathways whose consequence is to produce unstable mRNAs.

It is not known with any certainty what signals RNA transcription termination in plant or animal cells. Some studies on animal genes that indicate that stretches of sequence rich in T cause termination by calf thymus RNA polymerase II in vitro. These studies have shown that the 3' ends of in vitro terminated transcripts often lie within runs of T such as T5, T6 or T7. Other identified sites have not been composed solely of T, but have had one or more other nucleotides as well. Termination has been found to occur within the sequences TATTTTTT, ATTCTC, TTCTT (Dedrick et al., 1987; Reines et al., 1987). In the case of these latter two, the context in which the sequence is found has been C+T rich as well. It is not known if this is essential. Other studies have implicated stretches of A as potential transcriptional terminators. An interesting example from SV40 illustrates the uncertainty in defining terminators based on sequence alone. One potential terminator in SV40 was identified as being A rich and having a region of dyad symmetry (potential stem-bcoo) 5' to the A rich stretch. However, a second terminator identified experimentally downstream in the same gene was not A rich and included no potential secondary structure (Kessler et al., 1988) Of course, due to the A+T content of B.t. genes, they are rich in runs of A or T that could act as terminators. The importance of termination to stability of the mRNA is shown by the globin gene example described above. Absence of a normal polyA site leads to a failure in proper termination with a consequent decrease in mRNA.

There is also an effect on mRNA stability due to the translation of the mRNA. Premature translational termination in human triose phosphate isomerase leads to instability of the mRNA (Daar et al., 1988). Another example is the beta-thallesemic globin mRNA described above that is specifically unstable in bone marrow cells (Lim et al., 1988). The defect in this mutant gene is a single base pair deletion at codon 44 that leads to translational termination (a nonsense codon) at codon 60. Compared to properly translated normal globin mRNA, this mutant RNA is very unstable. These results indicate that an improperly translated mRNA is unstable. Other work in veast indicates that proper but poor translation can have an effect on mRNA levels. A heterologous gene was modified to convert certain codons to more yeast preferred codons. An overall 10-fold increase in protein production was achieved, but there was also about a 3-fold increase in mRNA Hoekema et al., 1987). This indicates that more efficient translation can lead to greater mRNA stability, and that the effect of codon usage can be at the RNA level as well as the translational level. It is not clear from codon usage studies which codons lead to poor translation, or how this is coupled to mRNA stability.

SUMMARY OF THE INVENTION

It is an object of the present invention to provide a method for preparing synthetic plant genes which express their respective proteins at relatively high levels when compared to wild-type genes. It is yet another object of the present invention to provide synthetic plant genes which express the crystal protein toxin of *Bacillus thuringiensis* at relatively high levels.

BRIEF DESCRIPTION OF THE DRAWINGS

FIGS. 2A–2C illustrate a comparison of the changes in the modified B.t.k. HD-1 sequence of Example 1 (lower line) (SEQ ID NO:20) versus the wild-type sequence of B.t.k. HD-1 which encodes the crystal protein toxin (upper line).

FIGS. 3A–3C illustrate a comparison of the changes in the synthetic B.t.k. HD-1 sequence of Example 2 (lower line) (SEQ ID NO:22) versus the wild-type sequence of B.t.k. HD-1 which encodes the crystal protein toxin (upper line).

FIGS. 4A–4C illustrate a comparison of the changes in the synthetic B.t.k. HD-73 sequence of Example 3 (lower line) (SEQ ID NO:23) versus the wild-type sequence of B.t.k. HD-73 (upper line).

FIGS. 8A–8C illustrate a comparison of the changes in the synthetic truncated *B.t.k.* HD-73 gene (Amino acids 29–615 with an N-terminal Met-Ala) of Example 3 (lower line) (SEQ ID NO:21) versus the wild-type sequence of *B.t.k.* HD-73 (upper line).

FIGS. 9A–9E illustrate a comparison of the changes in the synthetic/wild-type full length B.t.k. HD-73 sequence of Example 3 (lower line) (SEQ ID NO:24) versus the wild-type full-length sequence of *B.t.k.* HD-73 (upper line).

FIGS. 10A–10E illustrate a comparison of the changes in the synthetic/modified full length *B.t.k.* HD-73 sequence of Example 3 (lower line) (SEQ ID NO:25) versus the wild-type full-length sequence of *B.t.k.* HD-73 (upper line).

FIGS. 11A–11E illustrate a comparison of the changes in the fully synthetic full-length *B.t.k.* HD-73 sequence of Example 3 (lower line) (SEQ ID NO:26) versus the wild-type full-length sequence of *B.t.k.* HD-73 (upper line).

FIGS. 12A–12C illustrate a comparison of the changes in the synthetic *B.t.t.* sequence of Example 5 (lower line) versus the wild-type sequence of *B.t.t.* which encodes the crystal protein toxin (upper line).

FIG. 13A–13C illustrates a comparison of the changes in the synthetic *B.t.* P2 sequence of Example 6 (lower line) versus the wild-type sequence of *B.t.k.* HD-1 which encodes the P2 protein toxin (upper line).

FIGS. 14A–14E illustrate a comparison of the changes in the synthetic *B.t. entomocidus* sequence of Example 7 (lower line) versus the wild-type sequence of *B.t. entomocidus* which encodes the Btent protein toxin (upper line).

FIG. 16A–16B illustrate a comparison of the changes in the synthetic potato leaf roll virus (PLRV) coat protein sequence of Example 9 (lower line) versus the wild-type coat protein sequence of PLRV (upper line).

DETAILED DESCRIPTION OF THE INVENTION

Figure 1A:
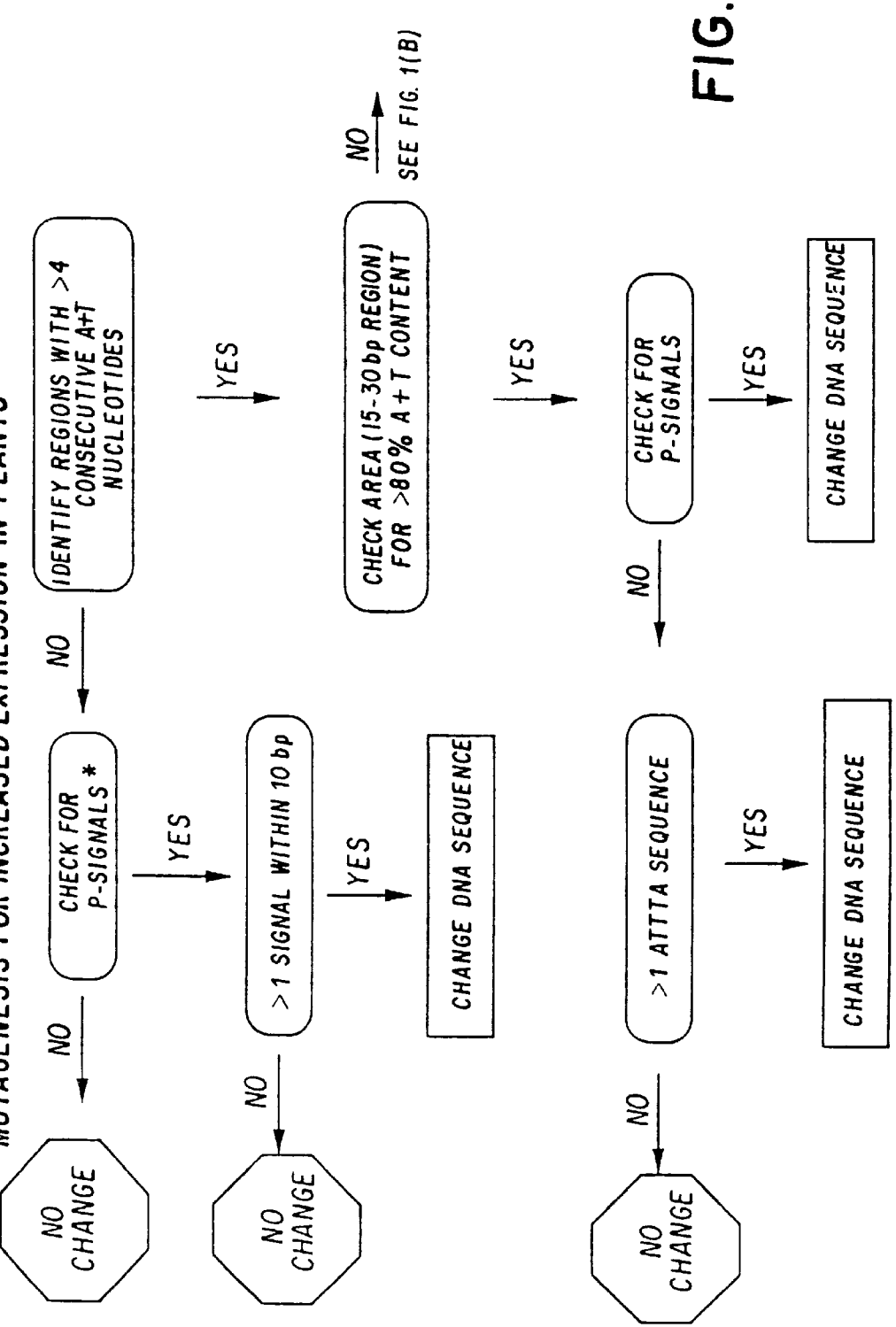
FIGS. 1A–1B illustrate the steps employed in modifying a wild-type gene to increase expression efficiency in plants.

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

For brevity and clarity of description, the present invention will be primarily described with respect to the preparation of synthetic plant genes which encode the crystal protein toxin of *Bacillus thuringiensis* (*B.t.*). Suitable *B.t.* subspecies include, but are not limited to, *B.t. kurstaki* HD-1, *B.t. kurstaki* HD-73, *B.t. sotto*, *B.t. berliner*, *B.t. thuringiensis*, *B.t. tolworthi*, *B.t. dendrolimus*, *B.t. alesti*, *B.t. galleriae*, *B.t. aizawai*, *B.t. subtoxicus*, *B.t. entomocidus*, *B.t. tenebrionis* and *B.t. san diego*. However, those skilled in the art will recognize and it should be understood that the present method may be used to prepare synthetic plant genes which encode non-plant proteins other than the crystal protein toxin of *B.t.* as well as plant proteins (see for instance, Example 9).

The expression of *B.t.* genes in plants is problematic. Although the expression of *B.t.* genes in plants at insecticidal levels has been reported, this accomplishment has not been straightforward. In particular, the expression of a full-length lepidopteran specific *B.t.* gene (comprising DNA from a *B.t.k.* isolate) has been reported to be unsuccessful in yielding insecticidal levels of expression in some plant species (Vaeck et al., 1987 and Barton et al., 1987).

It has been reported that expression of the full-length gene from *B.t.k.* HD-1 was detectable in tomato plants but that truncated genes led to a higher frequency of insecticidal plants with an overall higher level of expression. Truncated genes of *B.t. berliner* also led to a higher frequency of insecticidal plants in tobacco (Vaeck et al., 1987). On the other hand, insecticidal plants were provided from lettuce transformants using a full-length gene.

It has also been reported that the full length gene from *B.t.k.* HD-73 gave some nsecticidal effect in tobacco (Adang et al., 1987). However, the *B.t.* mRNA detected in these plants was only 1.7 kb compared to the expected 3.7 kb indicating improper expression of the gene. It was suggested that this truncated mRNA was too short to encode a functional truncated toxin, but there must have been a low level of longer mRNA in some plants or no insecticidal activity would have been observed. Others have reported in a publication that they observed a large amount of shorter than expected mRNA from a truncated *B.t.k.* gene, but some mRNA of the expected size was also observed. In fact, it was suggested that expression of the full length gene is toxic to tobacco callus (Barton et al., 1987).

The above illustrates that lepidopteran type *B.t.* genes are poorly expressed in plants compared to other chimeric genes previously expressed from the same promoter cassettes.

The expression of *B.t.t.* in tomato and potato is at levels similar to that of *B.t.k.* (i.e., poor). *B.t.t.* and *B.t.k.* genes share only limited sequence homology, but they share many common features in terms of base composition and the presence of particular A+T rich elements.

All reports in the field have noted the lower than expected expression of *B.t.* genes in plants. In general, insecticidal efficacy has been measured using insects very sensitive to *B.t.* toxin such as tobacco hornworm. Although it has been possible to obtain plants totally protected against tobacco hornworm, it is important to note that hornworm is up to 500 fold more sensitive to *B.t.* toxin than some agronomically important insect pests such as beet armyworm. It is therefore of interest to obtain transgenic plants that are protected against all important lepidopteran pests (or against Colorado potato beetle in the case of *B.t. tenebrionis*), and in addition to have a level of *B.t.* expression that provides an additional safety margin over and above the efficacious protection level. It is also important to devise plant genes which function reproducibly from species to species, so that insect resistant plants can be obtained in a predictable fashion.

In order to achieve these goals, it is important to understand the nature of the poorer than expected expression of *B.t.* genes in plants. The level of stable *B.t.* mRNA in plants is much lower than expected. That is, compared to other coding sequences driven by the same promoter, the level of *B.t.* mRNA measured by Northern analysis or nuclease protection experiments is much lower. For example, tomato plant 337 (Fischhoff et al., 1987) was selected as the best expressing plant with pMON9711 which contains the *B.t.k.* HD-1 KpnI fragment driven by the CaMV 35S promoter and contains the NOS-NPTII-NOS selectable marker gene. In this plant the level of *B.t.* mRNA is between 100 to 1000 fold lower than the level of NPTII mRNA, even though the 35S promoter is approximately 50-fold stronger than the NOS promoter (Sanders et al., 1987).

The level of *B.t.* toxin protein detected in plants is consistent with the low level of *B.t.* mRNA. Moreover, the insecticidal efficacy of the transgenic plants correlates with the B.t. protein level indicating that the toxin protein produced in plants is biologically active. Therefore, the low level of B.t. toxin expression may be the result of the low levels of B.t. mRNA.

Messenger RNA levels are determined by the rate of synthesis and rate of degradation. It is the balance between these two that determines the steady state level of mRNA. The rate of synthesis has been maximized by the use of the CaMV 35S promoter, a strong constitutive plant expressible promoter. The use of other plant promoters such as nopaline synthase (NOS), mannopine synthase (MAS) and ribulose bisphosphatecarboxylase small subunit (RUBISCO) have not led to dramatic changes in the levels of B.t. toxin protein expression indicating that the effects determining B.t. toxin protein levels are promoter independent. These data imply that the coding sequences of DNA genes encoding B.t. toxin proteins are somehow responsible for the poor expression level, and that this effect is manifested by a low level of accumulated stable mRNA.

Lower than expected levels of mRNA have been observed with four different lepidopteran specific genes (two from B.t.k. HD-1; B.t. berliner and B.t.k. HD-73) as well as the gene from the coleopteran specific B.t. tenebrionis. It appears that for lepidopteran type B.t. genes these effects are manifest more strongly in the full length coding sequences than in the truncated coding sequences. These effects are seen across plant species although their magnitude seems greater in some plant species such as tobacco.

The nature of the coding sequences of B.t. genes distinguishes them from plant genes as well as many other heterologous genes expressed in plants. In particular, B.t. genes are very rich (~62%) in adenine (A) and thymine (T) while plant genes and most bacterial genes which have been expressed in plants are on the order of 45–55% A+T. The A+T content of the genomes (and thus the genes) of any organism are features of that organism and reflect its evolutionary history. While within any one organism genes have similar A+T content, the A+T content can vary tremendously from organism to organism. For example, some Bacillus species have among the most A+T rich genomes while some Steptomyces species are among the least A+T rich genomes (~30 to 35% A+T).

Due to the degeneracy of the genetic code and the limited number of codon choices for any amino acid, most of the "excess" A+T of the structural coding sequences o some Bacillus species are found in the third position of the codons. That is, genes of some Bacillus species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another oraanism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likliehood of occurence of any particular oligonucleotide sequence. Thus, a gene from E. coli with a 50% A+T content is much less likely to contain any particular A+T rich segment than a gene from B. thuringiensis.

As described above, the expression of B.t. toxin protein in plants has been problematic. Although the observations made in other systems described above offer the hope of a means to elevate the expression level of B.t. toxin proteins in plants, the success obtained by the present method is quite unexpected. Indeed, inasmuch as it has been recently reported that expression of the full-length B.t.k. toxin protein in tobacco makes callus tissue necrotic (Barton et al., 1987); one would reasonably expect that high level expression of B.t. toxin protein to be unattainable due to the reported toxicity effects.

In its most rigorous application, the method of the present invention involves the modification of an existing structural coding sequence ("structural gene") which codes for a particular protein by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

Figure 1B:
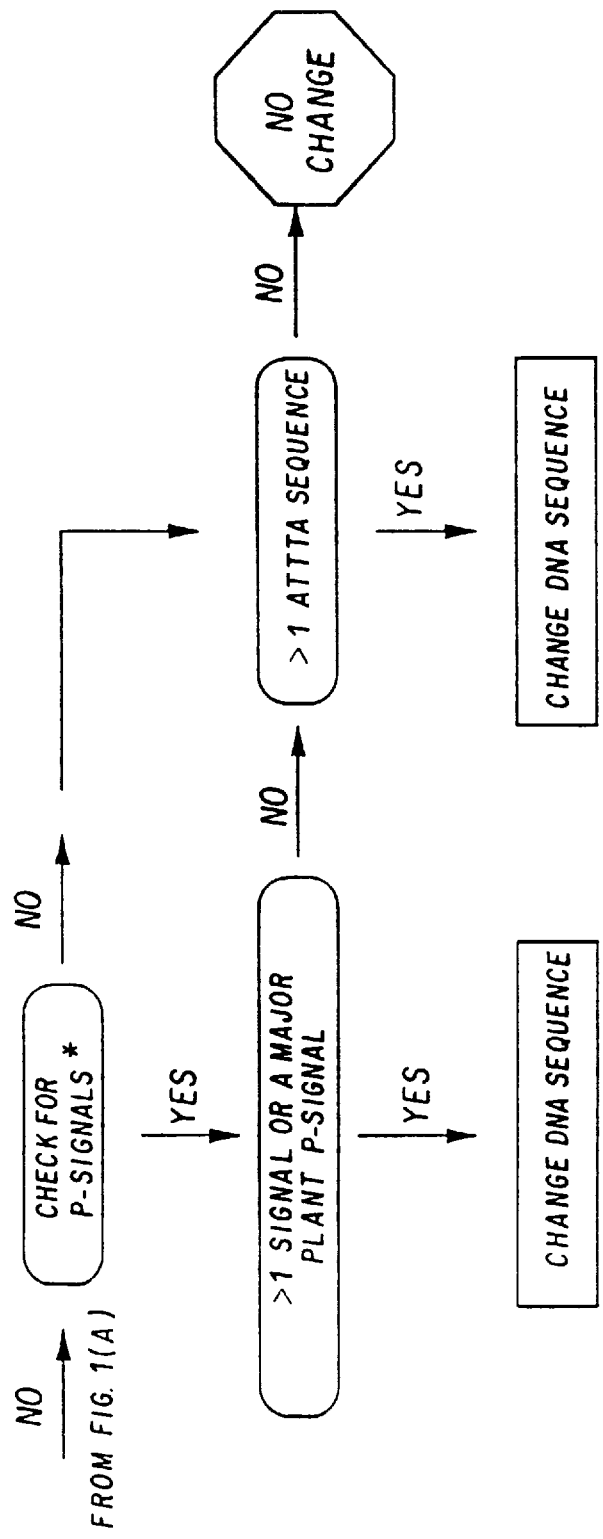

Another embodiment of the present invention, represented in the flow diagram of FIG. 1, employs a method for the modification of an existing structural gene or alternately the de novo synthesis of a structural gene which method is somewhat less rigorous than the method first described above. Referring to FIG. 1, the selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the 15 to 30 nucleotide regions surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

SYNTHETIC OLIGONUCLEOTIDES FOR MUTAGENESIS

The oligonucleotides used in the mutagenesis are designed to maintain the proper amino acid sequence and reading frame and preferably to not introduce common restriction sites such as BglII, HindIII, SacI, KpnI, EcoRI, NcoI, PstI and SalI into the modified gene. These restriction sites are found in multi-Linker insertion sites of cloning vectors such as plasmids pUC118 and pMON7258. Of course, the introduction of new polyadenylation signals, ATTTA sequences or consecutive stretches of more than five A+T or G+C, should also be avoided. The preferred size for the oligonucleotides is around 40–50 bases, but fragments ranging from 18 to 100 bases have been utilized. In most cases, a minimum of 5 to 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table I below) so as to avoid codons which are rarely found in plant genomes, and efforts should be made to select codons to preferably adjust the G+C content to about 50%.

TABLE I

Preferred Codon Usaoe in Plants

| Amino Acid | Codon | Percent Usage in Plants |
|---|---|---|
| ARG | CGA | 7 |
| | CGC | 11 |
| | CGG | 5 |
| | CGU | 25 |
| | AGA | 29 |
| | AGG | 23 |
| LEU | CUA | 8 |
| | CUC | 20 |
| | CUG | 10 |
| | CUU | 28 |
| | UUA | 5 |
| | UUG | 30 |
| SER | UCA | 14 |
| | UCC | 26 |
| | UCG | 3 |
| | UCU | 21 |
| | AGC | 21 |
| | AGU | 15 |
| THR | ACA | 21 |
| | ACC | 41 |
| | ACG | 7 |
| | ACU | 31 |
| PRO | CCA | 45 |
| | CCC | 19 |
| | CCG | 9 |
| | CCU | 26 |
| ALA | GCA | 23 |
| | GCC | 32 |
| | GCG | 3 |
| | GCU | 41 |
| GLY | GGA | 32 |
| | GGC | 20 |
| | GGG | 11 |

TABLE I-continued

Preferred Codon Usaoe in Plants

| Amino Acid | Codon | Percent Usage in Plants |
|---|---|---|
| | GGU | 37 |
| ILE | AUA | 12 |
| | AUC | 45 |
| | AUU | 43 |
| VAL | GUA | 9 |
| | GUC | 20 |
| | GUG | 28 |
| | GUU | 43 |
| LYS | AAA | 36 |
| | AAG | 64 |
| ASN | AAC | 72 |
| | AAU | 28 |
| GLN | CAA | 64 |
| | CAG | 36 |
| | CAC | 65 |
| | CAU | 35 |
| GLU | GAA | 48 |
| | GAG | 52 |
| ASP | GAC | 48 |
| | GAU | 52 |
| TYR | UAC | 68 |
| | UAU | 32 |
| CYS | UGC | 78 |
| | UGU | 22 |
| PHE | UUC | 56 |
| | UUU | 44 |
| MET | AUG | 100 |
| TRP | UGG | 100 |

Regions with many consecutive A+T bases or G+C bases are predicted to have a higher likelihood to rorm hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators). However, it is difficult to credit the biological effect of a potential hairpin forming region.

It is evident to those skilled in the art that while the above description is directed toward the modification of the DNA sequences of wild-type genes, the present method can be used to construct a completely synthetic gene for a given amino acid sequence. Regions with five or more consecutive A+T or G+C nucleotides should be avoided. Codons should be selected avoiding the TA and CG doublets in codons whenever possible. Codon usage can be normalized against a plant preferred codon usage table (such as Table I) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the Literature. These include the nopaline synthase (NOS) and octopine synthase (OCS) promoters (which are carried on tumor-inducing plasmids of *Agrobacterium tumefaciens*), the Cauliflower Mosaic Virus (CaMV) 19S and 35S promoters, the light-inducible promoter from the small subunit of ribulose bis-phosphate carboxylase (ssRUBISCO, a very abundant plant polypeptide) and the mannopine synthase (MAS) promoter (Velten et al. 1984 and Velten & Schell, 1985). All of these promoters have been used to create various types of DNA constructs which have been expressed in plants (see e.g., PCT publication WO84/02913 (Rogers et al., Monsanto).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of protein.

The promoters used in the DNA constructs (i.e. chimerc plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak (1984).

The DNA construct of the present invention also contains a modified or fully-synthetic structural coding sequence which has been changed to enhance the performance of the gene in plants. In a particular embodiment of the present invention the enhancement method has been applied to design modified and fully synthetic genes encoding the crystal toxin protein of *Bacillus thuringiensis*. The structural genes of the present invention may optionally encode a fusion protein comprising an amino-terminal chloroplast transit peptide or secretory signal sequence (see for instance, Examples 10 and 11).

The DNA construct also contains a 3' non-translated region. The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes like the soybean storage protein (7S) genes and the small subunit of the RuBP carboxylase (E9) gene. An example of a preferred 3' region is that from the 7S gene, described in greater detail in the examples below.

Plant Transformation

A chimeric plant gene containing a structural coding sequence of the present invention can be inserted into the genome of a plant by any suitable method. Suitable plants for use in the practice of the present invention include, but are not limited to, soybean, cotton, alfalfa, oilseed rape, flax, tomato, sugarbeet, sunflower, potato, tobacco, maize, rice and wheat. Suitable plant transformation vectors include those derived from a Ti olasmid of *Agrobacterium tumefaciens*, as well as those disclosed, e.g., by Herrera-Estrella (1983), Bevan (1983), Klee (1985) and EPO publication 120,516 (Schilperoort et al.). In addition to plant transformation vectors derived from the Ti or root-inducing (Ri) plasmids of Agrobacterzium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

Figure 5:
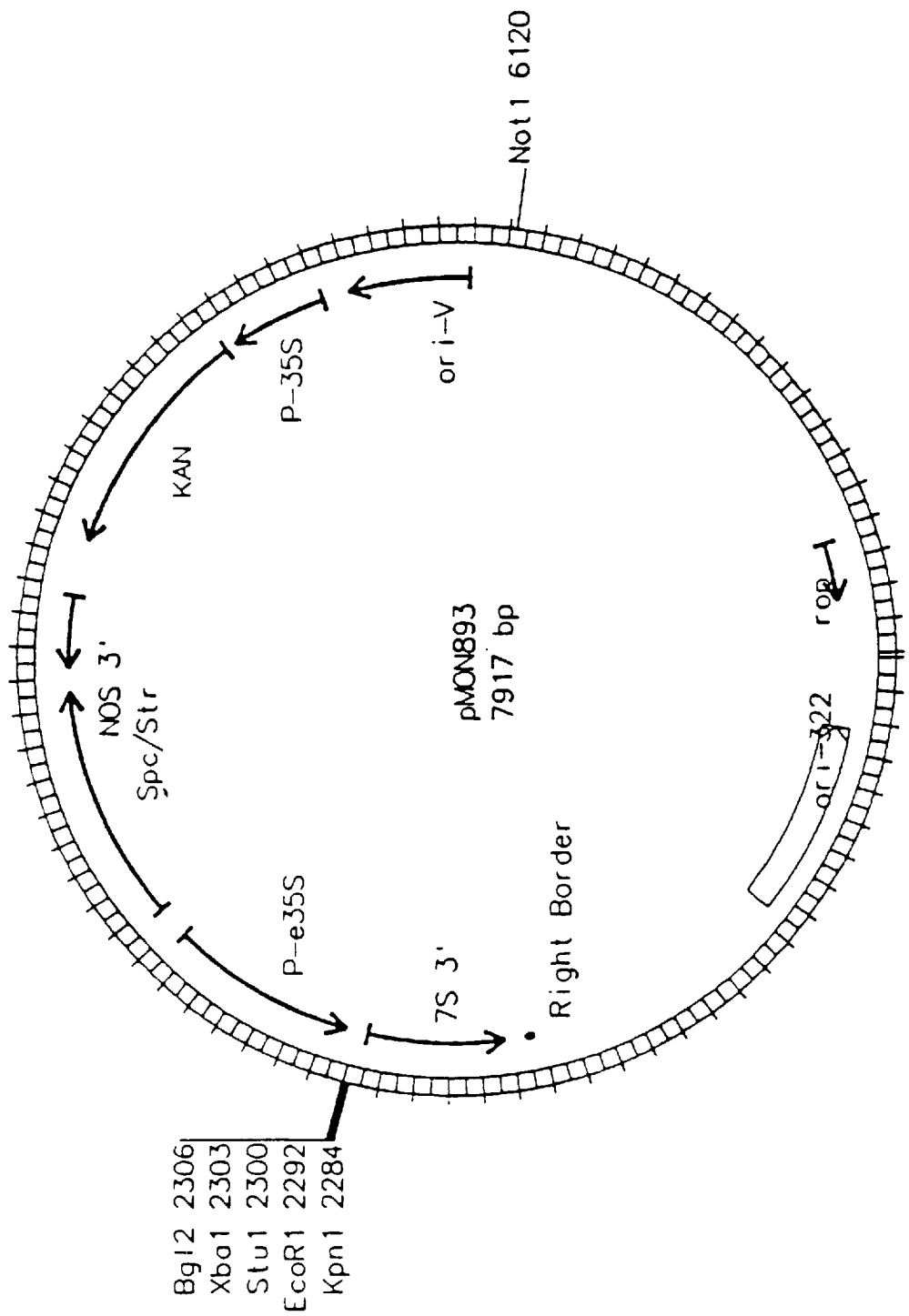
FIG. 5 represents a plasmid map of intermediate plant transformation vector cassette pMON893.

A particularly useful Ti plasmid cassette vector for transformation of dicotyledonous plants is shown in FIG. 5. Referring to FIG. 5, the expression cassette pMON893 consists of the enhanced CaMV35S promoter (EN 35S) and the 3' end including polyadenylation signals from a soybean gene encoding the alpha-prime subunit of beta-conglycinin. Between these two elements is a multilinker containing multicle restriction sites or the insertion of genes.

The enhanced CaMV35S promoter was constructed as follows. A fragment of the CaMV35S promoter extending between position −343 and +9 was previously constructed in pUC13 by Odell et al. (1985). This segment contains a region identified by Odell et al. (1985) as being necessary for maximal expression of the CaMV35S promoter. It was excised as a ClaI-HindIII fragment, made blunt ended with DNA polymerase I (Klenow fragment) and inserted into the HincII site or pUC18. This ucstream region of the 35S promoter was excised from this plasmid as a HindIII-EcoRV fragment (extending from −343 to −90) and inserted into the same plasmid between the HindIII and PstI sites. The enhanced CaMV35S promoter thus contains a duplication of sequences between −343 and −90 (Kay et al., 1987).

The 3' end of the 7S gene is derived from the 7S gene contained on the clone designated 17.1 (Schuler et al., 1982). This 3' end fragment, which includes the polyadenylation signals, extends from an AvaII site located about 30 bp upstream of the termination codon for the beta-conglycinin aene in clone 17.1 to an EcoRI site located about 450 Up downstream of this termination codon.

The remainder of pMON893 contains a segment of pBR322 which provides an origin of replication in *E. coli* and a region for homologous recombination with the disarmed T-DNA in Agrobacterium strain ACO (described below); the oriV region from the broad host range plasmid RK1; the streptonycin/spectinomycin resistance gene from Tn7; and a chimeric NPTII gene, containing the CaMV35S promoter and the nopaline synthase (NOS) 3' end, which provides kanamycin resistance in transformed plant cells.

Figure 6:
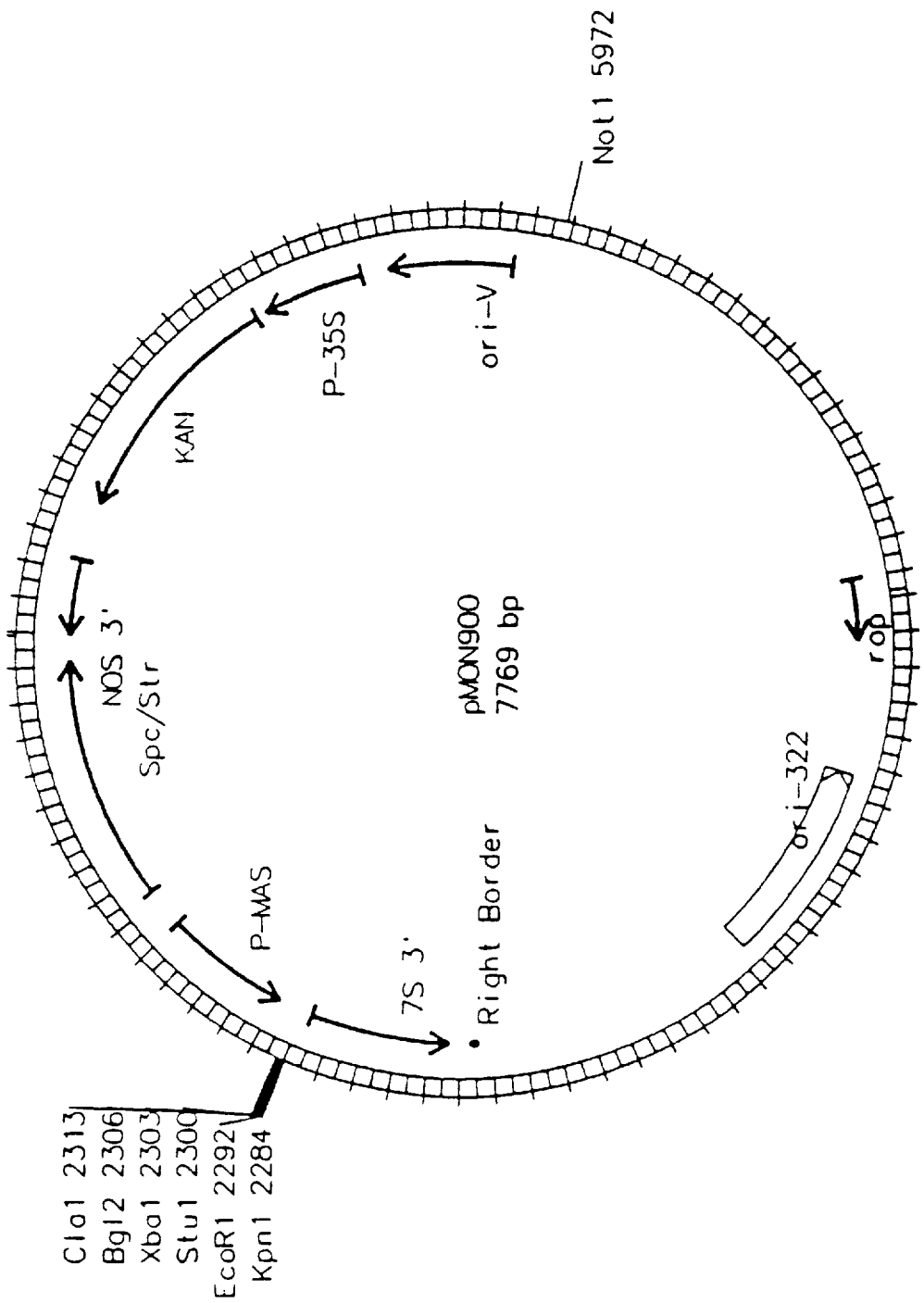
FIG. 6 represents a plasmid map of intermediate plant transformation vector cassette pMON900.

Referring to FIG. 6, transformation vector plasmid pMON900 is a derivative of pMON893. The enhanced CaMV35S promoter of pMON893 has been replaced with the 1.5 kb mannopine synthase (MAS) promoter (Velten et al. 1984). The other segments are the same as plasmid pMON893. After incorporation of a DNA construct into clasmid vector pMCN893 or pMON900, the intermediate vector is introducer into A. tumefaciens strain ACO which contains a disarmed Ti plasmid. Cointegrate Ti plasmid vectors are selected and used to transform dicotyledonous plants.

Figure 7:
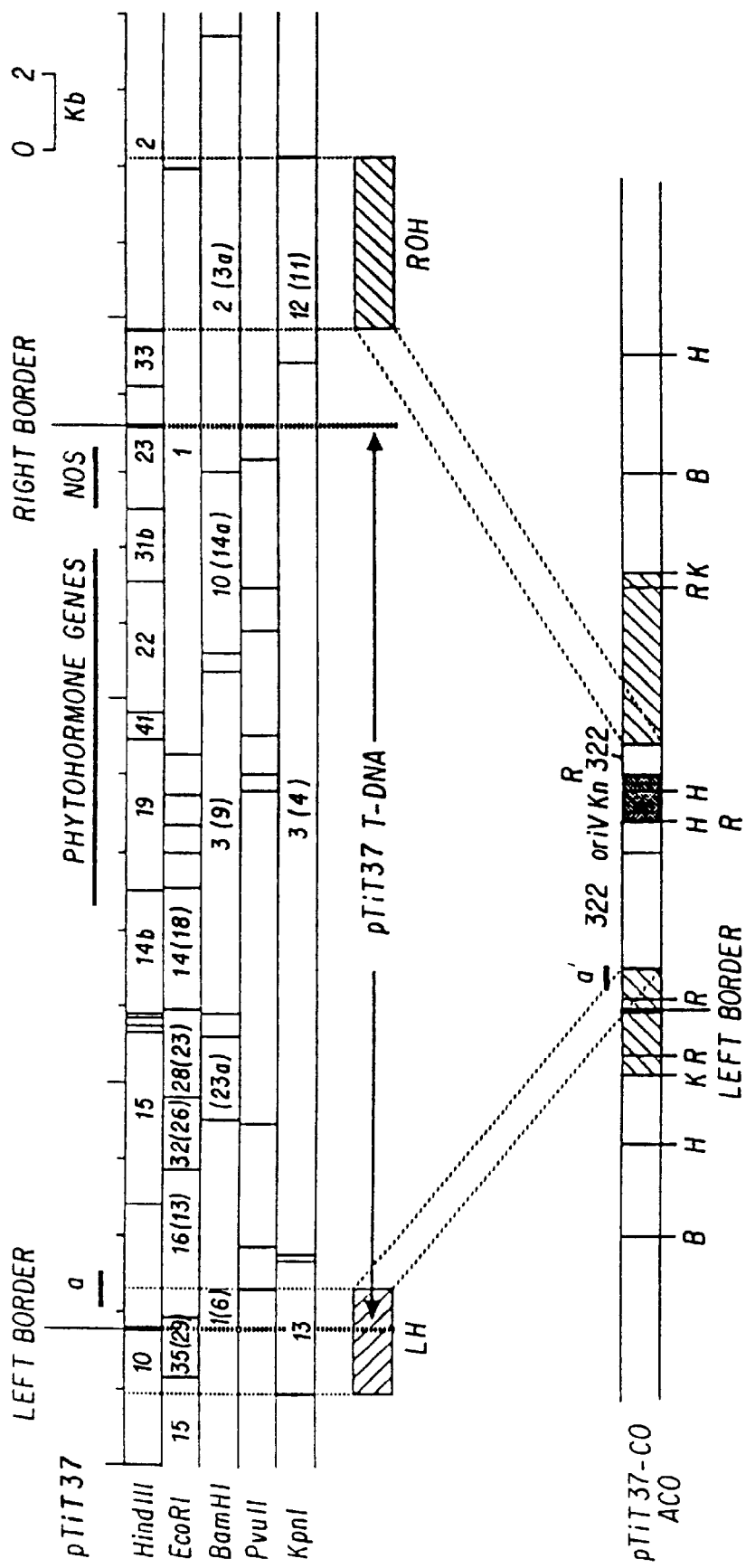
FIG. 7 represents a map for the disarmed T-DNA of *A. tumefaciens* ACO.

Referring to FIG. 7, A. tumefaciens ACO is a disarmed strain similar to pTiB6SE described by Fraley et al. (1985). For construction of ACO the starting Agrobacterium strain was the strain A208 which contains a nopaline-type Ti plasmid. The Ti plasmid was disarmed in a manner similar to that described by Fraley et al. (1985) so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to the segments in pMON893 and provide a region of homology for cointegrate formation.

The following examples are provided to better elucidate the practice of the present invention and should not be interpreted in any way to limit the scope of the present invention. Those skilled in the art will recognize that various modifications, truncations etc. can be made to the methods and genes described herein while not departing from the spirit and scope of the present invention.

EXAMPLE 1

Modified B.t.k. HD-1 Gene

Referring to FIG. 2, the wild-type B.t.k. HD-1 gene is known to be expressed poorly in plants as a full length gene or as a truncated gene. The G+C content of the B.t.k. gene is low (37%) containing many A+T rich regions, potential polyadenylation sites (18 sites; see Table II for the list of sequences) and numerous ATTTA sequences.

TABLE II

List of Sequences of the Potential Polyadenylation Signals

| | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.

All others are potential minor plant polyadenylation sites.

Table III lists the synthetic oligonucleotides designed and synthesized for the site-directed mutagenesis of the B.t.k. HD-1 gene.

TABLE III

Mutagenesis Primers for B.t.k. HD-1 Gene

| Primer | Length (bp) | Sequence |
|---|---|---|
| BTK185 | 18 | TCCCCAGATA ATATCAAC Sequence ID No. 1 |
| BTK240 | 48 | GGCTTGATTC CTAGCGAACT CTTCGATTCT CTGGTTGATG AGCTGTTC Sequence ID No. 2 |
| BTK462 | 54 | CAAAACTGAG AGGTGGAGGT TGGCAGCTTG AACGTACACG GAGAGGAGAGGAAC Sequence ID No. 3 |
| BTK669 | 48 | AGTTAGTGTA AGCTCTCTTC TGAACTGGTT GTACCTGATC CAATCTCT Sequence ID No. 4 |
| BTK930 | 39 | AGCCATGATC TGGTGACCGG ACCAGTAGTA TTCTCCTCT Sequence ID No. 5 |
| BTK1110 | 32 | AGTTGTTGGT TGTTGATCCC GATGTTAAAA GG Sequence ID No. 6 |
| BTK1380A | 37 | GTGATGAAGG GATGATGTTG TTGAACTCAG CACTACG Sequence ID No. 7 |
| BTK1380T | 100 | CAGAAGTTCC AGAGCCAAGA TTAGTAGACT TGGTGAGTGG GATTTGGGTG ATTTGTGATG AAGGGATGAT GTTGTTGAAC TCAGCACTAC GATGTATCCA Sequence ID No. 8 |
| BTK1600 | 27 | TGATGTGTGG AACTGAAGGT TTGTGGT Sequence ID No. 9 |

The B.t.k. HD-1 gene (BglII fragment from pMON9921 encoding amino acids 29–607 with a Met-Ala at the N-terminus) was cloned into pMON7258 (pUC118 derivative which contains a BglII site in the multilinker cloning region) at the BglII site resulting in pMON5342. The orientation of the B.t.k. gene was chosen so that the opposite strand (negative strand) was synthesized in filamentous phage particles for the mutagenesis. The procedure of Kunkle (1985) was used for the mutaaenesis using plasmid pMON5342 as starting material.

The regions for mutagenesis were selected in the following manner. All regions of the DNA sequence of the B.t.k. gene were identified which contained five or more consecutive base pairs which were A or T. These were ranked in terms of length and highest percentage of A+T in the surrounding sequence over a 20–30 base pair region. The DNA was then analysed for regions which might contain polyadenylation sites (see Table II above) or ATTTA sequences. Oligonucleotides were designed which maximized the elimination of A+T consecutive regions which contained one or more polyadenylation sites or ATTTA sequences. Two potential plant polyadenylation sites were rated more critical (see Table II) based on published reports. Codons were selected which increased G+C content, did not generate restriction sites for enzymes useful for cloning and assembly of the modified gene (BamHI, BglII, Sacd, NcoI, EcoRV) and did not contain the doublets TA or GC which have been reported to be infrequently found in codons in plants. The oligonucleotides were at least 18 bp long ranging up to 100 base pairs and contained at least 5–8 base pairs of direct homology to native sequences at the ends of the fragments for efficient hybridization and priming in site-directed mutagenesis reactions. FIG. 2 compares the wild-type *B.t.k.* HD-1 gene sequence with the sequence which resulted from the modifications by site-directed mutagenesis.

The end result of these changes was to increase the G+C content of *B.t.k.* gene from 37% to 41% while also decreasing the potential plant polyadenyiation sites from 18 to 7 and decreasing the ATTTA regions from 13 to 7. Specifically, the mutagenesis changes from amino (5') terminus to the carboxy (3') terminus are as follows:

BTK185 is an 18-mer used to eliminate a plant polyadenylation site in the midst of a nine base pair region of A+T.

BTK240 is a 48-mer. Seven base pairs were changed by this oligonucleotide to eliminate three potential polyadenylation sites (2 AACCAA, 1 AATTAA). Another region close to the region altered by BTK240, starting at bp 312, had a high A+T content (13 of 15 base pairs) and an ATTTA region. However, it did not contain a potential polyadenylation site and its longest string of uninterrupted A+T was seven base pairs.

BTK462 is a 54-mer introducing 13 base pair changes. The first six changes were to reduce the A+T richness of the gene by replacing wild-type codons with codons containing G and C while avoiding the CG doublet. The next seven changes made by BTK462 were used to eliminate an A+T rich region (13 of 14 base pairs were A or T) containing two ATTTA regions.

BTK669 is a 48-mer making nine individual base pair changes eliminating three possible polyadenylation sites (ATATAA, AATCAA, and AATTAA) and a single ATTTA site.

BTK930 is a 39-mer designed to increase the G+C content and to eliminate a potential polyadenylation site (AATAAT—a major site). This region did contain a nine base pair region of consecutive A+T sequence. One of the base pair changes was a G to A because a G at this position would have created a G+C rich region (CCGG(G)C). Since sequencing reactions indicate that there can be difficulties generating sequence through G+C consecutive bases, it was thought to be prudent to avoid generating potentially problematic regions even if they were problematic only in vitro.

BTK1110 is a 32-mer designed to introduce five changes in the wild-type gene. One potential site (AATAAT—a major site) was eliminated in the midst of an A+T rich region (19 of 22 base pairs).

BTK1380A and BTK1380T are responsible for 14 individual base pair changes. The first region (1380A) has 17 consecutive A+T base pairs. In this region 43 an ATTTA and a potential polyadenylation site (AATAAT). The 100-mer (1380T) contains all the changes dictated by 1380A. The large size of this primer was in part an experiment to determine if it was feasible to utilize large oligonucleotides for mutagenesis (over 60 bases in length). A second consideration was that the 100-mer was used to mutagenize a template which had previously been mutagenized by 1380A. The original primer ordered to mutagenize the region downstream and adjacent to 1380A did not anneal efficiently to the desired site as indicated by an inability to obtain clean sequence utilizing the primer. The large region of homology of 1380T did assure proper annealing. The extended size of 1380T was more of a convenience rather than a necessity. The second region adjacent to 1380A covered by 1380T has a high A+T content (22 of 29 bases are A or T).

BTK1600 is a 27-mer responsible for five individual base pair changes. An ATTTA region and a plant polyadenylation site were identified and the appropriate changes engineered.

A total of 62 bases were changed by site-directed mutagenesis. The G+C content increased by 55 base pairs, the potential polyadenylation sites were reduced from 18 to seven and the ATTTA sequences decreased from 13 to seven. The changes in the DNA sequence resulted in changes in 55 of the 579 codons in the truncated *B.t.k.* gene in pMON5342 (approximately 9.5%).

Referring to Table IV modified *B.t.k.* HD-1 genes were constructed that contained all of the above modifications (pMON5370) or various subsets of individual modifications. These genes were inserted into pMON893 for plant transformation and tobacco plants containing these genes were analyzed. The analysis of tobacco plants with the individual modifications was undertaken for several reasons. Expression of the wild type truncated gene in tobacco is very poor, resulting in infrequent identification of plants toxic to THW. Toxicity is defined by leaf feeding assays as at least 60% mortality of tobacco hornworm neonate larvae with a damage rating of 1 or less (scale is 0 to 4; 0 is equivalent to total protection, 4 total damage). The modified HD-1 gene (pMON5370) shows a large increase in expression (estimated to be approximately 100-fold; see Table VIII) in tobacco. Therefore, increases in expression of the wild-type gene due to indidvidual modifications would be apparently a large increase in the frequency of toxic tobacco plants and the presence of detectable *B.t.k.* protein. Results are shown in the following table:

TABLE IV

Relative effects of Regional Modifications within the B.t.k. Gene

| Construct | Position Modified | # of Plants | # of Toxic Plants |
|---|---|---|---|
| pMON5370 | 185,240,669,930, 1110,1380a + b,1600 | 38 | 22 |
| pMON10707 | 185,240,462,669 | 48 | 19 |
| pMON10706 | 930,1110,1380a + b,1600 | 43 | 1 |
| pMON10539 | 185 | 55 | 2 |
| pM0N10537 | 240 | 57 | 17 |
| PMON10540 | 185,240 | 88 | 23 |
| pMON10705 | 462 | 47 | 1 |

The effects of each individual oligonucleotides' changes on expression did reveal some overall trends. Six different constructs were generated which were designed to identify the key regions. The nine different oligonucleotides were divided in half by their position on the gene. Changes in the N-terminal half were incorporated into pMON10707 (185, 240, 462, 669). C-terminal half changes were incorporated into pMON10706 (930, 1110, 1380a+b, 1600). The results of analysis of plants with these two constructs indicate that pMON10707 produces a substantial number of toxic plants (19 of 48). Protein from these plants is detectable by ELISA analysis. pMON10706 plants were rarely identified as insecticidal (1 of 43) and the Levels of B.t.k. were barely detectable by immunological analysis. Investigation of the N-terminal changes in greater detail was done with 4 pMON constructs; 10539 (185 alone), 10537 (240 alone), 10540 (185 and 240) and 10705 (462 alone). The results indicate that the presence of the changes in 240 were required to generate a substantial number of toxic plants (pMON10540; 23 of 88, pMON10537; 17 of 57). The absence of the 240 changes resulted in a low frequency of toxic plants with low B.t.k. protein levels, identical to results with the wild type gene. These results indicate that the changes in 240 are responsible for a substantial increase in B.t.k. expression levels over an analogous wild-type construct in tobacco. Changes in additional regions (185, 462, 669) in conjunction with 240 may result in increases in B.t.k. expression (>2 fold). However, changes at the 240 region of the N-terminal cortion of the gene do result in dramatic increases in expression.

Despite the importance of the alteration of the 240 region in expression of modified genes, increased expression can be achieved by alteration of other regions. Hybrid genes, part wild-type, part synthetic, were generated to determine the effects of synthetic gene segments on the levels of B.t.k. expression. A hybrid gene was generated with a synthetic N-terminal third (base pair 1 to 590 of FIG. 2: to the XbaI site) with the C-terminal wild type B.t.k. HD-1 (pMON5378) Plants transformed with this vector were as toxic as plants transformed with the modified HD-1 gene (pMON5370). This is consistent with the alteration of the 240 region. However, pMON10538, a hybrid with a wild-type N-terminal third (wild type gene for the first 600 base pairs, to the second XbaI site) and a synthetic C-terminal last two-thirds (base pair 590 to 1845 of FIG. 3 was used to transform tobacco and resulted in a dramatic increase in expression. The levels of expression do not appear to be as high as those seen with the synthetic gene, but are comparable to tne modified gene levels. These results indicate that modification of the 240 segment is not essential to increased expression since pMON10538 has an intact 240 region. A fully synthetic gene is, in most cases, superior for expression levels of B.t.k. (See Example 2.)

EXAMPLE 2

Fully Synthetic B.t.k. HD-1 Gene

A synthetic B.t.k. HD-1 aene was designed using the preferred plant codons listed in Table V below. Table V lists the codons and frequency of use in plant genes of dicotyledonous plants compared to the frequency of their use in the wild type B.t.k. HD-1 gene (amino acids 1–615) and the synthetic gene of this example. The total number of each amino acid in this segment of the gene is listed in the parenthesis under the amino acid designated.

TABLE V

Codon in Usage Synthetic B.t.k. HD-1 Gene

| Amino Acid | Codon | Percent Usage in Plants/Wt B.t.k./Syn | | |
|---|---|---|---|---|
| ARG | CGA | 7 | 11 | 2 |
| (43) | CGC | 11 | 5 | 5 |
|  | CGG | 5 | 2 | 0 |
|  | CGU | 25 | 14 | 27 |
|  | AGA | 29 | 55 | 41 |
|  | AGG | 23 | 14 | 25 |
| LEU | CUA | 8 | 16 | 4 |
| (49) | CUC | 20 | 0 | 20 |
|  | CUG | 10 | 2 | 6 |
|  | CUU | 28 | 22 | 24 |
|  | UUA | 5 | 50 | 0 |
|  | UUG | 30 | 10 | 45 |
| SER | UCA | 14 | 27 | 5 |
| (64) | UCC | 26 | 9 | 28 |
|  | UCG | 3 | 8 | 0 |
|  | UCU | 21 | 19 | 31 |
|  | AGC | 21 | 6 | 32 |
|  | AGU | 15 | 31 | 5 |
| THR | ACA | 21 | 31 | 14 |
| (42) | ACC | 41 | 19 | 53 |
|  | ACG | 7 | 14 | 0 |
|  | ACU | 31 | 36 | 33 |
| PRO | CCA | 45 | 35 | 53 |
| (34) | CCC | 19 | 6 | 12 |
|  | CCG | 9 | 21 | 3 |
|  | CCU | 26 | 38 | 32 |
| ALA | GCA | 23 | 38 | 26 |
| (31) | GCC | 32 | 9 | 29 |
|  | GCG | 3 | 3 | 0 |
|  | GCU | 41 | 50 | 45 |
| GLY | GGA | 32 | 52 | 45 |
| (46) | GGC | 20 | 17 | 15 |
|  | GGG | 11 | 15 | 6 |
|  | GGU | 37 | 15 | 34 |
| ILE | AUA | 12 | 39 | 2 |
| (46) | AUC | 45 | 11 | 67 |
|  | AUU | 43 | 50 | 30 |
| VAL | GUA | 9 | 45 | 3 |
| (38) | GUC | 20 | 5 | 16 |
|  | GUG | 28 | 11 | 37 |
|  | GUU | 43 | 39 | 45 |
| LYS | AAA | 36 | 100 | 33 |
| (3) | AAG | 64 | 0 | 67 |
| ASN | AAC | 72 | 27 | 80 |
| (44) | AAU | 28 | 73 | 20 |
| GLN | CAA | 64 | 77 | 61 |
| (31) | CAG | 36 | 23 | 39 |
| HIS | CAC | 65 | 0 | 80 |
| (10) | CAU | 35 | 100 | 20 |
| GLU | GAA | 48 | 87 | 50 |
| (30) | GAG | 52 | 13 | 50 |
| ASP | GAC | 48 | 17 | 65 |
| (23) | GAU | 52 | 83 | 35 |
| TYR | UAC | 68 | 20 | 72 |
| (25) | UAU | 32 | 80 | 28 |
| CYS | UGC | 78 | 50 | 100 |
| (2) | UGU | 22 | 50 | 0 |
| PHE | UUC | 56 | 17 | 83 |
| (36) | UUU | 44 | 83 | 17 |
| MET | AUG | 100 | 100 | 100 |
| (9) |  |  |  |  |
| TRP | UGG | 100 | 100 | 100 |
| (9) |  |  |  |  |

The resulting synthetic gene lacks ATTTA sequences, contains only one potential polyadenylation site and has a G+C content of 48.5%. FIG. 3 is a comparison of the wild-type HD-1 sequence to the synthetic gene sequence for amino acids 1–615. There is approximately 77% DNA homology between the synthetic gene and the wild-type gene and 356 of the 615 codons have been changed (approximately 60%).

EXAMPLE 3

Synthetic B.t.k. HD-73 Gene

The crystal protein toxin from B.t.k. HD-73 exhibits a higher unit activity against some important agricultural pests. The toxin protein of HD-1 and HD-73 exhibit substantial homology (~90%) in the N-terminal 450 amino acids, but differ substantially in the amino acid region 451–615. Fusion proteins comprising amino acids 1–450 of HD-1 and 451–615 of HD-73 exhibit the insecticidal properties of the wild-type HD-73. The strategy employed was to use the 5'-two thirds of the synthetic HD-1 gene (first 1350 bases, up to the SacI site) and to dramatically modify the final 590 bases (through amino acid 645) of the HD-73 in a manner consistent with the algorithm used to design the synthetic HD-1 gene. Table VI below lists the oligonucleotides used to nodify the HD-73 gene in the order used in the gene from 5' to 3' end. Nine oliconucleotides were used in a 590 base pair region, each nucleotide ranging in size from 33 to 60 bases. The only regions left unchanged were areas where there were no long consecutive strings of A or T bases (longer than six). All polyadenylation sites and ATTA sites were eliminated.

TABLE VI

Mutagenesis Primers for B.t.k. HD-73

| Primer | Length (bp) | Sequence | |
|---|---|---|---|
| 73K1363 | 51 | AATACTATCG TGTTGTTGAA CGGTGTATCC | GATGCGATGA CTCAGCACTA A Sequence ID No. 10 |
| 73K1437 | 33 | TCCTGAAATG TGAAGAGAAA | ACAGAACCGT GTT Sequence ID No. 11 |
| 73K1471 | 48 | ATTTCCACTG TAACGAGGTC AATCCTGG | CTGTTGAGTC TCCACCAGTG Sequence ID No. 12 |
| 73K1561 | 60 | GTGAATAGGG CATACCTCAC TATCTGGTAG | GTCACAGAAG ACGAACTCTA ATGTTGGATGG Sequence ID No. 13 |
| 73K1642 | 33 | TGTACCTGGA AGAAGATGGA | ACTGTATTGG TGA Sequence ID No. 14 |
| 73K1675 | 48 | TTCAAAGTAA TGGATTGGAG GAGGTAGC | CCGAAATCGC ATTATCCAAG Sequence ID No. 15 |
| 73K1741 | 39 | ACTAAAGTTT CGATGTTACC | CTAACACCCA GAGTGAAGA |
| 73K1797 | 36 | AACTGGAATG TGTCGATAAT | AACTCGAATC CACTCC Sequence ID No. 16 |
| 73KTERM | 54 | GGACACTAGA AATCGGTCAC AGTCCAAGCT | TCTTAGTGAT ATTTGTCTTG CGTT |

The resulting gene has two potential polyadenyiation sites (compared to 18 in the WT) and no ATTA sequence (12 in the WT). The G+C content has increased from 37% to 48%. A total of 59 individual base pair changes were made using the primers in Table VI. Overall, there is 90% DNA homology between the region of the HD-73 gene modified by site directed mutagenesis and the wild-type sequence of the analogous region of HD-73. The synthetic HD-73 is a hybrid of the first 1360 bases from the synthetic HD-1 and the next 590 bases or so modified HD-73 sequence. FIG. 4 is a comparison of the above-described synthetic B.t.k. HD-73 and the wild-type B.t.k. HD-73 encoding amino acids 1–645. In the modified region of the HD-73 gene 44 of the 170 codons (25%) were changed as a result of the site-directed mutagenesis changes resulting from the oligonucleotides found in Table VI. Overall, approximately 50% of the codons in the synthetic B.t.k. HD-73 differ from the analogous segment of the wild-type and HD-73 gene.

A one base pair deletion in the synthetic HD-73 gene was detected in the course of sequencing the 3' end at base pair 1890. This results in a frame-shift mutation at amino acid 625 with a premature stop codon at amino acid 640 (pMON5379). Table VII below compares the codon usage of the wild-type gene of B.t.k. HD-73 versus the synthetic gene of this example for amino acids 451–645 and codon usage of naturally occurring genes of dicotyledonous plants. The total number of each amino acid encoded in this segment of the gene is round in the parentheses under the amino acid designation.

TABLE VII

Codon Usage in Synthetic B.t.k. HD-73 Gene

| Amino Acid | Codon | Percent Usage in Plants/Wt HD-73/Syn | | |
|---|---|---|---|---|
| ARG | CGA | 7 | 10 | 0 |
| (10) | CGC | 11 | 0 | 8 |
| | CGG | 5 | 10 | 0 |
| | CGU | 25 | 20 | 23 |
| | AGA | 29 | 60 | 62 |
| | AGG | 23 | 0 | 8 |
| LEU | CUA | 8 | 25 | 8 |
| (12) | CUC | 20 | 17 | 58 |
| | CUG | 10 | 17 | 8 |
| | CUU | 28 | 8 | 0 |
| | UUA | 5 | 33 | 8 |
| | UUG | 30 | 0 | 17 |
| SER | UCA | 14 | 24 | 18 |
| (21) | UCC | 26 | 10 | 27 |
| | UCG | 3 | 10 | 0 |
| | UCU | 21 | 24 | 18 |
| | AGC | 21 | 0 | 14 |
| | AGU | 15 | 33 | 23 |
| THR | ACA | 21 | 47 | 38 |
| (15) | ACC | 41 | 3 | 31 |
| | ACG | 7 | 13 | 0 |
| | ACU | 31 | 27 | 31 |
| PRO | CCA | 45 | 71 | 71 |
| (7) | CCC | 19 | 0 | 0 |
| | CCG | 9 | 4 | 0 |
| | CCU | 26 | 14 | 29 |
| ALA | GCA | 23 | 29 | 31 |
| (14) | GCC | 32 | 7 | 8 |
| | GCG | 3 | 21 | 15 |
| | GCU | 41 | 43 | 46 |
| GLY | GGA | 32 | 33 | 43 |
| (15) | GGC | 20 | 0 | 0 |
| | GGG | 11 | 27 | 14 |
| | GGU | 37 | 40 | 43 |
| ILE | AUA | 12 | 33 | 7 |
| (15) | AUC | 45 | 7 | 40 |
| | AUU | 43 | 60 | 53 |
| VAL | GUA | 9 | 40 | 7 |
| (15) | GUC | 20 | 0 | 7 |
| | GUG | 28 | 20 | 36 |
| | GUU | 43 | 40 | 50 |
| LYS | AAA | 36 | 67 | 100 |
| (3) | AAG | 64 | 33 | 0 |
| ASN | AAC | 72 | 20 | 53 |
| (20) | AAU | 28 | 80 | 47 |
| GLN | CAA | 64 | 60 | 67 |
| (5) | CAG | 36 | 40 | 33 |
| HIS | CAC | 65 | 67 | 100 |
| (3) | CAU | 35 | 33 | 0 |
| GLU | GAA | 48 | 86 | 57 |
| (7) | GAG | 52 | 14 | 43 |
| ASP | GAC | 48 | 40 | 50 |
| (5) | GAU | 52 | 60 | 50 |
| TYR | UAC | 68 | 0 | 20 |
| (5) | UAU | 32 | 100 | 80 |
| CYS | UGC | 78 | 0 | 0 |
| (0) | UGU | 22 | 0 | 0 |

TABLE VII-continued

Codon Usage in Synthetic B.t.k. HD-73 Gene

| Amino Acid | Codon | Percent Usage in Plants/Wt HD-73/Syn | | |
|---|---|---|---|---|
| PHE | UUC | 56 | 8 | 67 |
| (13) | UUU | 44 | 92 | 33 |
| MET | AUG | 100 | 100 | 100 |
| (2) | | | | |
| TRP | UGG | 100 | 100 | 100 |
| (2) | | | | |

Another truncated synthetic HD-73 gene was constructed. The sequence of this synthetic HD-73 gene is identical to that of the above synthetic HD-73 gene in the region in which they overlap (amino acids 29–615), and it also encodes Met-Ala at the N-terminus. FIG. 8 shows a comparison of this truncated synthetic HD-73 gene with the N-terminal Met-Ala versus the wild-type HD-73 gene.

While the previous examples have been directed at the preparation of synthetic and modified genes encoding truncated B.t.k. proteins, synthetic or modified genes can also be prepared which encode full length toxin proteins.

One full length B.t.k. gene consists of the synthetic HD-73 sequence of FIG. 4 from nucleotide 1–1845 plus wild-type HD-73 sequence encoding amino acids 616 to the C-terminus of the native protein. FIG. 9 shows a comparison of this synthetic/wild-type full length HD-73 gene versus the wild-type full length HD-73 gene.

Another full length *B.t.k.* gene consists of the synthetic HD-73 sequence of FIG. 4 from nucleotide 1–1845 plus a modified HD-73 sequence ending amino acids 616 to the C-terminus of the native protein. The C-terminal portion has been modified by site-directed mutagenesis to remove putative polyadenylation signals and ATTTA sequences according to the algorithm of FIG. 1. FIG. 10 shows a comparison of this synthetic/modified full length HD-73 gene versus the wild-type full length HD-73 gene.

Another full length *B.t.k.* gene consists of a fully synthetic HD-73 sequence which incorporates the synthetic HD-73 sequence of FIG. 4 from nucleotide 1–1845 plus a synthetic sequence encoding amino acids 616 to the C-terminus of the native protein. The C-terminal synthetic portion has been designed to eliminate putative polyadenylation signals and ATTTA sequences and to include plant preferred codons. FIG. 11 shows a comparison of this fully synthetic full length HD-73 gene versus the wild-type full length HD-73 gene.

Alternatively, another full length *B.t.k.* gene consists of a fully synthetic sequence comprising base pairs 1–1830 of *B.t.k.* HD-1 (FIG. 3) and base pairs 1834–3534 of *B.t.k.* HD-73 (FIG. 11) (SEQ ID NO:27).

EXAMPLE 4

Expression of Modified and Synthetic *B.t.k.* HD-1 and Synthetic HD-73

A number of plant transformation vectors for the expression of *B.t.k.* genes were constructed by incorporating the structural coding sequences of the previously described genes Into plant transformation cassette vector pMON893. The respective intermediate transformation vector is nserted into a suitable disarmed Agrobacterium vector such as *A. tumefaciens* ACO, supra. Tissue explants are cocultured with the disarmed Agrobacterium vector and plants regenerated under selection for kanamyc n resistance using known protocols: tobacco (Horsch et al., 1985); tomato (McCormick et al., 1986) and cotton (Trolinder et al., 1987).

a) Tobacco.

The level of *B.t.k.* HD-1 protein in transgenic tobacco plants containing pMON9921 (wild type truncated), pMON5370 (modified HD-1, Example 1, FIG. 2) and pMON5377 (synthetic HD-1, Example 2, FIG. 3) were analyzed by Western analysis. Leaf tissue was frozen in liquid nitrogen, ground to a fine powder and then ground in a 1:2 (wt:volume) of SDS-PAGE sample buffer. Samples were frozen on dry ice, then incubated for 10 minutes in a boiling water bath and microfuged for 10 minutes. The protein concentration of the supernatant was determined by the method of Bradford (Anal. Biochem. 72:248–254). Fifty ug of protein was run per lane on 9% SDS-PAGE gels, the protein transferred to nitrocellulose and the *B.t.k.* HD-1 protein visualized using antibodies produced against *B.t.k.* HD-1 protein as the primary antibody and alkaline phosphatase conjugated second antibody as described by the manufacturer (Promega, Madison, Wis.) Purified HD-1 tryptic fragment was used as the control. Whereas the *B.t.k.* protein from tobacco plants containing pMON9921 was below the level of detection, the *B.t.k.* protein from plants containing the modified (pMON5370) and synthetic (pMON5377) genes was easily detected. The *B.t.k.* protein from plants containing pMON9921 remained undetectable, even with 10 sold longer incubation times. The relative levels of *B.t.k.* HD-1 protein in these plants is estimated in Table VIII. Because the protein from plants containing pMON9921 was not observed, the level of protein in these plants was estimated from the relative mRNA levels (see below). Plants containing the modified gene (pMON5370) expressed approximately 100 fold more *B.t.k.* protein than plants containing the wild-type gene (pMON9921). Plants containing the fully synthetic *B.t.k.* HD-1 gene (pMON5377) expressed approximately five fold more protein than plants containing the modified gene. The modified gene contributes the majority of the increase in *B.t.k.* expression observed. The plants used to generate the above data are the best representatives from each construct based either on a tobacco hornworm bioassay or on data derived from previous Western analysis.

TABLE VIII

Expression of B.t.k. HD-1 Protein in Transgenic Tobacco

| Gene Description | Vector | B.t.k. Protein* Concentration | Fold Increase in B.t.k. Expression |
|---|---|---|---|
| Wild type | pMON9921 | 10 | 1 |
| Modified | pMON5370 | 1000 | 100 |
| Synthetic | pMON5377 | 5000 | 500 |

*B.t.k. protein concentrations are expressed in ng/mg of total soluble protein. The level of B.t.k. protein for plants containing the wild type gene are estimated from mRNA levels.

Plants containing these genes were tested for bioactivity to determine whether the increased quantities of protein observed by Western analysis result in a corresponding increase in bioactivity. Leaves from the same plants used for the Western data in Table 1 were tested for bioactivity against two insects. A detacned leaf bioassay was first done using tobacco hornworm, an extremely sensitive lepidopteran insect. Leaves from all three transgenic tobacco plants were totally protected and 100% mortality of tobacco hornworm observed (see Table IX below). A much less sensitive insect, beet armyworm, was then used in another detached leaf bioassay. Beet armyworm is approximately 500 fold less sensitive to B.t.k. HD-1 protein than tobacco hornworm. The difference in sensitivity of these two insects was determined using purified HD-1 protein in a diet incorporation assay (see below). Plants containing the wild-type gene (pMON9921) showed only minimal protection against beet armyworm, whereas plants containing the modified gene showed almost complete protection and plants containing the fully synthetic gene were totally protected against beet armyworm damage. The results of these bioassays confirm the levels of *B.t.k.* HD-1 expression observed in the Western analysis and demonstrates that the increased levels of *B.t.k.* HD-1 protein correlates with increased insecticidal activity.

TABLE IX

Protection of Tobacco Plants from Tobacco Hornworm and Beet Armyworm

| Gene Description | Vector | Tobacco Hornworm Damage* | Beet Armyworm Damage* |
|---|---|---|---|
| None | None | NL | NL |
| Wild type | pMON9921 | 0 | 3 |
| Modified | pMON5370 | 0 | 1 |
| Synthetic | pMON5377 | 0 | 0 |

*Extent of insect damage was rated: 0, no damage; 1, slight; 2, moderate; 3, severe; or NL, no leaf left.

The bioactivity of the *B.t.k.* HD-1 protein produced by these transgenic plants was further investigated to more accurately quantitate the relative activities. Leaf tissue from tobacco plants containing the wild-type, modified and synthetic genes were ground in 100 mM sodium carbonate buffer, pH 10 at a 1:2 (wt:vol) ratio. Particulate material was removed by centrifugation. The supernatant was incorporated into a synthetic diet similar to that described by Marrone et al. (1985). The diet medium was prepared the day of the test with the plant extract solutions incorporated in place of the 20% water component. One ml of the diet was aliquoted into 96 well plates.

After the diet dried, one neonate tobacco budworm larva was added to each well. Sixteen insects were tested with each plant sample. The plants were incubated at 27° C. After seven days, the larvae from each treatment were combined and weighed on an analytical balance. The average weight per insect was calculated and compared to a standard curve relating *B.t.k.* protein concentrations to average larval weight. Insect weight was inversely proportional (in a logarithmic manner) to the relative increase in *B.t.k.* protein concentration. The amount of *B.t.k.* HD-1 protein, based on the extent of larval growth inhibition was determined for two different plants containing each of the three genes. The specific activity (ng of *B.t.k.* HD-1 per mg of plant protein) was determined for each plant. Plants containing the modified HD-1 gene (pMON5370) averaged approximately 1400 ng (1200 and 1600 ng) of *B.t.k.* HD-1 per mg of plant extract protein. This value compares closely with the 1000 ng of *B.t.k.* HD-1 protein per mg of plant extract protein as determined by Western analysis (Table I). *B.t.k.* HD-1 concentrations for the plants containing the synthetic HD-1 gene averaged approximately 8200 ng (7200 and 9200 ng) of *B.t.k.* HD-1 protein per mg of plant extract protein. This number compares well to the 5000 ng of HD-1 protein per mg of plant extract protein estimated by Western analysis. Likewise, plants containing the synthetic gene showed approximately a six-fold higher specific activity than the corresponding plants containing the modified gene for these bioassays. In the Western analysis the ratio was approximately 10 fold, again both are in good agreement. The level of *B.t.k.* protein in plants containing the wild-type HD-1 gene (pMON9921) was too low to give a significant decrease in larval weight and hence was below a level that could be quantitated in this assay. In conclusion, the levels of *B.t.k.* HD-1 protein determined by both the bioassays and the Western analysis for these plants containing the modified and synthetic genes agree, which demonstrates that the *B.t.k.* HD-1 protein produced by these plants is biologically active.

The levels of mRNA were determined in the plants containing the wild-type *B.t.k.* HD-1 gene (pMON9921) and the modified gene (pMON5370) to establish whether the increased levels of protein production result from increased transcription or translation. mRNA from plants containing the synthetic gene could not be analyzed directly with the same DNA probe as used for the wild-type and modified genes because of the numerous changes made in the coding sequence. mRNA was isolated and hybridized with a sinaoe-stranded DNA probe homologous to approximately the 5' 90 bp of the wild-type or modified gene coding sequences. The hybrids were digested with S1 nuclease and the protected probe fragments analyzed by gel electrophoresis. Because the procedure used a large excess of probe and long hybridization time, the amount of protected probe is proportional to the amount of *B.t.k.* mRNA present in the sample. Two plants expressing the modified gene (pMON5370) were found to produce up to ten-fold more RNA than a plant expressing the wild-type gene (pMON9921).

The increased mRNA level from the modified gene is consistent with the result expected from the modifications introduced into this gene. However, this 10 fold increase in mRNA with the modified gene compared to the wild-type gene is in contrast to the 100 fold increase in *B.t.k.* protein from these genes in tobacco plants. If the two mRNAs were equally well translated then a 10 fold increase in stable mRNA would be expected to yield a 10 fold increase in protein. The higher increase in protein indicates that the modified gene mRNA is translated at about a fold higher efficiency than wild-type. Thus, about half of the total effect on gene expression can be explained by changes in mRNA levels and about half to changes in translational efficiency. This increase in translational efficiency is striking in that only about 9.5% of the codons have been changed in the modified gene; that is, this effect is clearly not due to wholesale codon usage changes. The increased translational efficiency could be due to changes in mRNA secondary structure that affect translation or to the removal of specific translational blockades due to specific codons that were changed.

The increased expression seen with the synthetic HD-1 gene was also seen with a synthetic HD-73 gene in tobacco. *B.t.k.* HD-73 was undetected in extracts of tobacco plants containing the wild-type truncated HD-73 gene (pMON5367), whereas *B.t.k.* HD-73 protein was easily detected in extracts from tobacco plants containing the synthetic HD-73 gene of FIG. 4 (pMON5383). Approximately 1000 ng of *B.t.k.* HD-73 protein was detected per mg of total soluble plant protein.

As described in Example 3 above, the *B.t.k.* HD-73 protein encoded in pMON5383 contains a small C-terminal extension of amino acids not encoded in the wild-type HD-73 protein. These extra amino acids had no effect on insect toxicity or on increased plant expression. A second synthetic HD-73 gene was constructed as described in Example 3 (FIG. 8) and used to transform tobacco (pMON5390). Analysis of plants containing pMON5390 showed that this gene was expressed at levels comparable to that of pMON5383 and that these plants had similar insecticidal efficacy.

In tobacco plants the synthetic HD-1 gene was expressed at approximately a 5-fold higher level than the synthetic HD-73 gene. However, this synthetic HD-73 gene still was expressed at least 100-fold better than the wild-type HD-73 gene. The HD-73 protein is approximately 5-fold more toxic to many insect pests than the HD-1 protein, so both synthetic HD-1 and HD-73 genes provide approximately comparable insecticidal efficacy in tobacco.

The full length *B.t.k.* HD-73 genes described in Example 3 were also incorporated into the plant transformation vector pMON893 so that they were expressed from the En 35S promoter. The synthetic/wild-type full length HD-73 gene of FIG. 9 was incorporated into pMON893 to create pMON10505. The synthetic/modified full length HD-73 gene of FIG. 10 was incorporated into pMON893 to create pMON10526. The fully synthetic HD-73 gene of FIG. 11 was incorporated into pMON893 to create pMON10518. These vectors were used to obtain transformed tobacco plants, and the plants were analyzed for insecticidal efficacy and for *B.t.k.* HD-73 protein levels by Western blot or ELISA immunoassay.

Tobacco plants containing all three of these full length *B.t.k.* genes produced detectable *B.t.k.* protein and showed 100% mortality of tobacco hornworm. This result is surprising in light of previous reported attempts to express the full length *B.t.k.* genes in transgenic plants. Vaeck et al. (1987) reported that a full length *B.t.k. berliner* gene similar to our HD-1 gene could not be detectably expressed in tobacco. Barton et al. (1987) reported a similar result for another full length gene from *B.t.k.* HD-1 (the so called 4.5 kb gene), and further indicated that tobacco callus containing this gene became necrotic, indicating that the full length gene product was toxic to plant cells. Fischhoff et al. (1987) reported that the full length *B.t.k.* HD-1 gene in tomato was poorly expressed compared to a truncated gene, and no plants that were fully toxic to tobacco hornworm could be recovered. All three of the above reports indicated much higher expression levels and recovery of toxic plants if the respective *B.t.k.* genes were truncated. Adang et al. reported that the full length HD-73 gene yielded a few tobacco plants with some biological activity (none were highly toxic) against hornworm and barely detectable *B.t.k.* protein. It was also noted by them that the major *B.t.k.* mRNA in these plants was a truncated 1.7 kb species that would not encode a functional toxin. This indicated improper expression of the gene in tobacco. In contrast to all of these reports, the three full length *B.t.k.* HD-73 genes described above all lead to relatively high levels of protein and high levels of insect toxicity.

*B.t.k.* zrotein and mRNA levels in tobacco plants are shown in Table X for these three vectors. As can be seen from the table, the synthetic/wild-type gene (pMON10506) produces *B.t.k.* protein as about 0.01% of total soluble protein; the synthetic/modified gene produces *B.t.k.* as about 0.02% of total soluble protein; and the fully synthetic gene produces *B.t.k.* as about 0.2% of total soluble protein. *B.t.k.* mRNA was analyzed in these plants by Northern blot analysis using the common 5' synthetic half of the genes as a probe. As shown in Table X, the increased protein levels can Largely be attributed to increased mRNA levels. Compared to the truncated modified and synthetic cenes, this could indicate that the major contributors to increased translational efficiency are in the 5' half of the gene while the 3' half of the gene contains mostly determinants of mRNA stability. The increased protein levels also indicate that increasing the amount of the full length gene that is synthetic or modified increases *B.t.k.* protein levels. Compared to the truncated synthetic *B.t.k.* HD-73 genes (pMON5383 or pMON5390), the fully synthetic aene (pMON10518) produces as much or slightly more *B.t.k.* protein demonstrating that the full length genes are capable of being expressed at high levels in plants. These tobacco plants with high levels of full length HD-73 protein show no evidence of abnormality and are fully fertile. The *B.t.k.* protein levels in these plants also produce the expected levels of insect toxicity based on feeding studies with beet armyworm or diet incorporation assays of plant extracts with tobacco budworm. The *B.t.k.* protein detected by Western blot analysis in these tobacco plants often contains a varying amount of protein of about 80 kDa which is apparently a proteolytic fragment of the full length protein. The C-terminal half of the full length protein is known to be proteolytically sensitive, and similar proteolytic fragments are seen from the full length gene in *E. coli* and *B.t.* itself. These fragments are fully insecticidal. The Northern analysis indicated that essentially all of the mRNA from these full length genes was of the expected full length size. There is no evidence of truncated mRNAs that could give rise to the 80 kDa protein fragment. In addition, it is possible that the fragment Is not present in intact plant cells and is merely due to proteolysis during extraction for immunoassay.

TABLE X

Full Leneth B.t.k. HD-73 Protein and mRNA Levels in Transgenic Tobacco Plants

| Gene description | Vector | B.t.k. protein concentration | Relative B.t.k. mRNA level |
| --- | --- | --- | --- |
| Synthetic/wild type | pMON10506 | >100 | 0.5 |
| Synthetic/modified | pMON10526 | 400 | 1 |
| Fully synthetic | pMON10518 | >2000 | 40 |

Thus, there is no serious impediment to producing high levels of *B.t.k.* HD-73 protein in plants from synthetic genes, and this is expected to be true of other full length lepidopteran active genes such as *B.t.k.* HD-1 or *B.t.* entomocidus. The fully synthetic *B.t.k.* HD-1 gene of Example 3 has been assembled in plant transformation vectors such as pMON893.

The fully synthetic gene in pMON10518 was also utilized in another plant vector and analyzed in tobacco plants. Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it may be advantageous to increase the expression of *B.t.* protein in these tissues over that obtained with the CaMV35S promoter.

The 35S promoter of Figwort Mosaic Virus (FMV) is analogous to the CaMV35S promoter. This promoter has been isolated and engineered into a plant transformation vector analogous to pMON893. Relative to the CaMV promoter, the FMV 35S promoter is highly expressed in the floral tissue, while still providing similar high levels of gene expression in other tissues such as leaf. A plant transformation vector, pMON10517, was constructed in which the full length synthetic *B.t.k.* HD-73 gene of FIG. 11 was driven by the FMV 35S promoter. This vector is identical to pMON10518 of Example 3 except that the FMV promoter is substituted for the CaMV promoter. Tobacco plants transformed with pMON10517 and pMON10518 were obtained and compared for expression of the B.t.k. protein by Western blot or ELISA immunoassay in leaf and floral tissue. This analysis showed that pMON10517 containing the FMV promoter expressed the full length HD-73 protein at higher levels in floral tissue than pMC10518 containing the CaMV promoter. Expression of the full length B.t.k. HD-73 protein from pMON10517 in leaf tissue is comparable to that seen with the most highly expressing plants containing pMON10518. However, when floral tissue was analyzed, tobacco plants containing pMON10518 that had high levels of B.t.k. protein in leaf tissue did not have detectable B.t.k. protein in the flowers. On the other hand, flowers of tobacco plants containing pMON10517 had levels of B.t.k. protein nearly as high as the levels in leaves at approximately 0.05% of total soluble protein. This analysis showed that the FMV promoter could be used to produce relatively high levels of B.t.k. protein in floral tissue compared to the CaMV promoter.

b) Tomato.

The wild-type, modified and synthetic *B.t.k.* HD-1 genes tested in tobacco were introduced into other plants to demonstrate the broad utility of this invention. Transgenic tomatoes were produced which contain these three genes. Data show that the increased expression observed with the modified and synthetic gene in tobacco also extends to tomato. Whereas the *B.t.k.* HD-1 protein is only barely detectable in plants containing the wild type HD-1 gene (pMON9921), *B.t.k.* HD-1 was readily detected and the levels determined for plants containing the modified (pMON5370) or synthetic (pMON5377) genes. Expression levels for the plants containing the wild-type, modified and synthetic HD-1 genes were approximately 10, 100 and 500 ng per mg of total plant extract see Table XI below). The Increase in *B.t.k.* HD-1 protein for the modified gene accounted for the majority or increase observed; 10 fold higher than the plants containing the wild-type gene, compared to only an additional five-fold increase for plants containing the synthetic gene. Again the site-directed changes made in the modified gene are the mdajor contributors to the increased expression of *B.t.k.* HD-1.

TABLE XI

B.t.k. HD-1 Expression in Transgenic Tomato Plants

| Gene Description | Vector | B.t.k. Protein* Concentration | Fold Increase in B.t.k. Expression |
|---|---|---|---|
| Wild type | pMON9921 | 10 | 1 |
| Modified | pMON5370 | 100 | 10 |
| Synthetic | pMON5377 | 500 | 50 |

*B.t.k. HD-1 protein concentrations are expressed in ng/mg of total soluble plant protein. Data for plants containing the wild-type gene are estimates from mRNA levels and protein levels determined by ELISA.

These differences in *B.t.k.* HD-1 expression were confirmed with bioassays against tobacco hornworm and beet armyworm. Leaves from tomato plants containing each of these genes controlled tobacco hornworm damage and produced 100% mortality. With beet armyworm, leaves from plants containing the wild-type HD-1 gene (pMON9921) showed significant damage, leaves from plants containing the modified gene (pMON5370) showed less damage and leaves from plants containing the synthetic aene (pMON5377) were completely protected (see Table XII below).

TABLE XII

Protection of Tomato Plants from Tobacco Hornworm and Beet Armyworm

| Gene Description | Vector | Tobacco Hornworm Damage* | Beet Armyworm Damage* |
|---|---|---|---|
| None | None | NL | NL |
| Wild type | pMON9921 | 0 | 3 |
| Modified | pMON5370 | 0 | 1 |
| Synthetic | pMON5377 | 0 | 0 |

*Damage was rated as shown in Table IX.

The generality of the synthetic gene approach was extended in tomato with a synthetic *B.t.k.* HD-73 gene.

In tomato, extracts from plants containing the wild-type truncated HD-73 gene (pMON5367) showed no detectable HD-73 protein. Extracts from plants containing the synthetic HD-73 gene (pMON5383) showed high levels of *B.t.k.* HD-73 protein, approximately 2000 ng per mg of plant extract protein. These data clearly demonstrate that the changes made in the synthetic HD-73 gene lead to dramatic increases in the expression of the HD-73 protein in tomato as well as in tobacco In contrast to tobacco, the synthetic HD-73 gene in tomato is expressed at approximately 4-fold to 5-fold higher levels than the synthetic HD-1 gene. Because the HD-73 protein is about 5-fold more active than the HD-1 protein against many insect pests including Heliothis species, the increased expression of synthetic HD-73 compared to synthetic HD-1 corresponds to about a 25-fold increased insecticidal efficacy in tomato.

In order to determine the mechanisms involved in the increased expression of modified and synthetic *B.t.k.* HD-1 genes in tomato, S1 nuclease analysis of mRNA levels from transformed tomato plants was performed. As indicated above, a similar analysis had been performed with tobacco plants, and this analysis showed that the modified gene produced up to 10-fold more mRNA than the wild-type gene. The analysis in tomato utilized a different DNA probe that allowed the analysis of wild-type (pMON9921), modified (pMON5370) and synthetic (pMON5377) HD-1 genes with the same probe. This probe was derived from the 5' untranslated region of the CaMV35S promoter in pMON893 that was common to all three of these vectors (pMON9921, pMON5370 and pMON5377). This S1 analysis indicated that *B.t.k.* mRNA levels from the modified gene were 3 to 5 fold higher than for the wild-type gene, and that mRNA levels for the synthetic gene were about 2 to 3 fold higher than for the modified gene. Three independent transformants were analyzed for each gene. Compared to the fold increases in *B.t.k.* HD-1 protein from these genes in tomato shown in Table XI, these mRNA increases can explain about half of the total protein increase as was seen in tobacco for the wild-type and modified genes. For tomato the total mRNA increase from wild-type to synthetic is about 6 to 15 fold compared to a protein increase of about 50 fold. This result is similar to that seen for tobacco in comparing the wild-type and modified genes, and it extends to the synthetic gene as well. That is, about half of the total fold increase in *B.t.k.* protein from wild-type to modified genes can be explained by mRNA increases and about half to enhanced translational efficiency. The same is also true in comparing the modified gene to the synthetic gene. Although there is an additional increase in RNA levels, this mRNA increase can explain only about half of the total protein increase.

The full length *B.t.k.* genes described above were also used to transform tomato plants and these plants were analyzed for *B.t.k.* protein and insecticidal efficacy. The results of this analysis are shown in Table XIII. Plants containing the synthetic/wild-type gene (pMON10506) produce the *B.t.k.* HD-73 protein at levels of about 0.01% of their total soluble protein.

Plants containing the synthetic/modified gene (pMON10526) produce about 0.04% *B.t.k.* protein, and plants containing the fully synthetic gene (pMON10518) produce about 0.2% *B.t.k.* protein. These results are very similar to the tobacco plant results for the same genes. mRNA levels estimated by Northern blot analysis in tomato also increase in parallel with the protein level increase. As for tobacco with these three genes, most of the protein increase can be attributed to increased mRNA with a small component of translational efficiency increase indicated for the fully synthetic gene. The highest levels of full length *B.t.k.* protein (from pMON10158) are comparable to or just slightly lower than the highest levels observed for the truncated HD-73 genes (pMON5383 and pMON5390). Tomato plants expressing these full length genes have the insecticidal activity expected for the observed protein levels as determined by feeding assays with beet armyworm or by diet incorporation of plant extracts with tobacco hornworm.

TABLE XIII

Full Length B.t.k. HD-73 Protein and mRNA Levels in Transgenic Tomato Plants

| Gene description | Vector | B.t.k. protein concentration | Relative B.t.k. mRNA level |
|---|---|---|---|
| Synthetic/wild type | pMON10506 | 100 | 1 |
| Synthetic/modified | pMON10526 | 400 | 2–4 |
| Fully synthetic | pMON10518 | 2000 | 10 | c) Cotton.

The generality of the increased expression of *B.t.k.* HD-1 and *B.t.k.* HD-73 by use of the modified and synthetic genes was extended to cotton. Transgenic calli were produced which contain the wild type (pMON9921) and the synthetic HD-1 (pMON5377) genes. Here again the *B.t.k.* HD-1 protein produced from calli containing the wild-type gene was not detected, whereas calli containing the synthetic HD-1 gene expressed the HD-1 protein at easily detectable levels. The HD-1 protein was produced at approximately 1000 ng/mg of plant calli extract protein. Again, to ensure that the protein produced by the transgenic cotton calli was biologically active and that the increased expression observed with the synthetic gene translated to increased biological activity, extracts of cotton calli were made in similar manner as described for tobacco plants, except that the calli was first dried between Whatman filter paper to remove as much of the water as possible. The dried calli were then ground in liquid nitrogen and ground in 100 mM sodium carbonate buffer, pH 10. Approximately 0.5 ml aliquotes of this material was applied to tomato leaves with a paint brush. After the leaf dried, five tobacco hornworm larvae were applied to each of two leaf samples. Leaves painted with extract from control calli were completely destroyed. Leaves painted with extract from calli containing the wild-tvpe HD-1 gene (pMON9921) showed severe damage. Leaves painted with extract from calli containing the synthetic HD-1 gene (pMONS5377) showed no damage (see Table XIV below).

TABLE XIV

Protection against Tobacco Hornworm by Tomato Leaves Painted with Extracts Prepared from Cotton Calli Containing a Control, the Wild-Type B.t.k. HD-1 Gene, Synthetic HD-1 Gene or Synthetic HD-73 Gene

| Gene Description | Vector | Tobacco Hornworm Damage* |
|---|---|---|
| Control | Control | NL |
| Wild type HD-1 | pMON9921 | 3 |
| Synthetic HD-1 | pMON5377 | 0 |
| Synthetic HD-73 | pMON5383 | 0 |

*Damage was rated as shown in Table VIII.

Cotton calli were also produced containing another synthetic gene, a gene encoding *B.t.k.* HD-73. The preparation of this gene is described in Example 3. Cali containing the synthetic HD-73 gene produced the corresponding HD-73 protein at even higher levels than the calli which contained the synthetic HD-1 gene. Extracts made from calli containing the HD-73 synthetic gene (pMON5383) showed complete control of tobacco hornworm when painted onto tomato leaves as described above for extracts containing the HD-1 protein. (See Table XIV).

Transgenic cotton plants containing the synthetic *B.t.k.* HD-1 gene (pMON5377) or the synthetic *B.t.k.* HD-73 gene (pMON5383) have also been examined. These plants produce the HD-1 or HD-73 proteins at levels comparable to that seen in cotton callus with the same genes and comparable to tomato and tobacco plants with these genes. For either synthetic truncated HD-1 or HD-73 genes, cotton plants expressing *B.t.k.* protein at 1000 to 2000 ng/mg total protein (0.1% to 0.2%) were recovered at a high frequency. Insect feeding assays were performed with leaves from cotton plants expressing the synthetic HD-1 or HD-73 genes. These leaves showed no damage (rating of 0) when challenged with larvae of cabbage looper (*Trichoplusia ni*), and only slight damage when challenged with larvae of beet armyworm (*Spodoptera exigua*). Damage ratings are as defined in Table VIII above. This demonstrated that cotton plants as well as calli expressed the synthetic HD-1 or HD-73 genes at high levels and that those plants were protected from damage by Lepidopteran insect larvae.

Transgenic cotton plants containing either the synthetic truncated HD-1 gene (pMON5377) or the synthetic truncated HD-73 gene (pMON5383) were also assessed for protection against cotton bollworm at the whole plant level in the greenhouse. This is a more realistic test of the ability of these plants to produce an agriculturally acceptable level of control. The cotton bollworm (*Heliothis zea*) is a major pest of cotton that produces economic damage by destroying terminals, squares and bolls, and protection of these fruiting bodies as well as the leaf tissue will be important for effective insect control and adequate crop protection. To test the protection afforded to whole plants, R1 progeny of cotton plants expressing high levels of either *B.t.k.* HD-1 (pMON5377) or *B.t.k.* HD-73 (pMON5383) were assayed by applying 10–15 eggs of cotton bollworm per boll or square to the 20 uppermost squares or bolls on each plant. At least 12 plants were analyzed per treatment. The hatch rate of the eggs was approximately 70%. This corresponds to very high insect pressure compared to numbers of larvae per plant seen under typical field conditions. Under these conditions 100% of the bolls on control cotton plants were destroyed by insect damage. For the transgenics, significant boll protection was observed. Plants containing pMON5377 (HD-1) had 70–75% of the bolls survive the intense pressure of this assay. Plants containing pMON5383 (HD-73) had 80% to 90% boll protection. This is likely to be a consequence of the higher activity of HD-73 protein against cotton bollworm compared to HD-1 protein. In cases where the transgenic plants were damaged by the insects, the surviving larvae were delayed in their development by at least one instar.

Therefore, the increased expression obtained with the modified and synthetic genes is not limited to any one crop; tobacco, tomato and cotton calli and cotton plants all showed drastic increases in *B.t.k.* expression when the plants/calli were produced containing the modified or synthetic genes. Likewise, the utility of changes made to produce the modified and synthetic *B.t.k.* HD-1 gene is not limited to the HD-1 gene. The synthetic HD-73 gene in all three species also showed drastic increases in expression.

In summary, it has been demonstrated that: (1) the genetic changes made in the HD-1 modified gene lead to very significant increases in *B.t.k.* HD-1 expression; (2) production of a totally synthetic gene lead to a further five-fold increase in *B.t.k.* HD-1 expression; (3) the changes incorporated into the modified HD-1 gene accounted for the majority of the increased *B.t.k.* expression observed with the synthetic gene; (4) the increased expression was demonstrated in three different plants—tobacco plants, tomato plants and cotton calli and cotton plants; (5) the increased expression as observed by Western analysis also correlated with similar increases in bioactivity, showing that the *B.t.k.* HD-1 proteins produced were comparably active; (6) when the method of the present invention used to design the synthetic HD-1 gene was employed to design a synthetic HD-73 gene it also was expressed at much higher levels in tobacco, tomato and mo cotton than the wild-type equivalent gene with consequent increases in bioactivity; (7) a fully synthetic full length *B.t.k.* gene was expressed at levels comparable to synthetic truncated genes.

EXAMPLE 5

Synthetic *B.t. tenebrionis* Gene in Tobacco, Tomato and Potato

Referring to FIG. 12, a synthetic gene encoding a Coleopteran active toxin is prepared by making the indicated changes in the wild-type gene of *B.t. tenebrionis* or de novo synthesis of the synthetic structural gene. The synthetic gene is inserted into an intermediate plant transformation vector such as pMON893: Plasmid pMON893 containing the synthetic *B.t.t.* gene is then inserted into a suitable disarmed Agrobacterium strain such as *A. tumefaciens* ACO.

Transformation and Regeneration of Potato

Sterile shoot cultures of Russet Burbank are maintained in vials containing 10 ml of PM medium (Murashige and Skoog (MS) inorganic salts, 30 g/l surcose, 0.17 g/l $NaH_2PO_4H_2O$, 0.4 mg/l thiamine-HC1, and 100 mg/l myo-inositol, solidified with 1 g/1 Gelrite at pH 6.0). When shoots reached approximately 5 cm in length, stem internode segments of 7–10 mm are excised and smeared at the cut ends with a disarmed *Agrobacterium tumefaciens* vector containing the synthetic *B.t.t.* gene from a four day old plate culture. The stem explants are co-cultured for three days at 23° C. on a sterile filter paper placed over 1.5 ml of a tobacco cell feeder layer overlaid on 1/10 P medium (1/10 strength MS inorganic salts and organic addenda without casein as in Jarret et al. (1980), 30 g/l surcose and 8.0 g/l agar). Following co-culture the explants are transferred to full strength P-1 medium for callus induction, composed of MS inorganic salts, organic additions as in Jarret et al. (1980) with the exception of casein, 3.0 mg/l benzyladenine (BA), and 0.01 mg/1 naphthaleneacetic acid (NAA) (Jarret, et al., 1980). Carbenicillin (500 mg/l) is included to inhibit bacterial growth, and 100 mg/l kanamycin is added to select for transformed cells. After four weeks the explants are transferred to medium of the same composition but with 0.3 mg/l gibberellic acid (GA3) replacing the BA and NAA (Jarret et al., 1981) to promote shoot formation. Shoots begin to develop approximately two weeks after transfer to shoot induction medium; these are excised and transferred to vials of PM medium for rooting. Shoots are tested for kanamycin resistance conferred by the enzyme neomycin phosphotransferase II, by placing a section of the stem onto callus induction medium containing MS organic and inorganic salts, 30 g/l surcose, 2.25 mg/l BA, 0.186 mg/l NAA, 10 mg/l GA3 (Webb, et al., 1983) and 200 mg/l kanamycin to select for transformed cells.

The synthetic *B.t.t.* gene described in FIG. 12, was placed into a plant expression vector as descibed in example 5. The plasmid has the following characteristics; a synthetic BglII fragment having approximately 1800 base pairs was inserted into pMON893 in such a manner that the enhanced 35S promoter would express the *B.t.t.* gene. This construct, pMON1982, was used to transform both tobacco and tomato. Tobacco plants, selected as kanamycin resistant plants were screened with rabbit anti-*B.t.t.* antibody. Cross-reactive material was detected at levels predicted to be suitable to cause mortality to CPB. These target insects will not feed on tobacco, but the transgenic tobacco plants do demonstrate that the synthetic gene does improve expression of this protein to detectable levels.

Tomato plants with the pMON1982 construct were determined to produce *B.t.t.* protein at levels insecticidal to CPB. In initial studies, the leaves of four plants (5190, 5225, 5328 and 5133) showed little or no damage when exposed to CPB larvae (damage rating of 0–1 on a scale of 0 to 4 with 4 as no leaf remaining). Under these conditions the control leaves were completely eaten. Immunological analysis of these plants confirmed the presence of material cross-reactive with anti-*B.t.t.* antibody. Levels of protein expression in these plants were estimated at aproximately 1 to 5 ng of *B.t.t.* protein in 50 ug of total extractable protein. A total of 17 tomato plants (17 of 65 tested) have been identified which demonstrate protection of leaf tissue from CPB (rating of 0 or 1) and show good insect mortality.

Results similar to those seen in tobacco and tomato with pMON1982 were seen with pMON1984 in the same plant species. pMON1984 is identical to pMON1982 except that the synthetic protease inhibitor (CMTI) is fused upstream of the native croteolvtic cleavage site. Levels of expression in tobacco were estimated to be similar to pMON1982, between 10–15 ng per 50ug of total soluble protein.

Tomato plants expressing pMON1984 have been identified which protect the leaves from ingestion by CPB. The damage rating was 0 with 100% insect mortality.

Potato was transformed as described in example 5 with a vector similar to pMON1982 containing the enhanced CaMV35S/synthetic *B.t.t.* gene. Leaves of potato plants transformed with this vector, were screened by CPB insect bioassay. Of the 35 plants tested, leaves from 4 plants, 16a, 13c, 13d, and 23a were totally protected when challenged. Insect bioassays with leaves from three other plants, 13e, 1a, and 13b, recorded damage levels of 1 on a scale of 0 to 4 with 4 being total devestation of the leaf material. Immunological analysis confirmed the presence of *B.t.t.* cross-reactive material in the leaf tissue. The level of B.t.t. protein in leaf tissue of plant 16a (damage rating of 0) was estimated at 20–50 ng of B.t.t. protein/50 ug of total soluble protein. The levels of B.t.t. protein seen in 16a tissue was consistent with its biological activity. Immunological analysis of 13e and 13b (tissue which scored 1 in damage rating) reveal less protein (5–10 ng/50 ug of total soluble protein) than in plant 16a. Cuttings of plant 16a were challenged with 50 to 200 eggs of CPB in a whole plant assay. Under these conditions 16a showed no damage and 100% mortality of insects while control potato plants were heavily damaged.

EXAMPLE 6

Synthetic B.t.k. P2 Protein Gene

The P2 protein is a distinct insecticidal protein produced by some strains of B.t. including B.t.k. HD-1. It is characterized by its activity against both lepidopteran and dipteran insects (Yamamoto and Iizuka, 1983). Genes encoding the P2 protein have been isolated and characterized (Donovan et al., 1988). The P2 proteins encoded by these genes are approximately 600 amino acids in length. These proteins share only limited homology with the lepidopteran specific P1 type proteins, such as the B.t.k. HD-1 and HD-73 proteins described in previous examples.

The P2 proteins have substantial activity against a variety of lepidopteran larvae including cabbage looper, tobacco hornworm and tobacco budworm. Because they are active against agronomically important insect pests, the P2 proteins are a desirable candidate in the production of insect tolerant transgenic plants either alone or in combination with the other B.t. toxins described in the above examples. In some plants, expression of the P2 protein alone might be sufficient to provide protection against damaging insects. In addition, the P2 proteins might provide protection against agronomically important dipteran pests. In other cases, expression of P2 together with the B.t.k. HD-1 or HD-73 protein might be preferred. The P2 proteins should provide at least an additive level of insecticidal activity when combined with the crystal protein toxin of B.t.k. HD-1 or HD-73, and the combination may even provide a synergistic activity. Although the mode of action of the P2 protein is unknown, its distinct amino acid sequence suggests that it functions differently from the B.t.k. HD-1 and HD-73 type of proteins. Production of two insect tolerance proteins with different modes of action in the same plant would minimize the potential for development of insect resistance to B.t. proteins in plants. The lack of substantial DNA homology between P2 genes and the HD-1 and HD-73 genes minimizes the potential for recombination between multiple insect tolerance genes in the plant chromosome. The genes encoding the P2 protein although distinct in sequence from the B.t.k. HD-1 and HD-73 genes share many common features with these genes. In particular, the P2 protein genes have a high A+T content (65%), multiple potential polyadenylation signal sequences (26) and numerous ATTTA sequences (10). Because of its overall similarity to the poorly expressed wild-type B.t.k. HD-1 and HD-73 genes, the same problems are expected in expression of the wild-type P2 gene as were encountered with the previous examples. Based on the above-described method for designing the synthetic B.t. genes, a synthetic P2 gene has been designed which gene should be expressed at adequate levels for protection in plants. A comparision of the wild-type and synthetic P2 genes is shown in FIG. 13.

EXAMPLE 7

Synthetic B.t. Entomocidus Gene

The B.t. entomocidus ("Btent") protein is a distinct insecticidal protein produced by some strains of B.t. bacteria. It is characterized by its high level of activity against some lepidopterans that are relatively insensitive to B.t.k. HD-1 and HD-73 such as Spodoptera species including beet armyworm (Visser et al., 1988). Genes encoding the Btent protein have been isolated and characterized (Honee et al, 1988). The Btent proteins encoded by these genes are approximately the same length as B.t.k. HD-1 and HD-73. These proteins share only 68% amino acid homology with the B.t.k. HD-1 and HD-73 proteins. It is likely that only the N-terminal half of the Btent protein is required for insecticidal activity as is the case for HD-1 and HD-73. Over the first 625 amino acids, Btent shares only 38% amino acid homology with HD-1 and HD-73.

Because of their higher activity against Spodoptera species that are relatively insensitive to HD-1 and HD-73, the Btent proteins are a desirable candidate for the production of insect tolerant transgenic plants either alone or in combination with the other B.t. toxins described in the above examples. In some plants production of Btent alone might be sufficient to control the agronomically important pests. In other plants, the production of two distinct insect tolerance proteins would provide protection against a wider array of insects. Against those insects where both proteins are active, the combination of the B.t.k. HD-1 or HD-73 type protein plus the Btent protein should provide at least additive insecticidal efficacy, and may even provide a synergistic activity. In addition, because of its distinct amino acid sequence, the Btent protein may have a different mode of action than HD-1 or HD-73. Production of two insecticidal proteins in the same plant with different modes of action would minimize the potential for development of insect resistance to B.t. proteins in plants. The relative lack of DNA sequence homology with the B.t.k. type genes minimizes the potential for recombination between multiple insect tolerance genes in the plant chromosome.

The genes encoding the Btent protein although distinct in sequence from the B.t.k. HD-1 and HD-73 genes share many common features with these genes. In particular, the Btent protein genes have a high A+T content (62%), multiple potential polyadenylation signal sequences (39 in the full length coding sequence and 27 in the first 1875 nucleotides that is likely to encode the active toxic fragment) and numerous ATTTA sequences (16 in the full length coding sequence and 12 in the first 1875 nucleotides) Because of its overall similarity to the poorly expressed wild type B.t.k. HD-1 and HD-73 genes, the wild-type Btent genes are expected to exhibit similar problems in expression as were encountered with the wild-type HD-1 and HD-73 genes. Based on the above-described method used for designing the other synthetic B.t. genes, a synthetic Btent gene has been designed which gene should be expressed at adequate levels for protection in plants. A comparision of the wild type and synthetic Btent genes is shown in FIG. 14.

EXAMPLE 8

Synthetic B.t.k. Genes for Expression in Corn

High level expression of heterologous genes in corn cells has been shown to be enhanced by the presence of a corn gene intron (Callis et al., 1987). Typically these introns have been located in the 5' untranslated region of the chimeric gene. It has been shown that the CaMV35S promoter and the NOS 3' end function efficiently in the expression of heterologous genes in corn cells (Fromm et al., 1986).

Figure 15:
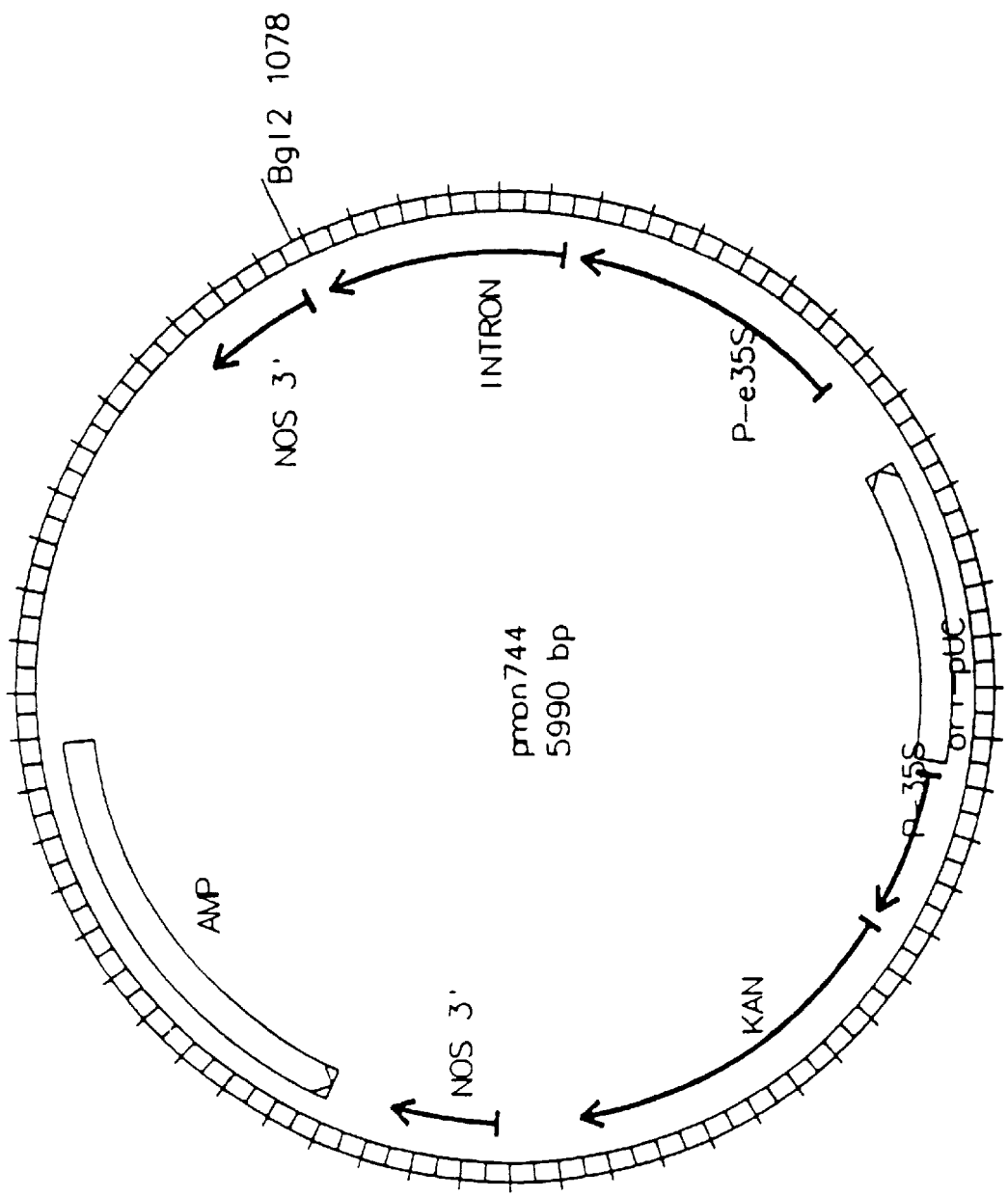
FIG. 15 illustrates a plasmid map for plant expression cassette vector pMON744.

Referring to FIG. 15, a plant expression cassette vector (pMON744) was constructed that contains these sequences.

Specifically the expression cassette contains the enhanced CaMV 35S promoter followed by intron 1 of the corn Adh1 gene (Callis et al., 1987). This is followed by a multilinker cloning site for insertion of coding sequences; this multilinker contains a BglII site among others. Following the multilinker is the NOS 3' end. pMON744 also contains the selectable marker gene 35S/NPTII/NOS 3' for kanamycin selection of transgenic corn cells. In addition, pMON744 has an *E. coli* origin of replication and an ampicillin resistance gene for selection of the plasmid in *E. coli*.

Five *B.t.k.* coding sequences described in the previous examples were inserted into the BglII site of pMON744 for corn cell expression of *B.t.k.* The coding sequences inserted and resulting vectors were:

1. Wild type *B.t.k.* HD-1 from pMON9921 to make pMON8652.
2. Modified *B.t.k.* HD-1 from pMON5370 to make pMON8642.
3. Synthetic *B.t.k.* HD-1 -from pMON5377 to make pMON8643.
4. Synthetic *B.t.k.* HD-73 from pMON5390 to make pMON8644.
5. Synthetic full length *B.t.k.* HD-73 from pMON10518 to make pMON10902.

pMON8652 (wild-type *B.t.k.* HD-1) was used to transform corn cell protoplasts and stably transformed kanamycin resistant callus was isolated. *B.t.k.* mRNA in the corn cells was analyzed by nuclease S1 protection and found to be present at a level comparable to that seen with the same wild-type coding sequence (pMON9921) in transgenic tomato plants.

pMON8652 and pMON8642 (modified HD-1) were used to transform corn cell protoplasts in a transient expression system. The level of *B.t.k.* mRNA was analyzed by nuclease S1 protection. The modified HD-1 gave rise to a several fold increase in *B.t.k.* mRNA compared to the wild-type coding sequence in the transiently transformed corn cells. This indicated that the modifcations introduced into the *B.t.k.* HD-1 gene are capable of enhancing *B.t.k.* expression in monocot cells as was demonstrated for dicot plants and cells.

pMON8642 (modified HD-1) and pMON8643 (synthetic HD-1) were used to transform Black Mexican Sweet (BMS) corn cell protoplasts by PEG-mediated DNA uptake, and stably transformed corn callus was selected by growth on kanamycin containing plant growth medium. Individual callus colonies that were derived from single transformed cells were isolated and propagated separately on kanamycin containing medium.

To assess the expression of the *B.t.k.* genes in these cells, callus samples were tested for insect toxicity by bioassay against tobacco hornworm larvae. For each vector, 96 callus lines were tested by bioassay. Portions of each callus were placed on sterile water agar plates, and five neonate tobacco hornworm larvae were added and allowed to feed for 4 days. For pMON8643, 100% of the larvae died after feeding on 15 of the 96 calli and these calli showed little feeding damage. For pMON8642, only 1 of the 96 calli was toxic to the larvae. This showed that the *B.t.k.* gene was being expressed in these samples at insecticidal levels. The observation that significantly more calli containing pMON8643 were toxic than for pMON8642 showed that significantly higher levels of expression were obtained when the synthetic HD-1 coding sequence was contained in corn cells than when the modified HD-1 coding sequence was used, similar to the previous examples with dicot plants. A semiquantitative immunoassay showed that the pMON8643 toxic samples had significantly higher *B.t.k.* protein levels than the pMON8642 toxic sample.

The 16 callus samples that were toxic to tobacco hornworm were also tested for activity against European corn borer. European corn borer is approximately 40-fold less sensitive to the HD-1 gene product than is tobacco hornworm. Larvae of European corn borer were applied to the callus samples and allowed to feed for 4 days. Two of the 16 calli tested, both of which contained pMON8643 (synthetic HD-1), were toxic to European corn borer larvae.

To assess the expression of the *B.t.k.* genes in differentiated corn tissue, another method of DNA delivery was used. Young leaves were excised from corn plants, and DNA samples were delivered into the leaf tissue by microprojectile bombardment. In this system, the DNA on the microprojectiles is transiently expressed in the leaf cells after bombardment. Three DNA samples were used, and each DNA was tested in triplicate.

1. pMON744, the corn expression vector with no *B.t.k.* gene.
2. pMON8643 (synthetic HD-1).
3. pMON752, a corn expression vector for the GUS gene, no *B.t.k.* gene.

The leaves were incubated at room temperature for 24 hours. The pMON752 samples were stained with a substrate that allows visual detection of the GUS gene product. This analysis showed that over one hundred spots in each sample were expressing the GUS product and the the triplicate samples showed very similar levels of GUS expression. For the pMON744 and pMON8643 samples 5 larvae of tobacco hornworm were added to each leaf and allowed to feed for 48 hours. All three samples bombarded with pMON744 showed extensive feeding damage and no larval mortality. All three samples bombarded with pMON8643 showed no evidence of feeding damage and 100% larval mortality. The samples were also assayed for the presence of *B.t.k.* protein by a qualitative immunoassay. All of the pMON8643 samples had detectable *B.t.k.* protein. These results demonstrated that the the synthetic *B.t.k.* gene was expressed in differentiated corn plant tissue at insecticidal levels.

EXAMPLE 9

Synthetic Potato Leaf Roll Virus Coat Protein Gene

Expression in plants of the coat protein genes from a variety of plant viruses has proven to be an effective method of engineering resistance to these viruses. In order to achieve virus resistance, it is important to express the viral coat protein at an effective level. For many plant virus coat protein genes, this has not proved to be a problem. However, for the coat protein gene from potato leaf roll virus (PLRV), expression of the coat protein has been observed to be low relative to other coat protein genes, and this lower level of protein has not led to optimal resistance to PLRV.

The gene for PLRV coat protein 4s shown in FIG. 16. Referring to FIG. 16, the upper line of sequence shows the gene as it was originally engineered for plant expression in vector pMON893. The gene was contained on a 749 nucleotide BglII-EcoRI fragment with the coding sequence contained between nucleotides 20 and 643. This fragment also contained 19 nucleotides of 5' noncoding sequence and 104 nucleotides of 3' noncoding sentence. This PLRV coat protein gene was relatively poorly expressed in plants compared to other viral coat protein genes.

A synthetic gene was designed to improve plant expression of the PLRV coat protein. Referring again to FIG. 16, the changes made in the synthetic PLRV gene are shown in the lower line. This gene was designed to encode exactly the same protein as the naturally occurring gene. Note that the beginning of the synthetic gene is at nucleotide 14 and the end of the sequence is at nucleotide 654. The coding sequence for the synthetic gene is from nucleotide 20 to 643 of the figure. The changes indicated just upstream and downstream of these endpoints serve only to introduce convenient restriction sites just outside the coding sequence. Thus the size of the synthetic gene is 641 nucleotides which is smaller than the naturally occurring gene. The synthetic gene is smaller because substantially all of the noncoding sequence at both the 5' and 3' ends, except for segments encoding the BglII and EcoRI restriction sites has been removed.

The synthetic gene differs from the naturally occurring gene n two main respects. First, 41 individual ccdons within the coding sequence have been changed to remove nearly all codons for a given amino acid that constitute less than about 15% of the codons for that amino acid in a survey of dicot plant genes. Second, the 5' and 3' noncoding sequences of the original aene have been removed. Although not strictly conforming to the algorithm described in FIG. 1, a few of the codon changes and especially the removal of the long 3' noncoding region is consistent with this algorithm.

The original PLRV sequence contains two potential plant polyadenylation signals (AACCAA and AAGCAT) and both of the these occur in the 3' noncoding sequence that has been removed in the synthetic gene. The original PLRV gene also contains on ATTTA sequence. This is also contained in the 3' noncoding sequence, and is in the midst of the longest stretch of uninterrupted A+T in the gene (a stretch of 7 A+T nucleotides). This sequence was removed in the synthetic gene. Thus, sequences that the algorithm of FIG. 1 targets for change have been changed in the synthetic PLRV coat protein gene by removal of the 3' noncoding segment. Within the coding sequence, codon changes were also made to remove three other regions of sequence described above. In particular, two regions of 5 consecutive A+T and one region of 5 consecutive G+C within the coding sequence have been removed in the synthetic gene.

The synthetic PLRV coat protein gene is cloned in a plant transformation vector such as pMON893 and used to transform potato plants as described above. These plants express the PLRV coat protein at higher levels than achieved with the naturally occurring gene, and these plants exhibit increased resistance to infection by PLRV.

EXAMPLE 10

Expression of Synthetic B.t. Genes with RUBISCO Small Subunit Promoters and Chloroplast Transit Peptides The genes in plants encoding the small subunit of RUBISCO (SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of B.t.k. genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of B.t.k. to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express B.t.k. in only a subset of plant tissues, if for example B.t. expression in certain cells was found to be deleterious to those cells. For example, for control of Colorado potato beetle in potato, it may be advantageous to use SSU promoters to direct B.t.t. expression to the leaves but not to the edible tubers.

Utilizing SSU CTP sequences to localize B.t. proteins to the chloroplast might also be advantageous. Localization of the B.t. to the chloroplast could protect the crotein from proteases found in the cytoplasm. This could stabilize the B.t. protein and lead to higher levels of accumulation of active orotein. B.t. genes containing the CTP could be used in combination with the SSU promoter or with other promoters such as CaMV35S.

A variety of plant transformation vectors were constructed for the expression of B.t.k. genes utilizing SSU promoters and SSU CTPs. The promoters and CTPs utilized were from the petunia SSU11a gene described by Tumer et al. (1986) and from the Arabidopsis ats1A gene (an SSU gene) described by Krebbers et al. (1988) and by Elionor et al. (1989). The petunia SSU11a promoter was contained on a DNA fragment that extended approximately 800 bp upstream of the SSU coding sequence. The Arabidopsis ats1A promoter was contained on a DNA fragment that extended approximately 1.8 kb upstream of the SSU coding sequence. At the upstream end convenient sites from the multilinker of pUC18 were used to move these promoters into plant transformation vectors such as pMON893. These promoter fragments extended to the start of the SSU coding sequence at which point an NcoI restriction site was engineered to allow insertion of the B.t. coding sequence, replacing the SSU coding sequence.

When SSU promoters were used in combination with their CTP, the DNA fragments extended through the coding sequence of the CTP and a small oortion of the mature SSU coding sequence at which point an NcoI restriction site was engineered by standard techniques to allow the in frame fusion of B.t. coding sequences with the CTP. In particular, for the cetunia SSU11a CTP, B.t. coding sequences were used to the SSU sequence after amino acid 8 of the mature SSU sequence at which point the NcoI site was placed. The 8 amino acids of mature SSU sequence were included because preliminary in vitro chloroplast uptake experiments indicated that uptake was of B.t.k. was observed only if this segment of mature SSU was ncluded. For the Arabidopsis ats1A CTP, the complete CTP was included plus 24 amino acids of mature SSU sequence plus the sequence gly-gly-arg-val-asn-cys-met-gln-ala-met, Sequence ID NO. 19 terminating in an NcoI site for *B.t.* fusion. This short sequence reiterates the native SSU CTP cleavage site (between the cys and met) plus a short segment surrounding the cleavage site. This sequence was included in order to insure proper uptake into chloroplasts. *B.t.* coding sequences were fused to this ats1A CTP after the met codon. In vitro uptake experiments with this CTP construction and other (non-*B.t.*) coding sequences showed that this CTP did target proteins to the chloroplast.

When CTPs were used in combination with the CaMV 35S promoter, the same CTP segments were used. They were excised just upstream of the ATG start sites of the CTP by engineering of BglII sites, and placed downstream of the CaMV35S promoter in pMON893, as BglII to NcoI fragments. *B.t.* coding sequences were fused as described above.

The wild type *B.t.k.* HD-1 coding sequence of pMON9921 (see FIG. 1) was fused to the ats1A promoter to make pMON1925 or the ats1A promoter plus CTP to make pMON1921. These vectors were used to transform tobacco plants, and the plants were screened for activity against tobacco hornworm. No toxic plants were recovered. This is surprising in light of the fact that toxic plants could be recovered, albeit at a low frequency, after transformation with pMON9921 in which the *B.t.k.* coding sequence was expressed from the enhanced CaMV35S, promoter in pMON893, and in light of the fact that Elionor et al. (1989) report that the ats1A promoter itself is comparable in strength to the CaMV35S promoter and approximately 10-fold stronger when the CTP sequence is included. At least for the wild-type *B.t.k.* HD-1 coding sequence, this does not appear to be the case.

A variety of plant transformation vectors were constructed utilizing either the truncated synthetic. HD-73 coding sequence of FIG. 4 or the full length *B.t.k.* HD-73 coding sequence of FIG. 11. These are listed in the table below.

TABLE XV

Gene Constructs with CTPs

| Vector | Promoter | CTP | B.t.k. HD-73 Coding Sequence |
|--------|----------|-----|------------------------------|
| pMON10806 | En 35S | ats1A | truncated |
| pMON10814 | En 35S | SSU11a | full length |
| pMON10811 | SSU11a | SSU11a | truncated |
| pMON10819 | SSU11a | none | truncated |
| PMON10815 | ats1A | none | truncated |
| pMON10817 | ats1A | ats1A | truncated |
| pMON10821 | En 35S | ats1A | truncated |
| pMON10822 | En 35S | ats1A | full length |
| pMON10838 | SSU11a | SSU11a | full length |
| pMON10839 | ats1A | ats1A | full length |

All of the above vectors were used to transform tobacco plants. For all of the vectors containing truncated *B.t.k.* genes, leaf tissue from these plants has been analyzed for toxic-zt to nsects and *B.t.k.* protein levels by immunoassay. pMON10806, 10811, 10819 and 10821 produce levels of *B.t.k.* protein comparable to pMON5383 and pMON5390 which contain synthetic *B.t.k.* HD-73 coding sequences driven by the En 35S promoter itself with no CTP. These plants also have the insecticidal activity expected for the *B.t.k.* protein levels detected. For pMON10815 and pMON10817 (containing the ats1A promoter) the level of *B.t.k.* protein is about 5-fold higher than that found in plants containing pMON5383 or 5390. These plants also have higher insecticidal activity. Plants containing 10815 and 10817 contain up to 1% of their total soluble leaf protein as *B.t.k.* HD-73. This is the highest level of *B.t.k.* protein yet obtained with any of the synthetic genes.

This result is surprising in two respects. First, as noted above, the wild type coding sequences fused to the ats1A promoter and CTP did not show any evidence of higher levels of expression than for En 35S, and in fact had lower expression based on the absence of any insecticidal plants. Second, Elionor et al. (1989) show that for two other genes, the ats1A CTP can increase expression from the ats1A promoter by about 10-fold. For the synthetic *B.t.k.* HD-73 gene, there is no consistent increase seen by including the CTP over and above that seen for the ats1A promoter alone.

Tobacco plants containing the full length synthetic HD-73 fused to the SSU11A CTP and driven by the En 35S promoter produced levels of *B.t.k.* protein and insecticidal activity comparable to pMON1518 which does not include the CTP. In addition, for pMON10518 the *B.t.k.* protein extracted from plants was observed by gel electrophoresis to contain multiple forms less than full length, apparently due to the cleavage of the C-terminal portion (not required for toxicity) in the cytoplasm. For pMON10814, the majority of the protein appeared to be intact full length indicating that the protein has been stabilized from proteolysis by targeting to the chloroplast.

EXAMPLE 11

Taroetina of *B.t.* Proteins to the Extracellular Space or Vacuole through the Use of Signal Peotides The *B.t.* proteins produced from the synthetic genes described here are localized to the cytoplasm of the plant cell, and this cytoplasmic localization results in plants that are insecticidally effective. It may be advantageous for some purposes to direct the *B.t.* proteins to other compartments of the plant cell. Localizing *B.t.* proteins in compartments other than the cytoplasm may result in less exposure of the *B.t.* proteins to cytoplasmic proteases leading to greater accumulation of the protein yielding enhanced insecticidal activity. Extracellular localization could lead to more efficient exposure of certain insects to the *B.t.* proteins leading to greater efficacy. If a *B.t.* protein were found to be deleterious to plant cell function, then localization to a noncytoplasmic compartment could protect these cells from the protein.

In plants as well as other eucaryotes, proteins that are destined to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion ifnto the endoplasmic reticulum with cleavage of the signal peptide occuring at this stage. The mature protein then passes thru the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasam of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct B.t. proteins out of the cytoplasm is to fuse the genes for synthetic B.t. genes to DNA sequences encoding known plant signal peptides. These fusion genes will give rise to B.t. proteins that enter the secretory pathway, and lead to extracellualar secretion or targeting to the vacuole or other compartments.

Signal sequences for several plant genes have been described. One such sequence is for the tobacco pathogenesis related protein PR1b described by Cornelissen et al. The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the beta subunit of the 7S storage protein of common bean (*Phaseolus vulgaris*), PvuB has been described by Doyle et al. Based on the published these published sequences, genes were synthesized by chemical synthesis of oligonucleotides that encoded the signal peptides for PR1b and PvuB. The synthetic genes for these signal peptides corresponded exactly to the reported DNA sequences. Just upstream of the translational intiation codon of each signal peptide a BamHI and BglI: site were inserted with the BamHI site at the 5 ' end. This allowed the insertion of the signal peptide encoding segments into the BglII site of pMON893 for expression from the En 35S promoter. In some cases to achieve secretion or compartmentalization of heterologous proteins, it has proved necessary to include some amino acid sequence beyond the normal cleavage site of the signal peptide. This may be necessary to insure proper cleavage of the signal peptide. For PR1b the synthetic DNA sequence also included the first 10 amino acids of mature PR1b. For PvuB the synthetic DNA sequence included the first 13 amino acids of mature PvuB. Both synthetic signal peptide encoding segments ended with NcoI sites to allow fusion in frame to the methionine initiation codon of the synthetic B.t. genes.

Four vectors encoding synthetic B.t.k. HD-73 genes were constructed containing these signal peptides. The synthetic truncated HD-73 gene from pMON5383 was fused with the signal peptide sequence of PvuB and incorporated into pMON893 to create pMON10827. The The synthetic truncated HD-73 gene from pMON5383 was also fused with the signal peptide sequence of PR1b to create pMON10824. The full length synthetic HD-73 gene from pMON10518 was fused with the signal peptide sequence of PvuB and incorporated into pMON893 to create pMON10828. The full length synthetic HD-73 gene from pMON10518 was also fused with the signal peptide sequence of PR1b and incorporated into pMON893 to create pMON10825.

These vectors were used to transform tobacco plants and the plants were assayed for expression of the B.t.k. protein by Western blot analysis and for insecticidal efficacy. pMON10824 and pMON10827 produced amounts of B.t.k. protein in leaf comparable to the truncated HD-73 vectors, pMON5383 and pMON5390. pMON10825 and pMON10828 produced full length B.t.k. protein in amounts comparable to pMON10518. In all cases, the plants were insecticidally active against tobacco hornworm.

BIBLIOGRAPHY

Adami, G. and Nevins, J. (1988) RNA Processing, Cold Spring Harbor Laboratory, p. 26.
Adang, et al., *Molecular Strateaies for Crop Protection* (1987) pp. 345–353, Alan R. Liss, Inc.
Barton, K. A. et al., *Plant Physiol*, (1987), 85,1103–1109.
Bevan, M. et al., *Nature* (1983) 304:184.
Brady, H. and Wold, W. (1988), RNA Processing, Cold Spring Harbor Laboratory, p. 224.
Brown, John W., *Nucleic Acids Research* (1986) Vol. 14, No. 24, p. 9549.
Callis, J. Fromm, M. and Walbot, V., *Genes and Develop.* (1987), 1:1183–1200.
Conway, L. and Wickens, M. (1988), RNA Processing, Cold Spring Harbor Laboratory, p. 40.
Cornellssen, B. J. C., et al., *EMBO J*. (1986) Vol. 5, No. 1, 37–40.
Daar, I. O. et al. (1988), RNA Processing, Cold Spring Harbor Laboratory, p. 45.
Dean, C. et al., *Nucleic Acids Research* (1986), Vol. 14, No. 5, p. 2229.
Dedrick, R., et al., *The Journal of Biological Chemistry* (1987), Vol. 262, No. 19, pp. 9098–1106.
Donovan, W. P. et al., *The J. of Biol. Chem.* (1988), Vol. 263, No. 1, pp. 561–567.
Doyle, J. J., et al., *J. Biol. Chem.* (1986), Vol. 261, No. 20, 9228–9236.
Elionor, R. P., et al., *Mol. Gen. Gener.* (1989), 218:78–86.
Fischhoff, D. A. et al., *Bio/Technology* (1987), Vol. 5, p. 807.
Fraley, R. T. et al., *Bio/Technology* (1985) 3:629–635.
Fromm, M., Taylor, L. P. and Walbot, V., *Nature* (1986), 319:791–793.
Gallego, M. E. and Nadal-Ginard B. (1988), RNA Processing, Cold Spring Harbor Laboratory, p. 61.
Genovese, C. and Milcarek, C. (1988), RNA Processing, Cold Spring Harbor Laboratory, p. 62.
Gil, A. and Proudfoot, N. J., *Nature* (1984), Vol. 312, p. 473.
Goodall, G. et al. (1988), RNA Processing, Cold Spring Harbor Laboratory, p. 63.
Gross, et al. (1988), RNA Processing, Cold Spring Harbor Laboratory, p. 128.
Hampson, R. K. and Rottman, F. M. (1988), RNA Processing, Cold Spring Harbor Laboratory, p. 68.
Hanley, Brian A and Schuler, Mary A., *Nucleic Acids Research* (1988), Vol. 16, No. 14, p. 7159.
Helfman, D. M. and Ricci, W. M. (1988), RNA Processing, Cold Spring Harbor Laboratory, p. 219.
Herrera-Estrella, L. et al., *Nature* (1983), 303:209.
Hoekema, A. et al., *Molecular and Cellular Biology* (1987), Vol. 7, pp. 2914–2924.
Honee, G. et al., *Nucleic Acids Research* (1988), Vol. 16, No. 13.
Horsch, R. B. et al., *Science* (1985), 227:1229.
Jarret, R. L. et al., *Physiol. Plant* (1980), 49:177.
Jarret, R. L. et al., *In Vitro* (1981), 17:825.
Kay, R. et al., *Science* (1987), 236:1299–1302.
Kessler, M. et al. (1988), RNA Processing, Cold Spring Harbor Laboratory, p. 85.
Klee, H. J. et al., *Bio/Technolocv* (1985), 3:637–642.
Kozak, M., *Nature* (1984), 308:241–246.
Krebbers, E., et al., *Plant Molecular Biology* (1988), 11:745–759.

Kunkel, T. A., *Proc. Natl. Acad. Sci. USA* (1985), Vol. 82, pp. 488–492.
Marrone et al., *J. Econ. Entomol.* (1985), 78–290–293.
Marzluff, W. and Pandey, N. (1988), RNA Processing, Cold Spring Harbor Laboratory, p. 244.
McCormick, S. et al., *Plant Cell Reports* (1986), 5:81–84.
McDevitt, M. A. et al., *Cell* (1984), Vol. 37, pp. 993–999.
Murashige, T. and Skoog, F., *Physiol. Plant* (1962), 15:473.
Odell, J. et al., *Nature* (1985), 313:810.
Pandey, N. B. and Marzluff, W. F. (1987), RNA Processing, Cold Spring Harbor Laboratory, p. 133.
Proudfoot, N. J. et al. (1987), ANA Processing, Cold Spring Harbor Laboratory, p. 17.
Reines, D., et al., *J. Mol. Biol.* (1987) 196:299–312.
Sadofsky, M. and Alwine, J. C., *Molecular and Cellular Biology* (1984), Vol. 4, No. 8, pp. 1460–468.
Sanders, P. R. et al., *Nucleic Acids Research* (1987), Vol. 15, No. 4, p. 1543.
Schuler, M. A. et al., *Nucleic Acids Research* (1982), Vol. 10, No. 24, pp. 8225–8244.
Shaw, G. & Kamen, R., *Cell* (1986), 46:659–667.
Shaw, G. and Kamen, R. (1987), RNA Processing, Cold Spring Harbor Laboratory, p. 220.
Trolinder, N. L. and Goodin, J. R., *Plant Cell Reports* (1987), 6:231–234.
Tsurushita, N. and Korn, L. J. (1987), RNA Processing, Cold Spring Harbor Laboratory, p. 215.
Tumer, N. E., et al., *Nucleic Acids Reg.* (1986), Vol. 14:8, 3325.
Vaeck, M. et al., Nature (1987), Vol. 328, p. 33.
Velten et al., *EMBO J.* (1984), 3:2723–2730.
Velten & Schell, *Nucleic Acids Research* (1985), 13:6981–6998.
Visser, B. et al., *Mol. Gen. Genet.* (1988), 212:219–224.
Webb, K. J. et al., *Plant Sci. Letters* (1983), 30:1.
Wickens, M. and Stephenson, P., *Science* (1984), Vol. 226, p. 1045.
Wickens, M. et al. (1987), RNA Processing, Cold Spring Harbor Laboratory, p. 9.
Wiebauer, K. et al., *Molecular and Cellular Biology* (1988), Vol. 8, No. 5, pp. 2042–2051.
Yamamoto, T. and Iizuka, T., *Archives Of Biochemistry and Biophysics* (1983), Vol. 227, No. 1, pp. 233–241.

---

SEQUENCE LISTING

< 1 6 0 > 27

< 2 1 0 > 1
< 2 1 1 > 18
< 2 1 2 > DNA
< 2 1 3 > Artificial Sequence

< 2 2 0 >
< 2 2 3 > Description of Artificial Sequence: mutagenesis primer

< 4 0 0 > 1 tccccagata atatcaac                                                                                     18

< 2 1 0 > 2
< 2 1 1 > 48
< 2 1 2 > DNA
< 2 1 3 > Artificial Sequence

< 2 2 0 >
< 2 2 3 > Description of Artificial Sequence: mutagenesis primer

< 4 0 0 > 2 ggcttgattc ctagcgaact cttcgattct ctggttgatg agctgttc                                                    48

< 2 1 0 > 3
< 2 1 1 > 54
< 2 1 2 > DNA
< 2 1 3 > Artificial Sequence

< 2 2 0 >
< 2 2 3 > Description of Artificial Sequence: mutagenesis primer

< 4 0 0 > 3 caaaactgag aggtggaggt tggcagcttg aacgtacacg gagaggagag gaac                                              54

< 2 1 0 > 4
< 2 1 1 > 48
< 2 1 2 > DNA
< 2 1 3 > Artificial Sequence

< 2 2 0 >
< 2 2 3 > Description of Artificial Sequence: mutagenesis primer

< 4 0 0 > 4 agttagtgta agctctcttc tgaactggtt gtacctgatc caatctct    48

<210> 5
<211> 39
<212> DNA
<213> Artificial Sequence

<220>
<223> Description of Artificial Sequence: mutagenesis primer

<400> 5
agccatgatc tggtgaccgg accagtagta ttctcctct    39

<210> 6
<211> 32
<212> DNA
<213> Artificial Sequence

<220>
<223> Description of Artificial Sequence: mutagenesis primer

<400> 6
agttgttggt tgttgatccc gatgttaaaa gg    32

<210> 7
<211> 37
<212> DNA
<213> Artificial Sequence

<220>
<223> Description of Artificial Sequence: mutagenesis primer

<400> 7
gtgatgaagg gatgatgttg ttgaactcag cactacg    37

<210> 8
<211> 100
<212> DNA
<213> Artificial Sequence

<220>
<223> Description of Artificial Sequence: mutagenesis primer

<400> 8
cagaagttcc agagccaaga ttagtagact tggtgagtgg gatttgggtg atttgtgatg    60
aagggatgat gttgttgaac tcagcactac gatgtatcca    100

<210> 9
<211> 27
<212> DNA
<213> Artificial Sequence

<220>
<223> Description of Artificial Sequence: mutagenesis primer

<400> 9
tgatgtgtgg aactgaaggt ttgtggt    27

<210> 10
<211> 50
<212> DNA
<213> Artificial Sequence

<220>
<223> Description of Artificial Sequence: mutagenesis primer

<400> 10
aatactatcg gatgcgatga tgttgttgaa ctcagcacta cggtgtatcc    50

<210> 11
<211> 33
<212> DNA
<213> Artificial Sequence

<220>
<223> Description of Artificial Sequence: mutagenesis primer

<400> 11
tcctgaaatg acagaaccgt tgaagagaaa gtt    33

<210> 12
<211> 48
<212> DNA
<213> Artificial Sequence

<220>
<223> Description of Artificial Sequence: mutagenesis primer

<400> 12
atttccactg ctgttgagtc taacgaggtc tccaccagtg aatcctgg    48

<210> 13
<211> 60
<212> DNA
<213> Artificial Sequence

<220>
<223> Description of Artificial Sequence: mutagenesis primer

<400> 13
gtgaataggg gtcacagaag catacctcac acgaactcta tatctggtag atgttggatg    60

<210> 14
<211> 33
<212> DNA
<213> Artificial Sequence

<220>
<223> Description of Artificial Sequence: mutagenesis primer

<400> 14
tgtagctgga actgtattgg agaagatgga tga    33

<210> 15
<211> 48
<212> DNA
<213> Artificial Sequence

<220>
<223> Description of Artificial Sequence: mutagenesis primer

<400> 15
ttcaaagtaa ccgaaatcgc tggattggag attatccaag gaggtagc    48

<210> 16
<211> 39
<212> DNA
<213> Artificial Sequence

<220>
<223> Description of Artificial Sequence: mutagenesis primer

<400> 16
actaaagttt ctaacaccca cgatgttacc gagtgaaga    39

<210> 17
<211> 36
<212> DNA
<213> Artificial Sequence

<220>
<223> Description of Artificial Sequence: mutagenesis primer

<400> 17
aactggaatg aactcgaatc tgtcgataat cactcc    36

<210> 18
<211> 54
<212> DNA
<213> Artificial Sequence

<220>
<223> Description of Artificial Sequence: mutagenesis primer

<400> 18
ggacactaga tcttagtgat aatcggtcac atttgtcttg agtccaagct ggtt    54

<210> 19
<211> 10
<212> PRT
<213> Artificial Sequence

<220>
<223> Description of Artificial Sequence: peptide
      sequence reiterates the native small subunit
      promoter chloroplast transit peptide cleavage site

<400> 19

Gly Gly Arg Val Asn Cys Met Gln Ala Met
 1               5                  10

<210> 20
<211> 1743
<212> DNA
<213> Artificial Sequence

<220>
<223> Description of Artificial Sequence: synthetic
      structural gene encoding B.t.k. HD-1 insectidal
      protein

<400> 20
atggctatag aaactggtta caccccaatc gatatttcct tgtcgctaac gcaatttctt 60
ttgagtgaat ttgttcccgg tgctggattt gtgttaggac tagttgatat tatctgggga 120
atttttggtc cctctcaatg ggacgcattt cttgtacaaa ttgaacagct catcaaccag 180
agaatcgaag agttcgctag gaatcaagcc atttctagat tagaaggact aagcaatctt 240
tatcaaattt acgcagaatc ttttagagag tgggaagcag atcctactaa tccagcatta 300
agagaagaga tgcgtattca attcaatgac atgaacagtg cccttacaac cgctattcct 360
ctttttgcag ttcaaaatta tcaagttcct ctcctctccg tgtacgttca agctgccaac 420
ctccacctct cagttttgag agatgtttca gtgtttggac aaaggtgggg atttgatgcc 480
gcgactatca atagtcgtta taatgattta actaggctta ttggcaacta tacagatcat 540
gctgtacgct ggtacaatac gggattagag cgtgtatggg gaccggattc tagagattgg 600
atcaggtaca accagttcag aagagagctt acactaactg tattagatat cgtttctcta 660
tttccgaact atgatagtag aacgtatcca attcgaacag tttcccaatt aacaagagaa 720

-continued

```
atttatacaa  acccagtatt  agaaaatttt  gatggtagtt  ttcgaggctc  ggctcagggc   780
atagaaggaa  gtattaggag  tccacatttg  atggatatac  ttaatagtat  aaccatctat   840
acggatgctc  atagaggaga  atactactgg  tccggtcacc  agatcatggc  ttctcctgta   900
gggttttcgg  ggccagaatt  cactttccg   ctatatggaa  ctatgggaaa  tgcagctcca   960
caacaacgta  ttgttgctca  actaggtcag  ggcgtgtata  gaacattatc  gtccaccttta 1020
tatagaagac  cttttaacat  cgggatcaac  aaccaacaac  tatctgttct  tgacgggaca  1080
gaatttgctt  atggaacctc  ctcaaatttg  ccatccgctg  tatacagaaa  aagcggaacg  1140
gtagattcgc  tggatgaaat  accgccacag  aataacaacg  tgccacctag  gcaaggattt  1200
agtcatcgat  taagccatgt  ttcaatgttt  cgttcaggct  ttagtaatag  tagtgtaagt  1260
ataataagag  ctcctatgtt  ctcttggata  catcgtagtg  ctgagttcaa  caacatcatc  1320
ccttcatcac  aaatcaccca  aatcccactc  accaagtcta  ctaatcttgg  ctctggaact  1380
tctgtcgtta  aaggaccagg  atttacagga  ggagatattc  ttcgaagaac  ttcacctggc  1440
cagatttcaa  ccttaagagt  aaatattact  gcaccattat  cacaaagata  tcgggtaaga  1500
attcgctacg  cttctaccac  aaaccttcag  ttccacacat  caattgacgg  aagacctatt  1560
aatcaggga   attttcagc   aactatgagt  agtgggagta  atttacagtc  cggaagcttt  1620
aggactgtag  gttttactac  tccgtttaac  ttttcaaatg  gatcaagtgt  atttacgtta  1680
agtgctcatg  tcttcaattc  aggcaatgaa  gtttatatag  atcgaattga  atttgttccg  1740
gca                                                                    1743
```

< 2 1 0 > 21
< 2 1 1 > 1767
< 2 1 2 > DNA
< 2 1 3 > Artificial Sequence

< 2 2 0 >
< 2 2 3 > Description of Artificial Sequence: synthetic
structural gene encoding insecticidal protein of
B.t.k.

-continued

```
caacaacgta tcgttgctca actaggtcag ggtgtctaca gaaccttgtc ttccaccttg      1020
tacagaagac ccttcaatat cggtatcaac aaccagcaac tttccgttct tgacggaaca      1080
gagttcgcct atggaacctc ttctaacttg ccatccgctg tttacagaaa gagcggaacc      1140
gttgattcct tggacgaaat cccaccacag aacaacaatg tgccacccag gcaaggattc      1200
tcccacaggt tgagccacgt gtccatgttc cgttccggat tcagcaacag ttccgtgagc      1260
atcatcagag ctcctatgtt ctcttggata caccgtagtg ctgagttcaa caacatcatc      1320
gcatccgata gtattactca aatccctgca gtgaagggaa actttctctt caacggttct      1380
gtcatttcag gaccaggatt cactggtgga gacctcgtta gactcaacag cagtggaaat      1440
aacattcaga atagagggta tattgaagtt ccaattcact tcccatccac atctaccaga      1500
tatagagttc gtgtgaggta tgcttctgtg accctattc acctcaacgt taattggggt       1560
aattcatcca tcttctccaa tacagttcca gctacagcta cctccttgga taatctccaa      1620
tccagcgatt tcggttactt tgaaagtgcc aatgctttta catcttcact cggtaacatc      1680
gtgggtgtta gaaactttag tgggactgca ggagtgatta tcgacagatt cgagttcatt      1740
ccagttactg caacactcga ggctgag                                          1767
```

< 2 1 0 > 22
< 2 1 1 > 1845
< 2 1 2 > DNA
< 2 1 3 > Artificial Sequence

< 2 2 0 >
< 2 2 3 > Description of Artificial Sequence: synthetic
        structural gene encoding insecticidal protein of
        B.t.k. HD-1

< 4 0 0 > 22

```
atggacaaca acccaaacat caacgaatgc attccataca actgcttgag taacccagaa      60
gttgaagtac ttggtggaga acgcattgaa accggttaca ctcccatcga catctccttg      120
tccttgacac agtttctgct cagcgagttc gtgccaggtg ctgggttcgt tctcggacta      180
gttgacatca tctggggtat ctttggtcca tctcaatggg atgcattcct ggtgcaaatt      240
gagcagttga tcaaccagag gatcgaagag ttcgccagga accaggccat ctctaggttg      300
gaaggattga gcaatctcta ccaaatctat gcagagagct tcagagagtg ggaagccgat      360
cctactaacc cagctctccg cgaggaaatg cgtattcaat caacgacat gaacagcgcc       420
ttgaccacag ctatccatt gttcgcagtc cagaactacc aagttcctct cttgtccgtg      480
tacgttcaag cagctaatct tcacctcagc gtgcttcgag acgttagcgt gtttgggcaa      540
aggtggggat tcgatgctgc aaccatcaat agccgttaca acgaccttac taggctgatt      600
ggaaactaca ccgaccacgc tgttcgttgg tacaacactg gcttggagcg tgtctggggt      660
cctgattcta gagattggat tagatacaac cagttcagga gagaattgac cctcacagtt      720
ttggacattg tgtctctctt cccgaactat gactccagaa cctaccctat ccgtacagtg      780
tcccaactta ccagagaaat ctatactaac ccagttcttg agaacttcga cggtagcttc      840
cgtggttctg cccaaggtat cgaaggctcc atcaggagcc cacacttgat ggacatcttg      900
aacagcataa ctatctacac cgatgctcac agaggagagt attactggtc tggacaccag      960
atcatggcct ctccagttgg attcagcggg cccgagttta cctttcctct ctatggaact      1020
atgggaaacg ccgctccaca acaacgtatc gttgctcaac taggtcaggg tgtctacaga      1080
accttgtctt ccaccttgta cagaagaccc ttcaatatcg gtatcaacaa ccagcaactt      1140
```

-continued

```
tccgttcttg acggaacaga gttcgcctat ggaacctctt ctaacttgcc atccgctgtt    1200
tacagaaaga gcggaaccgt tgattccttg gacgaaatcc caccacagaa caacaatgtg    1260
ccacccaggc aaggattctc ccacaggttg agccacgtgt ccatgttccg ttccggattc    1320
agcaacagtt ccgtgagcat catcagagct cctatgttct catggattca tcgtagtgct    1380
gagttcaaca atatcattcc ttcctctcaa atcacccaaa tccattgac caagtctact     1440 aaccttggat ctggaacttc tgtcgtgaaa ggaccaggct tcacaggagg tgatattctt    1500
agaagaactt ctcctggcca gattagcacc ctcagagtta acatcactgc accactttct    1560
caaagatatc gtgtcaggat tcgttacgca tctaccacta acttgcaatt ccacacctcc    1620
atcgacggaa ggcctatcaa tcagggtaac ttctccgcaa ccatgtcaag cggcagcaac    1680
ttgcaatccg gcagcttcag aaccgtcggt ttcactactc ctttcaactt ctctaacgga    1740
tcaagcgttt tcacccttag cgctcatgtg ttcaattctg gcaatgaagt gtacattgac    1800
cgtattgagt ttgtgcctgc cgaagttacc ttcgaggctg agtac                     1845
```

<210> 23
<211> 1921
<212> DNA
<213> Artificial Sequence

<220>
<223> Description of Artificial Sequence:synthetic structural gene encoding insecticidal protein derived from B.t.k. HD-73

<400> 23

```
atggacaaca acccaaacat caacgaatgc attccataca actgcttgag taacccagaa    60
gttgaagtac ttggtggaga acgcattgaa accggttaca ctccatcga catctccttg     120 tccttgacac agtttctgct cagcgagttc gtgccaggtg ctgggttcgt tctcggacta    180
gttgacatca tctggggtat ctttggtcca tctcaatggg atgcattcct ggtgcaaatt    240
gagcagttga tcaaccagag gatcgaagag ttcgccagga ccaggccat ctctaggttg     300 gaaggattga gcaatctcta ccaaatctat gcagagagct tcagagagtg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
aggtggggat tcgatgctgc aaccatcaat agccgttaca acgaccttac taggctgatt    600
ggaaactaca ccgaccacgc tgttcgttgg tacaacactg gcttggagcg tgtctggggt    660
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc cacacttgat ggacatcttg    900
aacagcataa ctatctacac cgatgctcac agaggagagt attactggtc tggacaccag    960
atcatggcct ctccagttgg attcagcggg cccgagttta cctttcctct ctatggaact    1020
atgggaaacg ccgctccaca acaacgtatc gttgctcaac taggtcaggg tgtctacaga    1080
accttgtctt ccaccttgta cagaagaccc ttcaatatcg gtatcaacaa ccagcaactt    1140
tccgttcttg acggaacaga gttcgcctat ggaacctctt ctaacttgcc atccgctgtt    1200
tacagaaaga gcggaaccgt tgattccttg gacgaaatcc caccacagaa caacaatgtg    1260
ccacccaggc aaggattctc ccacaggttg agccacgtgt ccatgttccg ttccggattc    1320
```

| agcaacagtt | ccgtgagcat | catcagagct | cctatgttct | cttggataca | ccgtagtgct | 1380 |
| gagttcaaca | acatcatcgc | atccgatagt | attactcaaa | tccctgcagt | gaagggaaac | 1440 |
| tttctcttca | acggttctgt | catttcagga | ccaggattca | ctggtggaga | cctcgttaga | 1500 |
| ctcaacagca | gtggaaataa | cattcagaat | agagggtata | ttgaagttcc | aattcacttc | 1560 |
| ccatccacat | ctaccagata | tagagttcgt | gtgaggtatg | cttctgtgac | ccctattcac | 1620 |
| ctcaacgtta | attggggtaa | ttcatccatc | ttctccaata | cagttccagc | tacagctacc | 1680 |
| tccttggata | atctccaatc | cagcgatttc | ggttactttg | aaagtgccaa | tgcttttaca | 1740 |
| tcttcactcg | gtaacatcgt | gggtgttaga | aactttagtg | ggactgcagg | agtgattatc | 1800 |
| gacagattcg | agttcattcc | agttactgca | acactcgagg | ctgaatataa | tctggaaaga | 1860 |
| gcgcagaagg | cggtaatgcg | ctgtttacgt | ctacaaacca | gcttggactc | aagacaaatg | 1920 |
| g | | | | | | 1921 |

<210> 24
<211> 3534
<212> DNA
<213> Artificial Sequence

<220>
<223> Description of Artificial Sequence:synthetic
       structural gene encoding insecticidal protein
       derived from B.t.k. HD-73

<400> 24

| atggacaaca | acccaaacat | caacgaatgc | attccataca | actgcttgag | taacccagaa | 60 |
| gttgaagtac | ttggtggaga | acgcattgaa | accggttaca | ctcccatcga | catctccttg | 120 |
| tccttgacac | agtttctgct | cagcgagttc | gtgccaggtg | ctgggttcgt | tctcggacta | 180 |
| gttgacatca | tctggggtat | ctttggtcca | tctcaatggg | atgcattcct | ggtgcaaatt | 240 |
| gagcagttga | tcaaccagag | gatcgaagag | ttcgccagga | accaggccat | ctctaggttg | 300 |
| gaaggattga | gcaatctcta | ccaaatctat | gcagagagct | tcagagagtg | ggaagccgat | 360 |
| cctactaacc | cagctctccg | cgaggaaatg | cgtattcaat | tcaacgacat | gaacagcgcc | 420 |
| ttgaccacag | ctatcccatt | gttcgcagtc | cagaactacc | aagttcctct | cttgtccgtg | 480 |
| tacgttcaag | cagctaatct | tcacctcagc | gtgcttcgag | acgttagcgt | gtttgggcaa | 540 |
| aggtggggat | tcgatgctgc | aaccatcaat | agccgttaca | acgaccttac | taggctgatt | 600 |
| ggaaactaca | ccgaccacgc | tgttcgttgg | tacaacactg | gcttggagcg | tgtctggggt | 660 |
| cctgattcta | gagattggat | tagatacaac | cagttcagga | gagaattgac | cctcacagtt | 720 |
| ttggacattg | tgtctctctt | cccgaactat | gactccagaa | cctaccctat | ccgtacagtg | 780 |
| tcccaactta | ccagagaaat | ctatactaac | ccagttcttg | agaacttcga | cggtagcttc | 840 |
| cgtggttctg | cccaaggtat | cgaaggctcc | atcaggagcc | cacacttgat | ggacatcttg | 900 |
| aacagcataa | ctatctacac | cgatgctcac | agaggagagt | attactggtc | tggacaccag | 960 |
| atcatggcct | ctccagttgg | attcagcggg | cccgagttta | cctttcctct | ctatggaact | 1020 |
| atgggaaacg | ccgctccaca | acaacgtatc | gttgctcaac | taggtcaggg | tgtctacaga | 1080 |
| accttgtctt | ccaccttgta | cagaagaccc | ttcaatatcg | gtatcaacaa | ccagcaactt | 1140 |
| tccgttcttg | acggaacaga | gttcgcctat | ggaacctctt | ctaacttgcc | atccgctgtt | 1200 |
| tacagaaaga | gcggaaccgt | tgattccttg | gacgaaatcc | caccacagaa | caacaatgtg | 1260 |
| ccacccaggc | aaggattctc | ccacaggttg | agccacgtgt | ccatgttccg | ttccggattc | 1320 |

| | | | | | | |
|---|---|---|---|---|---|---|
| agcaacagtt | ccgtgagcat | catcagagct | cctatgttct | cttggataca | ccgtagtgct | 1380 |
| gagttcaaca | acatcatcgc | atccgatagt | attactcaaa | tccctgcagt | gaagggaaac | 1440 |
| tttctcttca | acggttctgt | catttcagga | ccaggattca | ctggtggaga | cctcgttaga | 1500 |
| ctcaacagca | gtggaaataa | cattcagaat | agagggtata | ttgaagttcc | aattcacttc | 1560 |
| ccatccacat | ctaccagata | tagagttcgt | gtgaggtatg | cttctgtgac | ccctattcac | 1620 |
| ctcaacgtta | attggggtaa | ttcatccatc | ttctccaata | cagttccagc | tacagctacc | 1680 |
| tccttggata | atctccaatc | cagcgatttc | ggttactttg | aaagtgccaa | tgcttttaca | 1740 |
| tcttcactcg | gtaacatcgt | gggtgttaga | aactttagtg | ggactgcagg | agtgattatc | 1800 |
| gacagattcg | agttcattcc | agttactgca | acactcgagg | ctgaatataa | tctggaaaga | 1860 |
| gcgcagaagg | cggtgaatgc | gctgtttacg | tctacaaacc | agctcggcct | caagaccaat | 1920 |
| gtgacggatt | atcatattga | tcaagtgtcc | aacttggtga | cctacctcag | cgatgagttc | 1980 |
| tgtctggatg | aaaagcgaga | attgtccgag | aaagtcaaac | atgcgaagcg | actcagtgat | 2040 |
| gaacgcaatt | tactccaaga | ttcaaatttc | aaagacatta | taggcaacc | agaacgtggg | 2100 |
| tggggcggaa | gtacagggat | taccatccag | ggaggtgacg | acgtgttcaa | ggagaactac | 2160 |
| gtcacactat | caggtacctt | tgatgagtgc | tatccaacat | acctctacca | gaagatcgac | 2220 |
| gagtccaagt | tgaaagcctt | tacccgttat | caattaagag | ggtatatcga | agatagtcaa | 2280 |
| gacctcgaga | tctacctcat | ccgctacaat | gcaaaacatg | aaacagtaaa | tgtgccaggt | 2340 |
| acgggttcct | tatggccgct | ttcagcccaa | agtccaatcg | gaaagtgtgg | agagccgaat | 2400 |
| cgatgcgcgc | cacaccttga | atggaatcct | gacttagatt | gttcgtgtag | ggatggagaa | 2460 |
| aagtgtgccc | atcattcgca | tcatttctcc | ttagacattg | atgtaggatg | tacagactta | 2520 |
| aatgaggacc | taggtgtatg | ggtgatcttt | aagattaaga | cgcaagatgg | gcacgcaaga | 2580 |
| ctagggaatc | tagagtttct | cgaagagaaa | ccattagtag | gagaagcgct | agctcgtgtg | 2640 |
| aaaagagcgg | agaaaaatg | gagagacaaa | cgtgagaagt | tggaatggga | gaccaacatc | 2700 |
| gtctacaaag | aggcaaaaga | atctgtagat | gctttatttg | taaactctca | atatgatcaa | 2760 |
| ttacaagcgg | atacgaatat | tgccatgatt | catgcggcag | ataaacgtgt | tcatagcatt | 2820 |
| cgagaagctt | atctgcctga | gctgtctgtg | attccggtg | tcaatgcggc | tattttgaa | 2880 |
| gaattagaag | ggcgtatttt | cactgcattc | tccctctacg | atgccagaaa | cgtcatcaag | 2940 |
| aacggtgact | tcaacaatgg | cttatcctgc | tggaacgtga | aagggcatgt | agatgtagaa | 3000 |
| gaacaaaaca | accaacgttc | ggtccttgtt | gttccggaat | gggaagcaga | agtgtcacaa | 3060 |
| gaagttcgtg | tctgtccggg | tcgtggctat | atccttcgtg | tcacagcgta | caaggaggga | 3120 |
| tatggagaag | gttgcgtaac | cattcatgag | atcgagaaca | atacagacga | actgaagttt | 3180 |
| agcaactgcg | tagaagagga | aatctatcca | ataacacgg | taacgtgtaa | tgattatact | 3240 |
| gtaaatcaag | aagaatacgg | aggtgcgtac | acttctcgta | atcgaggata | taacgaagct | 3300 |
| ccttccgtac | cagctgatta | tgcgtcagtc | tatgaagaaa | aatcgtatac | agatggacga | 3360 |
| agagagaatc | cttgtgaatt | taacagaggg | tatagggatt | acacgccact | accagttggt | 3420 |
| tatgtgacaa | aagaattaga | atacttccca | gaaaccgata | aggtatggat | tgagattgga | 3480 |
| gaaacggaag | gaacatttat | cgtggacagc | gtggaattac | tccttatgga | ggaa | 3534 |

< 2 1 0 > 25
< 2 1 1 > 3534
< 2 1 2 > DNA
< 2 1 3 > Artificial Sequence

<220>
<223> Description of Artificial Sequence:synthetic structural gene encoding insecticidal protein derived from B.t.k. HD-73

<400> 25

```
atggacaaca acccaaacat caacgaatgc attccataca actgcttgag taacccagaa    60
gttgaagtac ttggtggaga acgcattgaa accggttaca ctcccatcga catctccttg   120
tccttgacac agtttctgct cagcgagttc gtgccaggtg ctgggttcgt tctcggacta   180
gttgacatca tctggggtat ctttggtcca tctcaatggg atgcattcct ggtgcaaatt   240
gagcagttga tcaaccagag gatcgaagag ttcgccagga accaggccat ctctaggttg   300
gaaggattga gcaatctcta ccaaatctat gcagagagct tcagagagtg ggaagccgat   360
cctactaacc cagctctccg cgaggaaatg cgtattcaat tcaacgacat gaacagcgcc   420
ttgaccacag ctatcccatt gttcgcagtc cagaactacc aagttcctct cttgtccgtg   480
tacgttcaag cagctaatct tcacctcagc gtgcttcgag acgttagcgt gtttgggcaa   540
aggtggggat tcgatgctgc aaccatcaat agccgttaca acgaccttac taggctgatt   600
ggaaactaca ccgaccacgc tgttcgttgg tacaacactg gcttggagcg tgtctggggt   660
cctgattcta gagattggat tagatacaac cagttcagga gagaattgac cctcacagtt   720
ttggacattg tgtctctctt cccgaactat gactccagaa cctaccctat ccgtacagtg   780
tcccaactta ccagagaaat ctatactaac ccagttcttg agaacttcga cggtagcttc   840
cgtggttctg cccaaggtat cgaaggctcc atcaggagcc cacacttgat ggacatcttg   900
aacagcataa ctatctacac cgatgctcac agaggagagt attactggtc tggacaccag   960
atcatggcct ctccagttgg attcagcggg cccgagttta cctttcctct ctatggaact  1020
atgggaaacg ccgctccaca acaacgtatc gttgctcaac taggtcaggg tgtctacaga  1080
accttgtctt ccaccttgta cagaagaccc ttcaatatcg gtatcaacaa ccagcaactt  1140
tccgttcttg acggaacaga gttcgcctat ggaacctctt ctaacttgcc atccgctgtt  1200
tacagaaaga gcggaaccgt tgattccttg gacgaaatcc caccacagaa caacaatgtg  1260
ccacccaggc aaggattctc ccacaggttg agccacgtgt ccatgttccg ttccggattc  1320
agcaacagtt ccgtgagcat catcagagct cctatgttct cttggataca ccgtagtgct  1380
gagttcaaca acatcatcgc atccgatagt attactcaaa tccctgcagt gaagggaaac  1440
tttctcttca acggttctgt catttcagga ccaggattca ctggtggaga cctcgttaga  1500
ctcaacagca gtggaaataa cattcagaat agagggtata ttgaagttcc aattcacttc  1560
ccatccacat ctaccagata tagagttcgt gtgaggtatg cttctgtgac ccctattcac  1620
ctcaacgtta attggggtaa ttcatccatc ttctccaata cagttccagc tacagctacc  1680
tccttggata atctccaatc cagcgatttc ggttactttg aaagtgccaa tgcttttaca  1740
tcttcactcg gtaacatcgt gggtgttaga aactttagtg ggactgcagg agtgattatc  1800
gacagattcg agttcattcc agttactgca acactcgagg ctgaatataa tctggaaaga  1860
gcgcagaagg cggtgaatgc gctgtttacg tctacaaacc aactagggct aaaaacaaat  1920
gtaacggatt atcatattga tcaagtgtcc aatttagtta cgtatttatc ggatgaattt  1980
tgtctggatg aaaagcgaga attgtccgag aaagtcaaac atgcgaagcg actcagtgat  2040
gaacgcaatt tactccaaga ttcaaatttc aaagacatta ataggcaacc agaacgtggg  2100
tggggcggaa gtacagggat taccatccaa ggaggggatg acgtatttaa agaaaattac  2160
gtcacactat caggtacctt tgatgagtgc tatccaacat atttgtatca aaaaatcgat  2220
```

-continued

```
gaatcaaaat taaaagcctt tacccgttat caattaagag ggtatatcga agatagtcaa    2280
gacttagaaa tctatttaat tcgctacaat gcaaaacatg aaacagtaaa tgtgccaggt    2340
acgggttcct tatggccgct ttcagcccaa agtccaatcg gaaagtgtgg agagccaat     2400
cgatgcgcgc cacaccttga atggaatcct gacttagatt gttcgtgtag ggatggagaa    2460
aagtgtgccc atcattcgca tcatttctcc ttagacattg atgtaggatg tacagactta   2520
aatgaggacc taggtgtatg ggtgatcttt aagattaaga cgcaagatgg gcacgcaaga    2580
ctagggaatc tagagtttct cgaagagaaa ccattagtag gagaagcgct agctcgtgtg    2640
aaaagagcgg agaaaaatg gagagacaaa cgtgaaaaat tggaatggga aacaaatatc     2700
gtttataaag aggcaaaaga atctgtagat gctttatttg taaactctca atatgatcaa    2760
ttacaagcgg atacgaatat tgccatgatt catgcggcag ataaacgtgt tcatagcatt    2820
cgagaagctt atctgcctga gctgtctgtg attccgggtg tcaatgcggc tattttgaa     2880
gaattagaag ggcgtatttt cactgcattc tccctatatg atgcgagaaa tgtcattaaa   2940
aatggtgatt ttaataatgg cttatcctgc tggaacgtga aagggcatgt agatgtagaa    3000
gaacaaaaca accaacgttc ggtccttgtt gttccggaat gggaagcaga agtgtcacaa    3060
gaagttcgtg tctgtccggg tcgtggctat atccttcgtg tcacagcgta caaggaggga    3120
tatggagaag gttgcgtaac cattcatgag atcgagaaca atacagacga actgaagttt    3180
agcaactgcg tagaagagga aatctatcca aataacacgg taacgtgtaa tgattatact    3240
gtaaatcaag aagaatacgg aggtgcgtac acttctcgta atcgaggata taacgaagct    3300
ccttccgtac cagctgatta tgcgtcagtc tatgaagaaa aatcgtatac agatggacga    3360
agagagaatc cttgtgaatt taacagaggg tatagggatt acacgccact accagttggt    3420
tatgtgacaa aagaattaga atacttccca gaaaccgata aggtatggat tgagattgga    3480
gaaacggaag gaacatttat cgtggacagc gtggaattac tccttatgga ggaa          3534
```

<210> 26
<211> 3534
<212> DNA
<213> Artificial Sequence

<220>
<223> Description of Artificial Sequence:synthetic
structural gene encoding insecticidal protein
derived from B.t.k. HD-73

<400> 26
atggacaaca acccaaacat caacgaatgc attccataca actgcttgag taacccagaa 60
gttgaagtac ttggtggaga acgcattgaa accggttaca ctcccatcga catctccttg 120
tccttgacac agtttctgct cagcgagttc gtgccaggtg ctgggttcgt tctcggacta 180
gttgacatca tctggggtat ctttggtcca tctcaatggg atgcattcct ggtgcaaatt 240
gagcagttga tcaaccagag gatcgaagag ttcgccagga accaggccat ctctaggttg 300
gaaggattga gcaatctcta ccaaatctat gcagagagct tcagagagtg ggaagccgat 360
cctactaacc cagctctccg cgaggaaatg cgtattcaat tcaacgacat gaacagcgcc 420
ttgaccacag ctatcccatt gttcgcagtc cagaactacc aagttcctct cttgtccgtg 480
tacgttcaag cagctaatct tcacctcagc gtgcttcgag acgttagcgt gtttgggcaa 540
aggtggggat tcgatgctgc aaccatcaat agccgttaca acgaccttac taggctgatt 600
ggaaactaca ccgaccacgc tgttcgttgg tacaacactg gcttggagcg tgtctggggt 660

```
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc cacacttgat ggacatcttg    900
aacagcataa ctatctacac cgatgctcac agaggagagt attactggtc tggacaccag    960
atcatggcct ctccagttgg attcagcggg cccgagttta cctttcctct ctatggaact   1020
atgggaaacg ccgctccaca acaacgtatc gttgctcaac taggtcaggg tgtctacaga   1080
accttgtctt ccaccttgta cagaagaccc ttcaatatcg gtatcaacaa ccagcaactt   1140
tccgttcttg acggaacaga gttcgcctat ggaacctctt ctaacttgcc atccgctgtt   1200
tacagaaaga gcggaaccgt tgattccttg gacgaaatcc caccacagaa caacaatgtg   1260
ccacccaggc aaggattctc ccacaggttg agccacgtgt ccatgttccg ttccggattc   1320
agcaacagtt ccgtgagcat catcagagct cctatgttct cttggataca ccgtagtgct   1380
gagttcaaca acatcatcgc atccgatagt attactcaaa tccctgcagt gaagggaaac   1440
tttctcttca acggttctgt catttcagga ccaggattca ctggtggaga cctcgttaga   1500
ctcaacagca gtggaaataa cattcagaat agagggtata ttgaagttcc aattcacttc   1560
ccatccacat ctaccagata tagagttcgt gtgaggtatg cttctgtgac ccctattcac   1620
ctcaacgtta attggggtaa ttcatccatc ttctccaata cagttccagc tacagctacc   1680
tccttggata atctccaatc cagcgatttc ggttactttg aaagtgccaa tgcttttaca   1740
tcttcactcg gtaacatcgt gggtgttaga aactttagtg ggactgcagg agtgattatc   1800
gacagattcg agttcattcc agttactgca acactcgagg ctgagtacaa ccttgagaga   1860
gcccagaagg ctgtgaacgc cctctttacc tccaccaatc agcttggctt gaaaactaac   1920
gttactgact atcacattga ccaagtgtcc aacttggtca cctaccttag cgatgagttc   1980
tgcctcgacg agaagcgtga actctccgag aaagttaaac acgccaagcg tctcagcgac   2040
gagaggaatc tcttgcaaga ctccaacttc aaagacatca acaggcagcc agaacgtggt   2100
tggggtggaa gcaccgggat caccatccaa ggaggcgacg atgtgttcaa ggagaactac   2160
gtcaccctct ccggaacttt cgacgagtgc taccctacct acttgtacca gaagatcgat   2220
gagtccaaac tcaaagcctt caccaggtat caacttagag gctacatcga agacagccaa   2280
gaccttgaaa tctactcgat caggtacaat gccaagcacg agaccgtgaa tgtcccaggt   2340
actggttccc tctggccact ttctgcccaa tctcccattg ggaagtgtgg agagcctaac   2400
agatgcgctc cacaccttga gtggaatcct gacttggact gctcctgcag ggatggcgag   2460
aagtgtgccc accattctca tcacttctcc ttggacatcg atgtgggatg tactgacctg   2520
aatgaggacc tcggagtctg ggtcatcttc aagatcaaga cccaagacgg cacgcaaga    2580
cttggcaacc ttgagtttct cgaagagaaa ccattggtcg gtgaagctct cgctcgtgtg   2640
aagagagcag agaagaagtg gagggacaaa cgtgagaaac tcgaatggga aactaacatc   2700
gtttacaagg aggccaaaga gtccgtggat gctttgttcg tgaactccca atatgatcag   2760
ttgcaagccg acaccaacat cgccatgatc cacgccgcag acaaacgtgt gcacagcatt   2820
cgtgaggctt acttgcctga gttgtccgtg atccctggtg tgaacgctgc catcttcgag   2880
gaacttgagg gacgtatctt taccgcattc tccttgtacg atgccagaaa cgtcatcaag   2940
aacggtgact tcaacaatgg cctcagctgc tggaatgtga aggtcatgt ggacgtggag    3000
gaacagaaca atcagcgttc cgtcctggtt gtgcctgagt gggaagctga agtgtcccaa   3060
```

```
gaggttagag  tctgtccagg  tagaggctac  attctccgtg  tgaccgctta  caaggaggga   3120
tacggtgagg  gttgcgtgac  catccacgag  atcgagaaca  acaccgacga  gcttaagttc   3180
tccaactgcg  tcgaggaaga  aatctatccc  aacaacaccg  ttacttgcaa  cgactacact   3240
gtgaatcagg  aagagtacgg  aggtgcctac  actagccgta  acagaggtta  caacgaagct   3300
ccttccgttc  ctgctgacta  tgcctccgtg  tacgaggaga  aatcctacac  agatggcaga   3360
cgtgagaacc  cttgcgagtt  caacagaggt  tacagggact  acacaccact  tccagttggc   3420
tatgttacca  aggagcttga  gtactttcct  gagaccgaca  aagtgtggat  cgagatcggt   3480
gaaaccgagg  gaaccttcat  cgtggacagc  gtggagcttc  tcttgatgga  ggaa         3534

< 210 > 27
< 211 > 3531
< 212 > DNA
< 213 > Artificial Sequence

< 220 >
< 223 > Description of Artificial Sequence:synthetic
        structural gene encoding a fusion protein derived
        from; B.t.k. HD-1 and B.t.k. HD-73

< 400 > 27 atggacaaca  acccaaacat  caacgaatgc  attccataca  actgcttgag  taacccagaa     60
gttgaagtac  ttggtggaga  acgcattgaa  accggttaca  ctcccatcga  catctccttg    120
tccttgacac  agtttctgct  cagcgagttc  gtgccaggtg  ctgggttcgt  tctcggacta    180
gttgacatca  tctggggtat  ctttggtcca  tctcaatggg  atgcattcct  ggtgcaaatt    240
gagcagttga  tcaaccagag  gatcgaagag  ttcgccagga  accaggccat  ctctaggttg    300
gaaggattga  gcaatctcta  ccaaatctat  gcagagagct  tcagagagtg  ggaagccgat    360
cctactaacc  cagctctccg  cgaggaaatg  cgtattcaat  tcaacgacat  gaacagcgcc    420
ttgaccacag  ctatcccatt  gttcgcagtc  cagaactacc  aagttcctct  cttgtccgtg    480
tacgttcaag  cagctaatct  tcacctcagc  gtgcttcgag  acgttagcgt  gtttgggcaa    540
aggtggggat  tcgatgctgc  aaccatcaat  agccgttaca  acgaccttac  taggctgatt    600
ggaaactaca  ccgaccacgc  tgttcgttgg  tacaacactg  gcttggagcg  tgtctggggt    660
cctgattcta  gagattggat  tagatacaac  cagttcagga  gagaattgac  cctcacagtt    720
ttggacattg  tgtctctctt  cccgaactat  gactccagaa  cctaccctat  ccgtacagtg    780
tcccaactta  ccagagaaat  ctatactaac  ccagttcttg  agaacttcga  cggtagcttc    840
cgtggttctg  cccaaggtat  cgaaggctcc  atcaggagcc  cacacttgat  ggacatcttg    900
aacagcataa  ctatctacac  cgatgctcac  agaggagagt  attactggtc  tggacaccag    960
atcatggcct  ctccagttgg  attcagcggg  cccgagttta  cctttcctct  ctatggaact   1020
atgggaaacg  ccgctccaca  acaacgtatc  gttgctcaac  taggtcaggg  tgtctacaga   1080
accttgtctt  ccaccttgta  cagaagaccc  ttcaatatcg  gtatcaacaa  ccagcaactt   1140
tccgttcttg  acggaacaga  gttcgcctat  ggaacctctt  ctaacttgcc  atccgctgtt   1200
tacagaaaga  gcggaaccgt  tgattccttg  gacgaaatcc  caccacagaa  caacaatgtg   1260
ccacccaggc  aaggattctc  ccacaggttg  agccacgtgt  ccatgttccg  ttccggattc   1320
agcaacagtt  ccgtgagcat  catcagagct  cctatgttct  catggattca  tcgtagtgct   1380
gagttcaaca  atatcattcc  ttcctctcaa  atcacccaaa  tccattgac   caagtctact   1440 aaccttggat  ctggaacttc  tgtcgtgaaa  ggaccaggct  tcacaggagg  tgatattctt   1500
agaagaactt  ctcctggcca  gattagcacc  ctcagagtta  acatcactgc  accactttct   1560
```

-continued

```
caaagatatc gtgtcaggat tcgttacgca tctaccacta acttgcaatt ccacacctcc    1620
atcgacggaa ggcctatcaa tcagggtaac ttctccgcaa ccatgtcaag cggcagcaac    1680
ttgcaatccg gcagcttcag aaccgtcggt ttcactactc ctttcaactt ctctaacgga    1740
tcaagcgttt tcacccttag cgctcatgtg ttcaattctg gcaatgaagt gtacattgac    1800
cgtattgagt ttgtgcctgc cgaagttacc ctcgaggctg agtacaacct tgagagagcc    1860
cagaaggctg tgaacgccct ctttacctcc accaatcagc ttggcttgaa aactaacgtt    1920
actgactatc acattgacca agtgtccaac ttggtcacct accttagcga tgagttctgc    1980
ctcgacgaga agcgtgaact ctccgagaaa gttaaacacg ccaagcgtct cagcgacgag    2040
aggaatctct tgcaagactc caacttcaaa gacatcaaca ggcagccaga acgtggttgg    2100
ggtggaagca ccgggatcac catccaagga ggcgacgatg tgttcaagga gaactacgtc    2160
accctctccg gaactttcga cgagtgctac cctacctact tgtaccagaa gatcgatgag    2220
tccaaactca aagccttcac caggtatcaa cttagaggct acatcgaaga cagccaagac    2280
cttgaaatct actcgatcag gtacaatgcc aagcacgaga ccgtgaatgt cccaggtact    2340
ggttccctct ggccactttc tgcccaatct cccattggga agtgtggaga gcctaacaga    2400
tgcgctccac accttgagtg gaatcctgac ttggactgct cctgcaggga tggcgagaag    2460
tgtgcccacc attctcatca cttctccttg gacatcgatg tgggatgtac tgacctgaat    2520
gaggacctcg gagtctgggt catcttcaag atcaagaccc aagacggaca cgcaagactt    2580
ggcaaccttg agtttctcga agagaaacca ttggtcggtg aagctctcgc tcgtgtgaag    2640
agagcagaga agaagtggag ggacaaacgt gagaaactcg aatgggaaac taacatcgtt    2700
tacaaggagg ccaaagagtc cgtggatgct ttgttcgtga actcccaata tgatcagttg    2760
caagccgaca ccaacatcgc catgatccac gccgcagaca aacgtgtgca cagcattcgt    2820
gaggcttact tgcctgagtt gtccgtgatc cctggtgtga acgctgccat cttcgaggaa    2880
cttgagggac gtatctttac cgcattctcc ttgtacgatg ccagaaacgt catcaagaac    2940
ggtgacttca acaatggcct cagctgctgg aatgtgaaag gtcatgtgga cgtggaggaa    3000
cagaacaatc agcgttccgt cctggttgtg cctgagtggg aagctgaagt gtcccaagag    3060
gttagagtct gtccaggtag aggctacatt ctccgtgtga ccgcttacaa ggagggatac    3120
ggtgagggtt gcgtgaccat ccacgagatc gagaacaaca ccgacgagct taagttctcc    3180
aactgcgtcg aggaagaaat ctatcccaac aacaccgtta cttgcaacga ctacactgtg    3240
aatcaggaag agtacggagg tgcctacact agccgtaaca gaggttacaa cgaagctcct    3300
tccgttcctg ctgactatgc ctccgtgtac gaggagaaat cctacacaga tggcagacgt    3360
gagaacctt gcgagttcaa cagaggttac agggactaca caccacttcc agttggctat    3420
gttaccaagg agcttgagta ctttcctgag accgacaaag tgtggatcga gatcggtgaa    3480
accgagggaa ccttcatcgt ggacagcgtg gagcttctct tgatggagga a             3531
```

We claim:

1. A heterologous gene construct comprising a structural coding sequence which encodes an insecticidal protein derived from *B.k.* HD-1, said structural coding sequence comprising SEQ ID NO:20.

2. A heterologous gene construct comprising a structural coding sequence which encodes an insecticidal protein derived from *B.t.k.* HD-73, said structural coding sequence comprising SEQ ID NO:21.

3. A heterologous gene construct comprising a structural coding sequence which encodes an insecticidal protein derived from *B.t.k.* HD-1, said structural coding sequence comprising SEQ ID NO:22.

4. A heterologous gene construct comprising a structural coding sequence which encodes an insecticidal protein derived from *B.t.k.* HD-73, said structural coding sequence comprising SEQ ID NO:23.

5. A heterologous gene construct comprising a structural coding sequence which encodes an insecticidal protein derived from *B.t.k.* HD-73, said structural coding sequence comprising SEQ ID NO:24.

6. A heterologous gene construct comprising a structural coding sequence which encodes an insecticidal protein derived from *B.t.k.* HD-73, said structural coding sequence comprising SEQ ID NO:25.

7. A heterologous gene construct comprising a structural coding sequence which encodes an insecticidal protein derived from *B.t.k.* HD-73, said structural coding sequence comprising SEQ ID NO:26.

8. A heterologous gene construct comprising a structural coding sequence which encodes a fusion protein comprising the N-terminal 610 amino acids of a toxin protein derived from *B.t.k.* HD-1 and the C-terminal 567 amino acids of a toxin protein derived from *B.t.k.* HD-73, said structural coding sequence comprising SEQ ID NO:27.

* * * * *